United States Patent
Arcus et al.

(10) Patent No.: US 9,181,543 B2
(45) Date of Patent: Nov. 10, 2015

(54) OB FOLD DOMAINS

(75) Inventors: Vickery L. Arcus, Hamilton (NZ); John D. Steemson, Hamilton (NZ); Matthias Baake, Berlin (DE)

(73) Assignee: OBodies Limited, Hamilton (NZ)

( * ) Notice: Subject to any disclaimer, the term of this patent is extended or adjusted under 35 U.S.C. 154(b) by 1493 days.

(21) Appl. No.: 12/302,494

(22) PCT Filed: May 25, 2007

(86) PCT No.: PCT/NZ2007/000125
§ 371 (c)(1),
(2), (4) Date: Aug. 13, 2009

(87) PCT Pub. No.: WO2007/139397
PCT Pub. Date: Dec. 6, 2007

(65) Prior Publication Data
US 2010/0048413 A1    Feb. 25, 2010

Related U.S. Application Data

(60) Provisional application No. 60/809,105, filed on May 26, 2006.

(51) Int. Cl.
| | |
|---|---|
| *C40B 40/10* | (2006.01) |
| *C12N 15/10* | (2006.01) |
| *C07K 14/00* | (2006.01) |
| *C07K 16/00* | (2006.01) |
| *C07K 16/40* | (2006.01) |
| *C07K 16/44* | (2006.01) |
| *C12N 9/00* | (2006.01) |

(52) U.S. Cl.
CPC ............ *C12N 15/1037* (2013.01); *C07K 14/00* (2013.01); *C07K 16/00* (2013.01); *C07K 16/40* (2013.01); *C07K 16/44* (2013.01); *C12N 9/93* (2013.01); *C12Y 601/01012* (2013.01); *C07K 2299/00* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 5,831,012 | A  | 11/1998 | Nilsson et al. |
| 6,534,628 | B1 | 3/2003  | Nilsson et al. |
| 6,740,734 | B1 | 5/2004  | Nilsson et al. |

(Continued)

FOREIGN PATENT DOCUMENTS

| | | |
|---|---|---|
| CA | 2378871 A1   | 1/2001 |
| EP | 1 930 342 A1 | 6/2008 |

(Continued)

OTHER PUBLICATIONS

Short et al. (Dec. 1, 1995) Journal of Biological Chemistry vol. 270 pp. 28541 to 28550.*

(Continued)

*Primary Examiner* — Christian Boesen
(74) *Attorney, Agent, or Firm* — Morrison & Foerster LLP

(57) ABSTRACT

Provided herein are modified OB-fold domains having desired properties; methods of producing libraries of modified OB-fold domains; the libraries of modified OB-fold domains produced by such methods; methods for screening such libraries of modified OB-fold domains for desired biological activities; and the modified OB-fold domains identified from such libraries. Provided herein are modified OB-fold domains obtainable from *Pyrobaculum aerophilum* that exhibit modified binding interactions.

19 Claims, 17 Drawing Sheets

(56) References Cited

U.S. PATENT DOCUMENTS

| | | | |
|---|---|---|---|
| 6,818,418 | B1 | 11/2004 | Lipovsek et al. |
| 7,115,396 | B2 | 10/2006 | Lipovsek et al. |
| 7,601,803 | B1 | 10/2009 | Fiedler et al. |
| 2004/0009530 | A1 | 1/2004 | Wilson et al. |
| 2005/0255548 | A1 | 11/2005 | Lipovsek et al. |
| 2008/0103055 | A1 | 5/2008 | Kristensen |
| 2010/0145008 | A1 | 6/2010 | Pecorari et al. |

FOREIGN PATENT DOCUMENTS

| | | | |
|---|---|---|---|
| WO | WO-02/32925 | A2 | 4/2002 |
| WO | WO-2006/013468 | A2 | 2/2006 |
| WO | WO-2006/013468 | A3 | 2/2006 |
| WO | WO-2008/068637 | A2 | 6/2008 |
| WO | WO-2008/068637 | A3 | 6/2008 |

OTHER PUBLICATIONS

Kerr et al. (Jun. 1, 2003) EMBO Journal vol. 22 pp. 2561 to 2570.*
Accession No. Q8ZYM8, Aspartate—tRNA Ligase, located at <http://www.uniprot.org/uniprot/Q8ZYM8>, last visited on Jun. 11, 2013, five pages.
Affibody Information, located at <http://www.affibody.com>, last visited on Jun. 7, 2013, two pages.
Alexandrescu, A. et al. (1995). "NMR Structure of a Stable "OB-Fold" Sub-Domain Isolated From Staphylococcal Nuclease," *J. Mol. Biol.* 250(2):134-143.
Altamirano, M.M. et al. (Feb. 10, 2000). "Directed Evolution of a New Catalytic Activity Using the α/β-Barrel Scaffold," *Nature* 403(6770):617-622.
Arcus, V. et al. (Jul. 2007). "Superantigen Architecture: Functional Decoration on a Conserved Scaffold," Chapter 6 in *Superantigens: Molecular Basis for Their Role in Human Diseases*, First Edition, Kotb, M. and Fraser, J.D., eds., ASM Press: Washington, DC, pp. 93-102.
Arcus, V. et al. (May 26, 2000). "Conservation and Variation in Superantigen Structure and Activity Highlighted by the Three-Dimensional Structures of Two New Superantigens From Streptococcus Pyogenes," *J. Mol. Biol.* 299(1):157-168.
Arcus, V. (Dec. 1, 2002). "OB-Fold Domains: A Snapshot of the Evolution of Sequence, Structure and Function," *Curr. Opin. Struct. Biol.* 12(6):794-801.
Atwell, S. et al. (Nov. 7, 1997). "Structural Plasticity in a Remodeled Protein-Protein Interface," *Science* 278:1125-1128.
Bäckström, M. (1994). "Insertion of a HIV-1-Neutralizing Epitope in a Surface-Exposed Internal Region of the Cholera Toxin B-Subunit," *Gene* 149:211-217.
Bäckström, M. et al. (Nov. 20, 1995). "Characterization of an Internal Permissive Site in the Cholera Toxin B-Subunit and Insertion of Epitopes From Human Immunodeficiency Virus-1, Hepatitis B Virus and Enterotoxigenic *Escherichia coli*," *Gene* 165(2):163-171.
Ballinger, M.D. et al. (May 8, 1998). "Selection of Heregulin Variants Having Higher Affinity for the ErbB3 Receptor by Monovalent Phage Display," *J. Biol. Chem.* 273(19):11675-11684.
Battiste, J.L. et al. (Jan. 2000). "The eIF1A Solution Structure Reveals a Large RNA-Binding Surface Important for Scanning Function," *Mol. Cell* 5(1):109-119.
Binz, H. K. (Sep. 12, 2003). "Designing Repeat Proteins: Well-Expressed, Soluble and Stable Proteins From Combinatorial Libraries of Consensus Ankyrin Repeat Proteins," *J. Mol. Biol.* 332(2):489-503.
Binz, H.K. et al. (Oct. 1, 2005). "Engineering Novel Binding Proteins From Nonimmunoglobulin Domains," *Nature Biotechnology* 23(10):1257-1268.
Binz, H.K. et al. (2005). "Engineered Proteins as Specific Binding Reagents," *Current Opinion in Biotechnology* 16:459-469.
Brevet, A. et al. (Aug. 15, 2003). "Switching tRNA Specificity of an Aminoacyl-tRNA Synthetase by Site-Directed Peptide Transplantation," *J. Biol. Chem.* 278(33):30927-30935.

De Bono. S. et al. (Feb. 1, 2005, e-pub. Jan. 25, 2005). "A Segment of Cold Shock Protein Directs the Folding of a Combinatorial Protein," *PNAS* 102(5):1396-1401.
Drevelle, A. et al. (Apr. 28, 2006, e-pub. Feb. 20, 2006). "Structures of In Vitro Evolved Binding Sites on Neocarzinostatin Scaffold Reveal Unanticipated Evolutionary Pathways," *Journal of Molecular Biology* 358(2):455-471.
Ebersbach, H. et al. (Sep. 7, 2007, e-pub. Jun. 22, 2007). "Affilin-Novel Binding Molecules Based on Human γ-B-Crystallin, an All β-Sheet Protein," *J. Mol.Biol.* 372(1):172-185.
Extended European Search Report mailed on Nov. 30, 2010, for EP Patent Application No. 07793950.2, filed on May 25, 2007, 10 pages.
Fekete, C.A. et al. (2005). "The eIF1A C-Terminal Domain Promotes Initiation Complex Assembly, Scanning and AUG Selection In Vivo," *The EMBO Journal* 24(20):3588-3601.
Feng, L. et al. (May 13, 2003). "Expanding tRNA Recognition of a tRNA Synthetase by a Single Amino Acid Change," *PNAS* 100(10):5676-5681.
Gao, Y.G. et al. (Sep. 1998). "The Crystal Structure of the Hyperthermophile Chromosomal Protein SSO7D Bound to DNA," *Nature Structural Biology* 5(9):782-786.
Gunnarsson, L.C. (Mar. 2004, e-pub. Apr. 13, 2004). "A Carbohydrate Binding Module as a Diversity-Carrying Scaffold," *Protein Eng. Des. Sel.* 17(3):213-221.
Gunneriusson, E. et al. (Oct. 1999). "Affinity Maturation of a Taq DNA Polymerase Specific Affibody by Helix Shuffling," *Protein Engineering* 12(10):873-878.
Heyd, B. et al. (May 20, 2003). "In Vitro Evolution of the Binding Specificity of Neocarzinostatin, an Enediyne-Binding Chromoprotein," *Biochemistry* 42(19):5674-5683.
Hosse, R.J. et al. (2006). "A New Generation of Protein Display Scaffolds for Molecular Recognition," *Protein Science* 15:14-27.
Hufton, S.E. (Jun. 23, 2000). "Development and Application of Cytotoxic T Lymphocyte-Associated Antigen 4 as a Protein Scaffold for the Generation of Novel Binding Ligands," *FEBS Letters* 475(3):225-231.
International Search Report mailed on Aug. 28, 2007, for PCT Patent Application No. PCT/NZ2007/000125 filed on May 25, 2007, four pages.
Jermutus, L. et al. (Jan. 2, 2001). "Tailoring In Vitro Evolution for Protein Affinity or Stability," *PNAS* 98(1):75-80.
Kerr, I.D. et al. (2003). "Insights Into ssDNA Recognition by the OB Fold From a Structural and Thermodynamic Study of Sulfolobus SSB Protein," *The EMBO Journal* 22(11):2561-2570.
Lei, M. et al. (Nov. 13, 2003). "DNA Self-Recognition in the Structure of Pot1 Bound to Telomeric Single-Stranded DNA," *Nature* 426:198-203.
Leiros, I. et al. (2005). "Crystal Structure and DNA-Binding Analysis of RecO From *Deinococcus radiodurans*," *EMBO Journal* 24(5):906-918.
Li, R. et al. (Jan. 2003). "Use of Phage Display to Probe the Evolution of Binding Specificity and Affinity in Integrins," *Protein Eng.* 16(1):65-72.
Martin, F. et al. (2004, e-pub. Aug. 2, 2004). "Single Amino Acid Changes in AspRS Reveal Alternative Routes for Expanding Its tRNA Repertoire In Vivo," *Nucleic Acids Research* 32(13):4081-4089.
McConnell, S.J. (Jul. 21, 1995). "Tendamistat as a Scaffold for Conformationally Constrained Phage Peptide Libraries," *J. Mol. Biol.* 250(4):460-470.
Meka, H. et al. (2005, e-pub. Nov. 10, 2005). "Crystal Structure and RNA Binding of the Rpb4/Rpb7 Subunits of Human RNA Polymerase II," *Nuc. Acids Research* 33(19):6435-6444.
Mirny, L.A. et al. (Aug. 6, 1999). "Universally Conserved Positions in Protein Folds: Reading Evolutionary Signals About Stability, Folding Kinetics and Function," *Journal of Molecular Biology* 291 (1):177-196.
Mou, T.C. et al. (Dec. 2003, e-pub. Nov. 13, 2003). "Binding and Reversible Denaturation of Double-Stranded DNA by Ff Gene 5 Protein," *Biopolymers* 70(4):637-648.
Murzin, A.G. (Mar. 1993). "OB(Oligonucleotide/Oligosaccharide Binding)-Fold: Common Structural and Functional Solution for Non-Homologous Sequences," *The EMBO Journal* 12(3):861-867.

(56) References Cited

OTHER PUBLICATIONS

Nord, K. et al. (Jun. 1995). "A Combinatorial Library of an α-Helical Bacterial Receptor Domain," *Protein Engineering* 8(6):601-608.

Norman, T.C. (Jul. 23, 1999). "Genetic Selection of Peptide Inhibitors of Biological Pathway," *Science* 285(5427):591-594.

Nuttall, S.D. (Aug. 1, 1999). "Design and Expression of Soluble CTLA-4 Variable Domain as a Scaffold for the Display of Functional Polypeptides," *Proteins* 36(2):217-227.

Peat, T. et al. (Sep. 15, 1998). "Structure of Translation Initiation Factor 5A from Pyrobaculum Aerophilum at 1.75 Å Resolution," *Structure* 6(9):1207-1214.

Peters, W.B. et al. (Mar. 1, 2005). "Effect of Mutation of the Sac7d Intercalating Residues on the Temperature Dependence of DNA Distortion and Binding Thermodynamics," *Biochem.* 44(12):4794-4804.

Scil Proteins Website Information, located at <http://www.scilproteins.com>, last visited on Jun. 7, 2013, four pages.

Scil Proteins GmbH Afflin Technology, located at <http://www.web30.webbox300.server-home.net>, last visited on Dec. 10, 2010, 12 pages.

Short, M.K. et al. (Dec. 1, 1995). "Contribution of Antibody Heavy Chain CDR1 to Digoxin Binding Analyzed by Random Mutagenesis of Phage-Displayed Fab 26-10," *Journal of Biological Chemistry* 270(48):28541-28550.

Sidhu, S.S. et al. (2000). "Phage Display for Selection of Novel Binding Peptides," *Methods in Enzymology* 328:333-363.

Skerra, A. (Jun. 2001). "Anticalins: A New Class of Engineered Ligand-Binding Proteins with Antibody-Like Properties," *Reviews in Mol. Biotechnol.* 74(4):257-275.

Skerra, A. (Aug. 2007, e-pub. Jul. 20, 2007). "Alternative Non-Antibody Scaffolds for Molecular Recognition," *Curr. Opin. Biotechnol.* 18(4):295-304.

Stein, P.E. et al. (1994). "The Crystal Structure of Pertussis Toxin," *Structure* 2(1):45-47.

Stemmer, W.P.C. (Aug. 4, 1994). "Rapid Evolution of a Protein In Vitro by DNA Shuffling," *Nature* 370:389-391.

Stumpp, M.T. (Sep. 12, 2003). "Designing Repeat Proteins: Modular Leucine-Rich Repeat Protein Libraries Based on the Mammalian Ribonuclease Inhibitor Family," *J. Mol Biol.* 332(2):471-487.

Swairjo, M.A. et al. (2000). "Crystal Structure of Trbp111: A Structure-Specific tRNA-Binding Protein," *The EMBO Journal* 19(23):6287-6298.

Theobald, D.L. (2003). "Nucleic Acid Recognition by OB-Fold Proteins," *Annu. Rev. Biophys. Biomol. Struct.* 32:115-133.

Wahlberg, E. et al. (Mar. 18, 2003, e-pub. Feb. 19, 2003). "An Affibody in Complex with a Target Protein: Structure and Coupled Folding," *PNAS* 100(6):3185-3190.

Written Opinion of the International Searching Authority mailed on Aug. 28, 2007, for PCT Patent Application No. PCT/NZ2007/000125 filed on May 25, 2007, eight pages.

Yang, H. et al. (Sep. 13, 2002). "BRCA2 Function in DNA Binding and Recombination from a BRCA2-DSS1-ssDNA Structure," *Science* 297:1837-1848.

Zahnd, C. et al. (Feb. 15, 2010). "Efficient Tumor Targeting with High-Affinity Designed Ankyrin Repeat Proteins: Effects of Affinity and Molecular Size," *Cancer Res.* 70(4):1595-1605.

Zhao, A. et al. (Apr. 2004). "A Conformation-Constrained Peptide Library Based on Insect Defensin A.," *Peptides* 25(4):629-635.

\* cited by examiner

```
H.sapiens       EIMDAAEDYAKERYGISSMIQSQE--KPDRVLVRVRDLTIQK-ADEVVWVRARVHTSRAK    72
S.cerevisiae    EKKAAAEDTAKDNYGKLPLIQSRDSDRTGQKRVKFVDLDEAKDSDKEVLFRARVHNTRQQ   120
A.thialana      ---------------------------------SNLVEEIVGSEVSIRGRLHKNRLV     24
P.aerophilum    -------------------------MYPKKTHWTAEITPNLHGTEVVVAGWVWELRDI    33
E.coli          ----------------------------MRTEYCGQLRLSHVGQQVTLCGWVNRRRDL    30
                                                         * . . :       *
sec. struct.                                             bbbbbbbbbbbbbbbb
                                                                beta1

H.sapiens       GK-QCFLVLRQQQFNVQALVAVG--DHASKQMVKFAANINKESIVDVEGVVRKVNQK--I   127
S.cerevisiae    GATLAFLTLRQQASLIQGLVKANKEGTISKNMVKWAGSLNLESIVLVRGIVKKVDEP--I   178
A.thialana      GT-KLFVILRESGFTVQCVVEET---RVGANMIKFVKQLSRESVVELIGVVSHPKKP--L    78
P.aerophilum    GR-VKFVVVRDREGFVQVTLKAG---KTPDHLFKVFAELSREDVVVIKGIVEASKIA--K    87
E.coli          GS-LIFIDMRDREGIVQVFFDPD-----RADALKLASELRNEFCIQVTGTVRARDEKNIN   84
                *    *: :*:    :*            ..*  .:  *   :  : * *   .
sec. struct.     bbbbbbbbbb   bbbbbbbbb         hhhhhhhh      bbbbbbbbbbbb
                    beta2        beta3                            beta4

H.sapiens       GSCTQQDVELHVQKIYVISLAEPRLPLQLDDAVRPEAEGEEEGRATVNQDTRLDNRVIDL   187
S.cerevisiae    KSATVQNLEIHITKIYTISETPEALPILLEDASRSEAEAEAAGLPVVNLDTRLDYRVIDL   238
A.thialana      TGTTQQ-VEIHVRKMYCLSRSLPNLPLVVEDAARSESDIEKSG----------------   120
P.aerophilum    SG-----VEIFPSEIWILNKAKP-LPIDIWSETPDLAT-------------RLKWRSVDL   128
E.coli          RDMATGEIEVLASSLTIIN-RADVLPLDSNHVNTEEAR-------------LKYRYLDL   129
                  .   :*:   .: :.    **:                :
sec. struct.    bbbbbbbbbbbbbbbbbb
                       beta5
```

Figure 5A

```
H.sapiens       IKRNDFQLIGIQDGYLSLLQDSGEVREDLRLPEGDLGKEIEQKYDCGEEILITVLSAMTE    60
S.cerevisiae    VKRSEYQLLDIDDGYLSLMTMDGETKDDVKAPEGELGDSMQAAFDEGKDLMVTIISAMGE    60
P.aerophilum    IEKFTAQILSVSGDVIQLMDMRD--YKTIEVPMKYVEEEAKGRLAPGAE--VEVWQILDR    56
                :::  *::.:...:.*:    . .:.  * :   :  ..:   * :  : : : :
sec. structure  bbbbbbbbbbb bbbbbbb    bbbbbb   hhhh     bbbbbbbbbb  b
                   beta1      beta2     beta3                beta4

H.sapiens       EAAVAIKAMAK-   71
S.cerevisiae    EAAISFKEAPRSD  73
P.aerophilum    YKIIRVK------  63
                 :  .*
sec. structure  bbbbb
                beta5
```

Figure 5B

```
P.a.      3    PKKTHWTAEI TPNLHGTEVV VAGWVWELRD IGRVKFVVVR DREGFVQVTL
P.kodak   1    MYRTHYSSEI TEELNGQKVK VAGWVWEVKD LGGIKFLWIR DRDGIVQITA
E.coli    1     MRTEYCGQL RLSHVGQQVT LCGWVNRRRD LGSLIFIDMR DREGIVQVFF
                 .*    ..       *  *    ***    .* .* . *   .*  **.* **.
sec. structure                         bbbbbbbbbbbbbbbbb bbbbbbbbb   bbbbbbb
                                              beta1           beta2        beta3

P.a.     53    KAGKTPDHLF KVFAELSRED VVVIKGIVEA SKI-----AK --SGVEIFPS
P.kodak  51    PKKKVDPELF KLIPKLRSED VVAVEGVVNF TPK-----AK --LGFEILPE
E.coli   50    DP--DRADAL KLASELRNEF CIQVTGTVRA RDEKNINRDM ATGEIEVLAS
                    *      *   *      . . * *                         *.
sec. structure bb    hhhhhhhhh       bbbbbbbbbbbbbbblllllllllllllbbbbbbb
                                            beta4                    beta5

P.a.     96    EIWILNKAKP
P.kodak  94    KIVVLNRAET
E.coli   98    SLTIINRADV
                . ..*.*
sec. structure bbbbb
```

Figure 5C

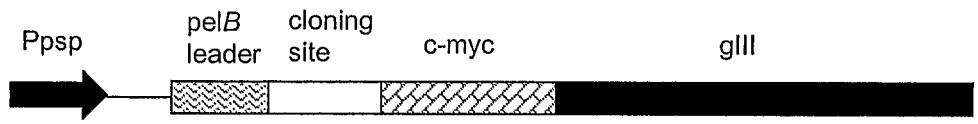

Figure 6

|              | 1   | 2 | 3 | 4 |
|--------------|-----|---|---|---|
| wt aspRS-OB  | I   | A | K | S |
| pMB16 (2x)   | R   | G | C | R |
| pMB17 (3x)   | K   | G | C | R |
| pMB12        | R   | G | C | A |
| asp03        | R   | G | C | L |
| pMB18        | R   | S | C | R |
| 310          | K   | A | F | R |
| 307          | K   | C | A | W |
| 312          | A   | R | R | V |
| pMB15        | L   | S | L | V |
|              |     |   |   |   |
| consensus    | R/K | G | C | R |

Figure 10

|  | strand 1 | | | | strand 2 | | | | | strand 3 | | | | loop 4/5 | | | |
|---|---|---|---|---|---|---|---|---|---|---|---|---|---|---|---|---|---|
| pos | 28 | 29 | 31 | 33 | 35 | 36 | 38 | 40 | 42 | 47 | 49 | 51 | 53 | 85 | 86 | 87 | 88 |
| OBwt | W | E | R | I | R | V | F | V | R | F | Q | T | K | I | A | K | S |
| clone | | | | | | | | | | | | | | | | | |
| A | | | | | | | | | | | | | | | | | |
| U1 | E | C | A | T | I | E | G | L | V | C | R | H | Q | G | Y | K | S |
| U2 | G | A | R | L | L | G | G | S | F | V | T | N | L | S | R | V | G |
| U3 | A | A | G | A | D | S | T | T | N | P | H | Q | D | Y | R | L | K |
| U4 | D | P | L | R | L | A | G | S | R | S | P | T | L | Q | R | Y | V |
| U5 | K | V | P | G | F | C | Y | R | E | S | L | A | S | L | G | H | F |
| U6 | I | S | D | R | G | T | L | E | I | A | I | Q | L | R | L | V | N |
| U7 | F | S | L | V | M | G | L | R | P | P | D | D | P | C | G | G | G |
| U8 | * | * | * | * | * | * | * | * | * | * | * | * | * | V | G | A | L |
| U9 | * | * | * | * | * | * | * | * | * | * | * | * | * | G | C | D | C |
| B | | | | | | | | | | | | | | | | | |
| S68 | R | S | V | G | R | V | A | N | Q | K | E | L | E | G | E | W | S |
| S81 | K | G | V | M | L | L | G | T | G | S | L | R | T | L | V | P | Q |
| C | | | | | | | | | | | | | | | | | |
| p16 | * | * | * | * | * | * | * | * | * | * | * | * | * | R | G | C | R |
| p17 | * | * | * | * | * | * | * | * | * | * | * | * | * | K | G | C | R |
| D | | | | | | | | | | | | | | | | | |
| D05 | Q | R | Y | R | K | R | S | S | V | P | T | C | R | W | N | C | G |
| D07 | R | K | R | R | P | A | Y | W | R | T | R | R | Q | R | K | G | S |
| D09 | W | R | R | W | L | A | T | R | K | S | R | T | R | W | W | V | W |
| D04 | S | C | C | A | K | R | W | Y | V | P | A | R | R | R | A | G | S |
| E | | | | | | | | | | | | | | | | | |
| L14 | S | D | L | A | R | A | Y | F | Y | E | M | T | A | G | W | R | D |
| L8 | A | S | G | Y | R | V | I | K | S | A | P | Y | E | G | V | G | R |
| L4 | G | E | A | F | D | M | T | A | R | E | P | T | L | G | S | T | S |
| L16 | A | S | V | G | P | R | W | F | R | E | T | E | T | G | L | R | W |
| L34 | V | G | M | E | A | L | G | E | R | P | E | T | E | G | Y | G | S |
| L42 | V | D | V | L | R | N | L | Q | S | R | L | N | A | I | Q | R | S |
| L6 | E | D | V | A | K | T | W | F | C | Q | I | E | V | S | R | A | V |
| L5 | T | D | V | A | T | W | F | Q | A | N | W | S | V | L | P | S | Y |
| L44 | T | D | V | A | T | W | F | Q | A | N | W | S | V | P | G | A | A |

Figure 12

SEQUENCE LISTING

```
<160> NUMBER OF SEQ ID NOS: 81

<210> SEQ ID NO 1
<211> LENGTH: 111
<212> TYPE: PRT
<213> ORGANISM: Pyrobaculum aerophilum

<400> SEQUENCE: 1

Val Tyr Pro Lys Lys Thr His Trp Thr Ala Glu Ile Thr Pro Asn Leu
1               5                   10                  15

His Gly Thr Glu Val Val Val Ala Gly Trp Val Glu Cys Leu Ala Asp
                20                  25                  30

Thr Gly Ile Glu Lys Gly Val Leu Val Val Asp Arg Glu Gly Gly Ala
            35                  40                  45

Cys Val Arg Val His Leu Gln Ala Gly Lys Thr Pro Asp His Leu Phe
    50                  55                  60

Lys Val Phe Ala Glu Leu Ser Arg Glu Asp Val Val Val Ile Lys Gly
65                  70                  75                  80

Ile Val Glu Ala Ser Lys Gly Tyr Lys Ser Gly Val Glu Ile Phe Pro
                85                  90                  95

Ser Glu Ile Trp Ile Leu Asn Lys Ala Lys Pro Leu Pro Ile Asp
                100                 105                 110

<210> SEQ ID NO 2
<211> LENGTH: 111
<212> TYPE: PRT
<213> ORGANISM: Pyrobaculum aerophilum

<400> SEQUENCE: 2

Val Tyr Pro Lys Lys Thr His Trp Thr Ala Glu Ile Thr Pro Asn Leu
1               5                   10                  15

His Gly Thr Glu Val Val Val Ala Gly Trp Val Gly Ala Leu Arg Asp
                20                  25                  30

Leu Gly Leu Gly Lys Gly Val Ser Val Phe Asp Arg Glu Gly Gly Ala
            35                  40                  45

Val Val Thr Val Asn Leu Leu Ala Gly Lys Thr Pro Asp His Leu Phe
    50                  55                  60

Lys Val Phe Ala Glu Leu Ser Arg Glu Asp Val Val Val Ile Lys Gly
65                  70                  75                  80
```

```
Ile Val Glu Ala Ser Lys Ser Arg Val Gly Val Glu Ile Phe Pro
                85                  90                  95

Ser Glu Ile Trp Ile Leu Asn Lys Ala Lys Pro Leu Pro Ile Asp
            100                 105                 110

<210> SEQ ID NO 3
<211> LENGTH: 111
<212> TYPE: PRT
<213> ORGANISM: Pyrobaculum aerophilum

<400> SEQUENCE: 3

Val Tyr Pro Lys Lys Thr His Trp Thr Ala Glu Ile Thr Pro Asn Leu
1               5                   10                  15

His Gly Thr Glu Val Val Val Ala Gly Trp Val Ala Ala Leu Gly Asp
                20                  25                  30

Ala Gly Asp Ser Lys Thr Val Thr Val Asn Asp Arg Glu Gly Gly Ala
                35                  40                  45

Pro Val His Val Gln Leu Asp Ala Gly Lys Thr Pro Asp His Leu Phe
            50                  55                  60

Lys Val Phe Ala Glu Leu Ser Arg Glu Asp Val Val Ile Lys Gly
65                  70                  75                  80

Ile Val Glu Ala Ser Lys Tyr Arg Leu Lys Gly Val Glu Ile Phe Pro
                85                  90                  95

Ser Glu Ile Trp Ile Leu Asn Lys Ala Lys Pro Leu Pro Ile Asp
            100                 105                 110

<210> SEQ ID NO 4
<211> LENGTH: 111
<212> TYPE: PRT
<213> ORGANISM: Pyrobaculum aerophilum

<400> SEQUENCE: 4

Val Tyr Pro Lys Lys Thr His Trp Thr Ala Glu Ile Thr Pro Asn Leu
1               5                   10                  15

His Gly Thr Glu Val Val Val Ala Gly Trp Val Asp Pro Leu Leu Asp
                20                  25                  30

Arg Gly Leu Ala Lys Gly Val Ser Val Arg Asp Arg Glu Gly Gly Ala
                35                  40                  45

Ser Val Pro Val Thr Leu Leu Ala Gly Lys Thr Pro Asp His Leu Phe
            50                  55                  60

Lys Val Phe Ala Glu Leu Ser Arg Glu Asp Val Val Ile Lys Gly
65                  70                  75                  80

Ile Val Glu Ala Ser Lys Gln Arg Tyr Val Gly Val Glu Ile Phe Pro
                85                  90                  95

Ser Glu Ile Trp Ile Leu Asn Lys Ala Lys Pro Leu Pro Ile Asp
            100                 105                 110

<210> SEQ ID NO 5
<211> LENGTH: 111
<212> TYPE: PRT
<213> ORGANISM: Pyrobaculum aerophilum

<400> SEQUENCE: 5

Val Tyr Pro Lys Lys Thr His Trp Thr Ala Glu Ile Thr Pro Asn Leu
1               5                   10                  15

His Gly Thr Glu Val Val Val Ala Gly Trp Val Lys Val Leu Pro Asp
                20                  25                  30
```

```
Gly Gly Phe Cys Lys Tyr Val Arg Val Glu Asp Arg Glu Gly Gly Ala
            35                  40                  45

Ser Val Leu Val Ala Leu Ser Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Leu Gly His Phe Gly Val Glu Ile Phe Pro
                    85                  90                  95

Ser Glu Ile Trp Ile Leu Asn Lys Ala Lys Pro Leu Pro Ile Asp
                100                 105                 110
```

<210> SEQ ID NO 6
<211> LENGTH: 111
<212> TYPE: PRT
<213> ORGANISM: Pyrobaculum aerophilum

<400> SEQUENCE: 6

```
Val Tyr Pro Lys Lys Thr His Trp Thr Ala Glu Ile Thr Pro Asn Leu
  1               5                  10                  15

His Gly Thr Glu Val Val Ala Gly Trp Val Ile Ser Leu Ser Asp
                 20                  25                  30

Arg Gly Gly Thr Lys Leu Val Glu Val Ile Asp Arg Glu Gly Gly Ala
            35                  40                  45

Ala Val Ile Val Gln Leu Leu Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Arg Leu Val Asn Gly Val Glu Ile Phe Pro
                    85                  90                  95

Ser Glu Ile Trp Ile Leu Asn Lys Ala Lys Pro Leu Pro Ile Asp
                100                 105                 110
```

<210> SEQ ID NO 7
<211> LENGTH: 111
<212> TYPE: PRT
<213> ORGANISM: Pyrobaculum aerophilum
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 7

```
Val Tyr Pro Lys Lys Thr His Trp Thr Ala Glu Ile Thr Pro Asn Leu
  1               5                  10                  15

His Gly Thr Glu Val Val Ala Gly Trp Val Phe Xaa Leu Leu Asp
                 20                  25                  30

Xaa Gly Met Gly Lys Leu Val Arg Val Pro Asp Arg Glu Gly Gly Ala
            35                  40                  45

Pro Val Asp Val Asp Leu Pro Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Cys Gly Gly Gly Gly Glu Ile Phe Pro
                    85                  90                  95
```

His Glu Ile Trp Ile Leu Asn Lys Gly Lys Pro Leu Pro Ile Asp
            100                 105                 110

<210> SEQ ID NO 8
<211> LENGTH: 109
<212> TYPE: PRT
<213> ORGANISM: Pyrobaculum aerophilum

<400> SEQUENCE: 8

Val Tyr Pro Lys Lys Thr His Trp Thr Ala Glu Ile Thr Pro Asn Leu
1               5                   10                  15

His Gly Thr Glu Val Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
    50                  55                  60

Phe Ala Glu Leu Ser Arg Glu Asp Val Val Ile Lys Gly Ile Val
65                  70                  75                  80

Glu Ala Ser Lys Val Gly Ala Leu Gly Val Glu Ile Phe Pro Ser Glu
                85                  90                  95

Ile Trp Ile Leu Asn Lys Ala Lys Pro Leu Pro Ile Asp
            100                 105

<210> SEQ ID NO 9
<211> LENGTH: 109
<212> TYPE: PRT
<213> ORGANISM: Pyrobaculum aerophilum

<400> SEQUENCE: 9

Val Tyr Pro Lys Lys Thr His Trp Thr Ala Glu Ile Thr Pro Asn Leu
1               5                   10                  15

His Gly Thr Glu Val Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
    50                  55                  60

Phe Ala Glu Leu Ser Arg Glu Asp Val Val Ile Lys Gly Ile Val
65                  70                  75                  80

Glu Ala Ser Lys Gly Cys Asp Cys Gly Val Glu Ile Phe Pro Ser Glu
                85                  90                  95

Ile Trp Ile Leu Asn Lys Ala Lys Pro Leu Pro Ile Asp
            100                 105

<210> SEQ ID NO 10
<211> LENGTH: 111
<212> TYPE: PRT
<213> ORGANISM: Pyrobaculum aerophilum

<400> SEQUENCE: 10

Val Tyr Pro Lys Lys Thr His Trp Thr Ala Glu Ile Thr Pro Asn Leu
1               5                   10                  15

His Gly Thr Glu Val Val Val Ala Gly Trp Val Arg Ser Leu Val Asp
            20                  25                  30

Gly Gly Arg Val Lys Ala Val Asn Val Gln Asp Arg Glu Gly Ala
        35                  40                  45

```
Lys Val Glu Val Leu Leu Glu Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Gly Glu Trp Ser Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 11
<211> LENGTH: 111
<212> TYPE: PRT
<213> ORGANISM: Pyrobaculum aerophilum

<400> SEQUENCE: 11

```
Val Tyr Pro Lys Lys Thr His Trp Thr Ala Glu Ile Thr Pro Asn Leu
 1               5                  10                  15

His Gly Thr Glu Val Val Val Ala Gly Trp Val Lys Gly Leu Val Asp
                20                  25                  30

Met Gly Leu Leu Lys Gly Val Thr Val Gly Asp Arg Glu Gly Gly Ala
                35                  40                  45

Ser Val Leu Val Arg Leu Thr Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Leu Val Pro Gln Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 12
<211> LENGTH: 109
<212> TYPE: PRT
<213> ORGANISM: Pyrobaculum aerophilum

<400> SEQUENCE: 12

```
Val Tyr Pro Lys Lys Thr His Trp Thr Ala Glu Ile Thr Pro Asn Leu
 1               5                  10                  15

His Gly Thr Glu Val Val Val Ala Gly Trp Val Trp Glu Leu Arg Asp
                20                  25                  30

Ile Gly Lys Val Lys Phe Val Val Arg Asp Arg Glu Gly Phe Val
                35                  40                  45

Gln Val Thr Leu Lys Ala Gly Lys Thr Pro Asp His Leu Phe Lys Val
 50                  55                  60

Phe Ala Glu Leu Ser Arg Glu Asp Val Val Ile Lys Gly Ile Val
 65                  70                  75                  80

Glu Ala Ser Lys Arg Gly Cys Arg Gly Val Glu Ile Phe Pro Ser Glu
                 85                  90                  95

Ile Trp Ile Leu Asn Lys Ala Lys Pro Leu Pro Ile Asp
            100                 105
```

<210> SEQ ID NO 13
<211> LENGTH: 109
<212> TYPE: PRT
<213> ORGANISM: Pyrobaculum aerophilum

<400> SEQUENCE: 13

```
Val Tyr Pro Lys Lys Thr His Trp Thr Ala Glu Ile Thr Pro Asn Leu
1               5                   10                  15

His Gly Thr Glu Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
50                  55                  60

Phe Ala Glu Leu Ser Arg Glu Asp Val Val Ile Lys Gly Ile Val
65                  70                  75                  80

Glu Ala Ser Lys Lys Gly Cys Arg Gly Val Glu Ile Phe Pro Ser Glu
                85                  90                  95

Ile Trp Ile Leu Asn Lys Ala Lys Pro Leu Pro Ile Asp
            100                 105
```

<210> SEQ ID NO 14
<211> LENGTH: 109
<212> TYPE: PRT
<213> ORGANISM: Pyrobaculum aerophilum

<400> SEQUENCE: 14

```
Val Tyr Pro Lys Lys Thr His Trp Thr Ala Glu Ile Thr Pro Asn Leu
1               5                   10                  15

His Gly Thr Glu Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
50                  55                  60

Phe Ala Glu Leu Ser Arg Glu Asp Val Val Ile Lys Gly Ile Val
65                  70                  75                  80

Glu Ala Ser Lys Arg Gly Cys Ala Gly Val Glu Ile Phe Pro Ser Glu
                85                  90                  95

Ile Trp Ile Leu Asn Lys Ala Lys Pro Leu Pro Ile Asp
            100                 105
```

<210> SEQ ID NO 15
<211> LENGTH: 109
<212> TYPE: PRT
<213> ORGANISM: Pyrobaculum aerophilum

<400> SEQUENCE: 15

```
Val Tyr Pro Lys Lys Thr His Trp Thr Ala Glu Ile Thr Pro Asn Leu
1               5                   10                  15

His Gly Thr Glu Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
50                  55                  60

Phe Ala Glu Leu Ser Arg Glu Asp Val Val Ile Lys Gly Ile Val
65                  70                  75                  80

Glu Ala Ser Lys Arg Ser Cys Arg Gly Val Glu Ile Phe Pro Ser Glu
                85                  90                  95

Ile Trp Ile Leu Asn Lys Ala Lys Pro Leu Pro Ile Asp
            100                 105
```

<210> SEQ ID NO 16
<211> LENGTH: 109
<212> TYPE: PRT
<213> ORGANISM: Pyrobaculum aerophilum

<400> SEQUENCE: 16

Val Tyr Pro Lys Lys Thr His Trp Thr Ala Glu Ile Thr Pro Asn Leu
1               5                   10                  15

His Gly Thr Glu Val Val Ala Gly Trp Val Trp Glu Leu Arg Asp
            20                  25                  30

Ile Gly Lys Val Lys Phe Val Val Arg Asp Arg Glu Gly Phe Val
        35                  40                  45

Gln Val Thr Leu Lys Ala Gly Lys Thr Pro Asp His Leu Phe Lys Val
50                  55                  60

Phe Ala Glu Leu Ser Arg Glu Asp Val Val Ile Lys Gly Ile Val
65                  70                  75                  80

Glu Ala Ser Lys Leu Ser Leu Val Gly Val Gly Ile Phe Pro Ser Glu
                85                  90                  95

Ile Trp Ile Leu Asn Lys Ala Lys Pro Leu Pro Ile Asp
            100                 105

<210> SEQ ID NO 17
<211> LENGTH: 111
<212> TYPE: PRT
<213> ORGANISM: Pyrobaculum aerophilum
<220> FEATURE:
<221> NAME/KEY: misc_feature
<222> LOCATION: (91)..(91)
<223> OTHER INFORMATION: Xaa can be any naturally occurring amino acid

<400> SEQUENCE: 17

Val Tyr Pro Lys Lys Thr His Trp Thr Ala Glu Ile Thr Pro Asn Leu
1               5                   10                  15

His Gly Thr Glu Val Val Ala Gly Trp Val Gln Arg Leu Tyr Asp
            20                  25                  30

Arg Gly Lys Arg Lys Ser Val Ser Val Val Asp Arg Glu Gly Gly Ala
        35                  40                  45

Pro Val Thr Val Cys Leu Arg Ala Gly Lys Thr Pro Asp His Leu Phe
50                  55                  60

Lys Val Phe Ala Glu Leu Ser Arg Glu Asp Val Val Ile Lys Gly
65                  70                  75                  80

Ile Val Glu Ala Ser Lys Trp Asn Cys Gly Xaa Val Glu Ile Phe Pro
                85                  90                  95

Ser Glu Ile Trp Ile Leu Asn Lys Ala Lys Pro Leu Pro Ile Asp
            100                 105                 110

<210> SEQ ID NO 18
<211> LENGTH: 111
<212> TYPE: PRT
<213> ORGANISM: Pyrobaculum aerophilum

<400> SEQUENCE: 18

Val Tyr Pro Lys Lys Thr His Trp Thr Ala Glu Ile Thr Pro Asn Leu
1               5                   10                  15

His Gly Thr Glu Val Val Ala Gly Trp Val Arg Lys Leu Arg Asp
            20                  25                  30

Arg Gly Pro Ala Lys Tyr Val Trp Val Arg Asp Arg Glu Gly Gly Ala
        35                  40                  45

```
Thr Val Arg Val Arg Leu Gln Ala Gly Lys Thr Pro Asp His Leu Phe
    50                  55                  60

Lys Val Phe Ala Glu Leu Ser Arg Glu Asp Val Val Ile Lys Gly
 65                  70                  75                  80

Ile Val Glu Ala Ser Lys Arg Lys Gly Ser Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 19
<211> LENGTH: 111
<212> TYPE: PRT
<213> ORGANISM: Pyrobaculum aerophilum

<400> SEQUENCE: 19

```
Val Tyr Pro Lys Lys Thr His Trp Thr Ala Glu Ile Thr Pro Asn Leu
 1               5                  10                  15

His Gly Thr Glu Val Val Ala Gly Trp Val Trp Arg Leu Arg Asp
            20                  25                  30

Trp Gly Leu Ala Lys Thr Val Arg Val Lys Asp Arg Glu Gly Gly Ala
            35                  40                  45

Ser Val Arg Val Thr Leu Arg Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Trp Trp Val Trp Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 20
<211> LENGTH: 111
<212> TYPE: PRT
<213> ORGANISM: Pyrobaculum aerophilum

<400> SEQUENCE: 20

```
Val Tyr Pro Lys Lys Thr His Trp Thr Ala Glu Ile Thr Pro Asn Leu
 1               5                  10                  15

His Gly Thr Glu Val Val Ala Gly Trp Val Ser Cys Leu Cys Asp
            20                  25                  30

Ala Gly Lys Arg Lys Trp Val Tyr Val Val Asp Arg Glu Gly Gly Ala
            35                  40                  45

Pro Val Ala Val Arg Leu Arg Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Arg Ala Gly Ser Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 21
<211> LENGTH: 111
<212> TYPE: PRT
<213> ORGANISM: Pyrobaculum aerophilum

<400> SEQUENCE: 21

Val Tyr Pro Lys Lys Thr His Trp Thr Ala Glu Ile Thr Pro Asn Leu
1               5                   10                  15

His Gly Thr Glu Val Val Ala Gly Trp Val Ser Asp Leu Leu Asp
            20                  25                  30

Ala Gly Arg Ala Lys Tyr Val Phe Val Tyr Asp Arg Glu Gly Gly Ala
            35                  40                  45

Glu Val Met Val Thr Leu Ala Ala Gly Lys Thr Pro Asp His Leu Phe
50                  55                  60

Lys Val Phe Ala Glu Leu Ser Arg Glu Asp Val Val Ile Lys Gly
65                  70                  75                  80

Ile Val Glu Ala Ser Lys Gly Trp Arg Asp Gly Val Gly Ile Phe Pro
                85                  90                  95

Ser Glu Ile Trp Ile Leu Asn Lys Ala Lys Pro Leu Pro Ile Asp
            100                 105                 110

<210> SEQ ID NO 22
<211> LENGTH: 111
<212> TYPE: PRT
<213> ORGANISM: Pyrobaculum aerophilum

<400> SEQUENCE: 22

Val Tyr Pro Lys Lys Thr His Trp Thr Ala Glu Ile Thr Pro Asn Leu
1               5                   10                  15

His Gly Thr Glu Val Val Ala Gly Trp Val Ala Ser Leu Gly Asp
            20                  25                  30

Tyr Gly Arg Val Lys Ile Val Lys Val Ser Asp Arg Glu Gly Gly Ala
            35                  40                  45

Ala Val Pro Val Tyr Leu Glu Ala Gly Lys Thr Pro Asp His Leu Phe
50                  55                  60

Lys Val Phe Ala Glu Leu Ser Arg Glu Asp Val Val Ile Lys Gly
65                  70                  75                  80

Ile Val Glu Ala Ser Lys Gly Val Gly Arg Gly Val Gly Ile Phe Pro
                85                  90                  95

Ser Glu Ile Trp Ile Leu Asn Lys Ala Lys Pro Leu Pro Ile Asp
            100                 105                 110

<210> SEQ ID NO 23
<211> LENGTH: 111
<212> TYPE: PRT
<213> ORGANISM: Pyrobaculum aerophilum

<400> SEQUENCE: 23

Val Tyr Pro Lys Lys Thr His Trp Thr Ala Glu Ile Thr Pro Asn Leu
1               5                   10                  15

His Gly Thr Glu Val Val Ala Gly Trp Val Gly Glu Leu Ala Asp
            20                  25                  30

Phe Gly Asp Met Lys Thr Val Ala Val Arg Asp Arg Glu Gly Gly Ala
            35                  40                  45

Glu Val Pro Val Thr Leu Leu Ala Gly Lys Thr Pro Asp His Leu Phe
50                  55                  60

Lys Val Phe Ala Glu Leu Ser Arg Glu Asp Val Val Ile Lys Gly
65                  70                  75                  80

Ile Val Glu Ala Ser Lys Gly Ser Thr Ser Gly Val Glu Ile Phe Pro
                85                  90                  95

Ser Glu Ile Trp Ile Leu Asn Lys Ala Lys Pro Leu Pro Ile Asp
            100                 105                 110

<210> SEQ ID NO 24
<211> LENGTH: 111
<212> TYPE: PRT
<213> ORGANISM: Pyrobaculum aerophilum

<400> SEQUENCE: 24

```
Val Tyr Pro Lys Lys Thr His Trp Thr Ala Glu Ile Thr Pro Asn Leu
 1               5                   10                  15
His Gly Thr Glu Val Val Ala Gly Trp Val Ala Ser Leu Val Asp
                20                  25                  30
Gly Gly Pro Arg Lys Trp Val Phe Val Arg Asp Arg Glu Gly Gly Ala
            35                  40                  45
Glu Val Thr Val Glu Leu Thr Ala Gly Lys Thr Pro Asp His Leu Phe
 50                  55                  60
Lys Val Phe Ala Glu Leu Ser Arg Glu Asp Val Val Ile Lys Gly
 65                  70                  75                  80
Ile Val Glu Ala Ser Lys Gly Leu Arg Trp Gly Val Glu Ile Phe Pro
                85                  90                  95
Ser Glu Ile Trp Ile Leu Asn Lys Ala Lys Pro Leu Pro Ile Asp
            100                 105                 110
```

<210> SEQ ID NO 25
<211> LENGTH: 111
<212> TYPE: PRT
<213> ORGANISM: Pyrobaculum aerophilum

<400> SEQUENCE: 25

```
Val Tyr Pro Lys Lys Thr His Trp Thr Ala Glu Ile Thr Pro Asn Leu
 1               5                   10                  15
His Gly Thr Glu Val Val Ala Gly Trp Val Val Gly Leu Met Asp
                20                  25                  30
Glu Gly Ala Leu Lys Gly Val Glu Val Arg Asp Arg Glu Gly Gly Ala
            35                  40                  45
Pro Val Glu Val Thr Leu Glu Ala Gly Lys Thr Pro Asp His Leu Phe
 50                  55                  60
Lys Val Phe Ala Glu Leu Ser Arg Glu Asp Val Val Ile Lys Gly
 65                  70                  75                  80
Ile Val Glu Ala Ser Lys Gly Tyr Gly Ser Gly Val Glu Ile Phe Pro
                85                  90                  95
Ser Glu Ile Trp Ile Leu Asn Lys Ala Lys Pro Leu Pro Ile Asp
            100                 105                 110
```

<210> SEQ ID NO 26
<211> LENGTH: 111
<212> TYPE: PRT
<213> ORGANISM: Pyrobaculum aerophilum

<400> SEQUENCE: 26

```
Val Tyr Pro Lys Lys Thr His Trp Thr Ala Glu Ile Thr Pro Asn Leu
 1               5                   10                  15
His Gly Thr Glu Val Val Ala Gly Trp Val Val Asp Leu Val Asp
                20                  25                  30
Leu Gly Arg Asn Lys Leu Val Gln Val Ser Asp Arg Glu Gly Gly Ala
            35                  40                  45
Arg Val Leu Val Asn Leu Ala Ala Gly Lys Thr Pro Asp His Leu Phe
 50                  55                  60
```

```
Lys Val Phe Ala Glu Leu Ser Arg Glu Asp Val Val Ile Lys Gly
 65                  70                  75                  80

Ile Val Glu Ala Ser Lys Ile Gln Arg Ser Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 27
<211> LENGTH: 111
<212> TYPE: PRT
<213> ORGANISM: Pyrobaculum aerophilum

<400> SEQUENCE: 27

```
Val Tyr Pro Lys Lys Thr His Trp Thr Ala Glu Ile Thr Pro Asn Leu
 1                5                  10                  15

His Gly Thr Glu Val Val Ala Gly Trp Val Glu Asp Leu Val Asp
                 20                  25                  30

Ala Gly Lys Thr Lys Trp Val Phe Val Cys Asp Arg Glu Gly Gly Ala
            35                  40                  45

Gln Val Ile Val Glu Leu Val Ala Gly Lys Thr Pro Asp His Leu Phe
     50                  55                  60

Lys Val Phe Ala Glu Leu Ser Arg Glu Asp Val Val Ile Lys Gly
 65                  70                  75                  80

Ile Val Glu Ala Ser Lys Ser Arg Ala Val Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 28
<211> LENGTH: 111
<212> TYPE: PRT
<213> ORGANISM: Pyrobaculum aerophilum

<400> SEQUENCE: 28

```
Val Tyr Pro Lys Lys Thr His Trp Thr Ala Glu Ile Thr Pro Asn Leu
 1                5                  10                  15

His Gly Thr Glu Val Val Ala Gly Trp Val Thr Asp Leu Val Asp
                 20                  25                  30

Ala Gly Thr Trp Lys Phe Val Gln Val Ala Asp Arg Glu Gly Gly Ala
            35                  40                  45

Asn Val Trp Val Ser Leu Val Ala Gly Lys Thr Pro Asp His Leu Phe
     50                  55                  60

Lys Val Phe Ala Glu Leu Ser Arg Glu Asp Val Val Ile Lys Gly
 65                  70                  75                  80

Ile Val Glu Ala Ser Lys Leu Pro Ser Tyr Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 29
<211> LENGTH: 111
<212> TYPE: PRT
<213> ORGANISM: Pyrobaculum aerophilum

<400> SEQUENCE: 29

```
Val Tyr Pro Lys Lys Thr His Trp Thr Ala Glu Ile Thr Pro Asn Leu
 1                5                  10                  15
```

```
His Gly Thr Glu Val Val Ala Gly Trp Val Thr Asp Leu Val Asp
             20                  25                  30

Ala Gly Thr Trp Lys Phe Val Gln Val Ala Asp Arg Glu Gly Gly Ala
         35                  40                  45

Asn Val Trp Val Ser Leu Val Ala Gly Lys Thr Pro Asp His Leu Phe
 50                  55                  60

Lys Val Phe Ala Glu Leu Ser Arg Glu Asp Val Val Ile Lys Gly
 65                  70                  75                  80

Ile Val Glu Ala Ser Lys Pro Gly Ala Ala Gly Val Glu Ile Phe Pro
                 85                  90                  95

Ser Glu Ile Trp Ile Leu Asn Lys Ala Lys Pro Leu Pro Ile Asp
            100                 105                 110
```

<210> SEQ ID NO 30
<211> LENGTH: 31
<212> TYPE: DNA
<213> ORGANISM: Pyrobaculum aerophilum

<400> SEQUENCE: 30
caccagtgga tccgtgtatc ctaaaaagac c                              31

<210> SEQ ID NO 31
<211> LENGTH: 33
<212> TYPE: DNA
<213> ORGANISM: Pyrobaculum aerophilum

<400> SEQUENCE: 31
acccgggaat tctcagtcta ttggaagcgg ctt                            33

<210> SEQ ID NO 32
<211> LENGTH: 31
<212> TYPE: DNA
<213> ORGANISM: Pyrobaculum aerophilum

<400> SEQUENCE: 32
caccagtgga tccattgaga aattcacggc g                              31

<210> SEQ ID NO 33
<211> LENGTH: 33
<212> TYPE: DNA
<213> ORGANISM: Pyrobaculum aerophilum

<400> SEQUENCE: 33
acccgggaat tctcactatt taactctaat aat                            33

<210> SEQ ID NO 34
<211> LENGTH: 44
<212> TYPE: DNA
<213> ORGANISM: Pyrobaculum aerophilum

<400> SEQUENCE: 34
ggtgacctac catggcccag gtggtgtatc ctaaaaagac ccac                44

<210> SEQ ID NO 35
<211> LENGTH: 18
<212> TYPE: DNA
<213> ORGANISM: Pyrobaculum aerophilum

<400> SEQUENCE: 35
tacccaaccg gcaacaac                                             18

```
<210> SEQ ID NO 36
<211> LENGTH: 18
<212> TYPE: DNA
<213> ORGANISM: Pyrobaculum aerophilum

<400> SEQUENCE: 36
gttgttgccg gttgggta                                                 18

<210> SEQ ID NO 37
<211> LENGTH: 18
<212> TYPE: DNA
<213> ORGANISM: Pyrobaculum aerophilum

<400> SEQUENCE: 37 cgcgccccccc tccctatc                                                18

<210> SEQ ID NO 38
<211> LENGTH: 18
<212> TYPE: DNA
<213> ORGANISM: Pyrobaculum aerophilum

<400> SEQUENCE: 38
gatagggagg ggggcgcg                                                 18

<210> SEQ ID NO 39
<211> LENGTH: 18
<212> TYPE: DNA
<213> ORGANISM: Pyrobaculum aerophilum

<400> SEQUENCE: 39 atcggggggtt tttcccgc                                                18

<210> SEQ ID NO 40
<211> LENGTH: 18
<212> TYPE: DNA
<213> ORGANISM: Pyrobaculum aerophilum

<400> SEQUENCE: 40
gcgggaaaaa cccccgat                                                 18

<210> SEQ ID NO 41
<211> LENGTH: 18
<212> TYPE: DNA
<213> ORGANISM: Pyrobaculum aerophilum

<400> SEQUENCE: 41
tttactggcc tcaacaat                                                 18

<210> SEQ ID NO 42
<211> LENGTH: 18
<212> TYPE: DNA
<213> ORGANISM: Pyrobaculum aerophilum

<400> SEQUENCE: 42
attgttgagg ccagtaaa                                                 18

<210> SEQ ID NO 43
<211> LENGTH: 18
<212> TYPE: DNA
<213> ORGANISM: Pyrobaculum aerophilum

<400> SEQUENCE: 43
ggtgtggaga ttttcccc                                                 18
```

<210> SEQ ID NO 44
<211> LENGTH: 34
<212> TYPE: DNA
<213> ORGANISM: Pyrobaculum aerophilum

<400> SEQUENCE: 44 gagggggcg cgtttgtgca agtcacgctc aagg       34

<210> SEQ ID NO 45
<211> LENGTH: 36
<212> TYPE: DNA
<213> ORGANISM: Pyrobaculum aerophilum

<400> SEQUENCE: 45
ggagatagca acggcgcggt aattcagcta atggac       36

<210> SEQ ID NO 46
<211> LENGTH: 36
<212> TYPE: DNA
<213> ORGANISM: Pyrobaculum aerophilum

<400> SEQUENCE: 46
cgcgccgttg ctatctcctg aaacggagag tatttg       36

<210> SEQ ID NO 47
<211> LENGTH: 18
<212> TYPE: DNA
<213> ORGANISM: Pyrobaculum aerophilum

<400> SEQUENCE: 47
gtgccgatga aatacgtc       18

<210> SEQ ID NO 48
<211> LENGTH: 18
<212> TYPE: DNA
<213> ORGANISM: Pyrobaculum aerophilum

<400> SEQUENCE: 48
gacgtatttc atcggcac       18

<210> SEQ ID NO 49
<211> LENGTH: 18
<212> TYPE: DNA
<213> ORGANISM: Pyrobaculum aerophilum

<400> SEQUENCE: 49
cgcgccgttg ctatctcc       18

<210> SEQ ID NO 50
<211> LENGTH: 18
<212> TYPE: DNA
<213> ORGANISM: Pyrobaculum aerophilum

<400> SEQUENCE: 50
ggagatagca acggcgcg       18

<210> SEQ ID NO 51
<211> LENGTH: 18
<212> TYPE: DNA
<213> ORGANISM: Pyrobaculum aerophilum

<400> SEQUENCE: 51
atctcctgaa acggagag       18

```
<210> SEQ ID NO 52
<211> LENGTH: 18
<212> TYPE: DNA
<213> ORGANISM: Pyrobaculum aerophilum

<400> SEQUENCE: 52
tagctgaatt accgcgcc                                                 18

<210> SEQ ID NO 53
<211> LENGTH: 17
<212> TYPE: DNA
<213> ORGANISM: Pyrobaculum aerophilum

<400> SEQUENCE: 53
ctctccgttt caggaga                                                  17

<210> SEQ ID NO 54
<211> LENGTH: 18
<212> TYPE: DNA
<213> ORGANISM: Pyrobaculum aerophilum

<400> SEQUENCE: 54
ggcgcggtaa ttcagcta                                                 18

<210> SEQ ID NO 55
<211> LENGTH: 78
<212> TYPE: DNA
<213> ORGANISM: Pyrobaculum aerophilum
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 55
gttgccggtt gggtannknn kttgnnkgac nnkgggnnkn nkaagnnkgt gnnkgtgnnk   60
gatagggagg ggggcgcg                                                 78
```

<210> SEQ ID NO 56
<211> LENGTH: 57
<212> TYPE: DNA
<213> ORGANISM: Pyrobaculum aerophilum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 56
atcgggggtt tttcccgcmn ngagmnngac mnncacmnnc gcgccccccct ccctatc    57

<210> SEQ ID NO 57
<211> LENGTH: 48
<212> TYPE: DNA
<213> ORGANISM: Pyrobaculum aerophilum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 57
attgttgagg ccagtaaann knnknnknnk ggtgtggaga ttttcccc    48

<210> SEQ ID NO 58
<211> LENGTH: 75
<212> TYPE: DNA
<213> ORGANISM: Pyrobaculum aerophilum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature

```
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 58
tttatagtcg cgcatgtckn ntagknnaat knnatctcck nnaacknnkn ntatknncgc      60
cgtgaatttc tcaat                                                      75

<210> SEQ ID NO 59
<211> LENGTH: 45
<212> TYPE: DNA
<213> ORGANISM: Pyrobaculum aerophilum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 59
gacatgcgcg actataaann katannkgtg ccgatgaaat acgtc                     45

<210> SEQ ID NO 60
<211> LENGTH: 54
<212> TYPE: DNA
<213> ORGANISM: Pyrobaculum aerophilum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 60
attgagaaat tcacggcgnn katannknnk gttnnkggag atagcaacgg cgcg           54

<210> SEQ ID NO 61
<211> LENGTH: 75
<212> TYPE: DNA
<213> ORGANISM: Pyrobaculum aerophilum
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
```

```
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 61
gtatttcatc ggcacmnnta tmnntttmnn gtcgcgmnng tcmnntagmn naatmnncgc      60
gccgttgcta tctcc                                                      75

<210> SEQ ID NO 62
<211> LENGTH: 42
<212> TYPE: DNA
<213> ORGANISM: Pyrobaculum aerophilum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 62
ctctccgttt caggagatnn knnkggcgcg gtaattcagc ta                        42

<210> SEQ ID NO 63
<211> LENGTH: 42
<212> TYPE: DNA
<213> ORGANISM: Pyrobaculum aerophilum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 63
ctctccgttt caggagatnn knnkagcaac ggcgcggtaa tt                        42

<210> SEQ ID NO 64
<211> LENGTH: 172
<212> TYPE: PRT
<213> ORGANISM: Homo sapiens

<400> SEQUENCE: 64

Glu Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
                20                  25                  30

Val Arg Asp Leu Thr Ile Gln Lys Ala Asp Glu Val Val Trp Val Arg
            35                  40                  45

Ala Arg Val His Thr Ser Arg Ala Lys Gly Lys Gln Cys Phe Leu Val
        50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Ala Asn Ile Asn Lys Glu
                85                  90                  95
```

```
Ser Ile Val Asp Val Glu Gly Val Arg Lys Val Asn Gln Lys Ile
            100                 105                 110

Gly Ser Cys Thr Gln Gln Asp Val Glu Leu His Val Gln Lys Ile Tyr
            115                 120                 125

Val Ile Ser Leu Ala Glu Pro Arg Leu Pro Leu Gln Leu Asp Asp Ala
130                 135                 140

Val Arg Pro Glu Ala Glu Gly Glu Glu Gly Arg Ala Thr Val Asn
145                 150                 155                 160

Gln Asp Thr Arg Leu Asp Asn Arg Val Ile Asp Leu
                165                 170
```

<210> SEQ ID NO 65
<211> LENGTH: 178
<212> TYPE: PRT
<213> ORGANISM: Saccharomyces cerevisiae

<400> SEQUENCE: 65

```
Glu Lys Lys Ala Ala Ala Glu Asp Thr Ala Lys Asp Asn Tyr Gly Lys
1               5                   10                  15

Leu Pro Leu Ile Gln Ser Arg Asp Ser Asp Arg Thr Gly Gln Lys Arg
            20                  25                  30

Val Lys Phe Val Asp Leu Asp Glu Ala Lys Asp Ser Asp Lys Glu Val
        35                  40                  45

Leu Phe Arg Ala Arg Val His Asn Thr Arg Gln Gln Gly Ala Thr Leu
    50                  55                  60

Ala Phe Leu Thr Leu Arg Gln Gln Ala Ser Leu Ile Gln Gly Leu Val
65                  70                  75                  80

Lys Ala Asn Lys Glu Gly Thr Ile Ser Lys Asn Met Val Lys Trp Ala
                85                  90                  95

Gly Ser Leu Asn Leu Glu Ser Ile Val Leu Val Arg Gly Ile Val Lys
            100                 105                 110

Lys Val Asp Glu Pro Ile Lys Ser Ala Thr Val Gln Asn Leu Glu Ile
        115                 120                 125

His Ile Thr Lys Ile Tyr Thr Ile Ser Glu Thr Pro Glu Ala Leu Pro
    130                 135                 140

Ile Leu Leu Glu Asp Ala Ser Arg Ser Glu Ala Glu Ala Glu Ala Ala
145                 150                 155                 160

Gly Leu Pro Val Val Asn Leu Asp Thr Arg Leu Asp Tyr Arg Val Ile
                165                 170                 175

Asp Leu
```

<210> SEQ ID NO 66
<211> LENGTH: 120
<212> TYPE: PRT
<213> ORGANISM: Arabidopsis thialana

<400> SEQUENCE: 66

```
Ser Asn Leu Val Glu Glu Ile Val Gly Ser Glu Val Ser Ile Arg Gly
1               5                   10                  15

Arg Leu His Lys Asn Arg Leu Val Gly Thr Lys Leu Phe Val Ile Leu
            20                  25                  30

Arg Glu Ser Gly Phe Thr Val Gln Cys Val Val Glu Glu Thr Arg Val
        35                  40                  45

Gly Ala Asn Met Ile Lys Phe Val Lys Gln Leu Ser Arg Glu Ser Val
    50                  55                  60
```

```
Val Glu Leu Ile Gly Val Ser His Pro Lys Pro Leu Thr Gly
 65                  70                  75                  80

Thr Thr Gln Gln Val Glu Ile His Val Arg Lys Met Tyr Cys Leu Ser
                 85                  90                  95

Arg Ser Leu Pro Asn Leu Pro Leu Val Val Glu Asp Ala Ala Arg Ser
            100                 105                 110

Glu Ser Asp Ile Glu Lys Ser Gly
        115                 120

<210> SEQ ID NO 67
<211> LENGTH: 128
<212> TYPE: PRT
<213> ORGANISM: Pyrobaculum aerophilum

<400> SEQUENCE: 67

Met Tyr Pro Lys Lys Thr His Trp Thr Ala Glu Ile Thr Pro Asn Leu
1               5                   10                  15

His Gly Thr Glu Val Val Val Ala Gly Trp Val Trp Glu Leu Arg Asp
            20                  25                  30

Ile Gly Arg Val Lys Phe Val Val Arg Asp Arg Glu Gly Phe Val
        35                  40                  45

Gln Val Thr Leu Lys Ala Gly Lys Thr Pro Asp His Leu Phe Lys Val
    50                  55                  60

Phe Ala Glu Leu Ser Arg Glu Asp Val Val Ile Lys Gly Ile Val
65                  70                  75                  80

Glu Ala Ser Lys Ile Ala Lys Ser Gly Val Glu Ile Phe Pro Ser Glu
                85                  90                  95

Ile Trp Ile Leu Asn Lys Ala Lys Pro Leu Pro Ile Asp Ile Trp Ser
            100                 105                 110

Glu Thr Pro Asp Leu Ala Thr Arg Leu Lys Trp Arg Ser Val Asp Leu
        115                 120                 125

<210> SEQ ID NO 68
<211> LENGTH: 129
<212> TYPE: PRT
<213> ORGANISM: Escherichia coli

<400> SEQUENCE: 68

Met Arg Thr Glu Tyr Cys Gly Gln Leu Arg Leu Ser His Val Gly Gln
1               5                   10                  15

Gln Val Thr Leu Cys Gly Trp Val Asn Arg Arg Arg Asp Leu Gly Ser
            20                  25                  30

Leu Ile Phe Ile Asp Met Arg Asp Arg Glu Gly Ile Val Gln Val Phe
        35                  40                  45

Phe Asp Pro Asp Arg Ala Asp Ala Leu Lys Leu Ala Ser Glu Leu Arg
    50                  55                  60

Asn Glu Phe Cys Ile Gln Val Thr Gly Thr Val Arg Ala Arg Asp Glu
65                  70                  75                  80

Lys Asn Ile Asn Arg Asp Met Ala Thr Gly Glu Ile Glu Val Leu Ala
                85                  90                  95

Ser Ser Leu Thr Ile Ile Asn Arg Ala Asp Val Leu Pro Leu Asp Ser
            100                 105                 110

Asn His Val Asn Thr Glu Glu Ala Arg Leu Lys Tyr Arg Tyr Leu Asp
        115                 120                 125

Leu
```

-continued

<210> SEQ ID NO 69
<211> LENGTH: 71
<212> TYPE: PRT
<213> ORGANISM: Homo sapiens

<400> SEQUENCE: 69

```
Ile Lys Arg Asn Asp Phe Gln Leu Ile Gly Ile Gln Asp Gly Tyr Leu
1               5                  10                  15

Ser Leu Leu Gln Asp Ser Gly Glu Val Arg Glu Asp Leu Arg Leu Pro
            20                  25                  30

Glu Gly Asp Leu Gly Lys Glu Ile Glu Gln Lys Tyr Asp Cys Gly Glu
        35                  40                  45

Glu Ile Leu Ile Thr Val Leu Ser Ala Met Thr Glu Glu Ala Ala Val
    50                  55                  60

Ala Ile Lys Ala Met Ala Lys
65                  70
```

<210> SEQ ID NO 70
<211> LENGTH: 73
<212> TYPE: PRT
<213> ORGANISM: Saccharomyces cerevisiae

<400> SEQUENCE: 70

```
Val Lys Arg Ser Glu Tyr Gln Leu Leu Asp Ile Asp Asp Gly Tyr Leu
1               5                  10                  15

Ser Leu Met Thr Met Asp Gly Glu Thr Lys Asp Asp Val Lys Ala Pro
            20                  25                  30

Glu Gly Glu Leu Gly Asp Ser Met Gln Ala Ala Phe Asp Glu Gly Lys
        35                  40                  45

Asp Leu Met Val Thr Ile Ile Ser Ala Met Gly Glu Glu Ala Ala Ile
    50                  55                  60

Ser Phe Lys Glu Ala Pro Arg Ser Asp
65                  70
```

<210> SEQ ID NO 71
<211> LENGTH: 63
<212> TYPE: PRT
<213> ORGANISM: Pyrobaculum aerophilum

<400> SEQUENCE: 71

```
Ile Glu Lys Phe Thr Ala Gln Ile Leu Ser Val Ser Gly Asp Val Ile
1               5                  10                  15

Gln Leu Met Asp Met Arg Asp Tyr Lys Thr Ile Glu Val Pro Met Lys
            20                  25                  30

Tyr Val Glu Glu Glu Ala Lys Gly Arg Leu Ala Pro Gly Ala Glu Val
        35                  40                  45

Glu Val Trp Gln Ile Leu Asp Arg Tyr Lys Ile Ile Arg Val Lys
    50                  55                  60
```

<210> SEQ ID NO 72
<211> LENGTH: 103
<212> TYPE: PRT
<213> ORGANISM: Pyrobaculum aerophilum

<400> SEQUENCE: 72

```
Pro Lys Lys Thr His Trp Thr Ala Glu Ile Thr Pro Asn Leu His Gly
1               5                  10                  15

Thr Glu Val Val Val Ala Gly Trp Val Trp Glu Leu Arg Asp Ile Gly
            20                  25                  30
```

Arg Val Lys Phe Val Val Arg Asp Arg Glu Gly Phe Gln Val
         35                  40                 45

Thr Leu Lys Ala Gly Lys Thr Pro Asp His Leu Phe Lys Val Phe Ala
 50                      55                  60

Glu Leu Ser Arg Glu Asp Val Val Ile Lys Gly Ile Val Glu Ala
 65                  70                  75                  80

Ser Lys Ile Ala Lys Ser Gly Val Glu Ile Phe Pro Ser Glu Ile Trp
                 85                  90                  95

Ile Leu Asn Lys Ala Lys Pro
              100

<210> SEQ ID NO 73
<211> LENGTH: 95
<212> TYPE: PRT
<213> ORGANISM: Pyrococcus kodakaraensis

<400> SEQUENCE: 73

Met Tyr Arg Thr His Tyr Ser Ser Glu Ile Thr Glu Glu Leu Asn Gly
 1               5                  10                  15

Gln Lys Val Lys Val Ala Gly Trp Val Trp Glu Val Lys Asp Leu Gly
                 20                  25                  30

Gly Ile Lys Phe Leu Trp Ile Arg Asp Arg Asp Gly Ile Val Gln Ile
             35                  40                  45

Thr Ala Pro Lys Lys Val Asp Pro Glu Leu Phe Lys Leu Ile Pro
 50                  55                  60

Lys Leu Arg Ser Glu Asp Val Val Ala Val Gly Val Val Asn Phe
 65                  70                  75                  80

Thr Pro Lys Ala Lys Lys Ile Val Val Leu Asn Arg Ala Glu Thr
             85                  90                  95

<210> SEQ ID NO 74
<211> LENGTH: 107
<212> TYPE: PRT
<213> ORGANISM: Escherichia coli

<400> SEQUENCE: 74

Met Arg Thr Glu Tyr Cys Gly Gln Leu Arg Leu Ser His Val Gly Gln
 1               5                  10                  15

Gln Val Thr Leu Cys Gly Trp Val Asn Arg Arg Arg Asp Leu Gly Ser
                 20                  25                  30

Leu Ile Phe Ile Asp Met Arg Asp Arg Glu Gly Ile Val Gln Val Phe
             35                  40                  45

Phe Asp Pro Asp Arg Ala Asp Ala Leu Lys Leu Ala Ser Glu Leu Arg
 50                  55                  60

Asn Glu Phe Cys Ile Gln Val Thr Gly Thr Val Arg Ala Arg Asp Glu
 65                  70                  75                  80

Lys Asn Ile Asn Arg Asp Met Ala Thr Gly Glu Ile Glu Val Leu Ala
             85                  90                  95

Ser Ser Leu Thr Ile Ile Asn Arg Ala Asp Val
             100                 105

<210> SEQ ID NO 75
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: Variant
<222> LOCATION: (1)
<223> OTHER INFORMATION: Xaa is Arg or Lys

<400> SEQUENCE: 75

Xaa Gly Cys Arg
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Construct

<400> SEQUENCE: 76

Lys Ala Phe Arg
1

<210> SEQ ID NO 77
<211> LENGTH: 4
<212> TYPE: PRT
<213> ORGANISM: Artificial Sequence
<220> FEATURE:
<223> OTHER INFORMATION: Synthetic Construct

<400> SEQUENCE: 77

Lys Cys Ala Trp
1

<210> SEQ ID NO 78
<211> LENGTH: 4
<212> TYPE: PRT
<213> ORGANISM: Artificial Sequence
<220> FEATURE:
<223> OTHER INFORMATION: Synthetic Construct

<400> SEQUENCE: 78

Ala Arg Arg Val
1

<210> SEQ ID NO 79
<211> LENGTH: 4
<212> TYPE: PRT
<213> ORGANISM: Artificial Sequence
<220> FEATURE:
<223> OTHER INFORMATION: Synthetic Construct

<400> SEQUENCE: 79

Ser Asn Gly Ala
1

<210> SEQ ID NO 80
<211> LENGTH: 4
<212> TYPE: PRT
<213> ORGANISM: Artificial Sequence
<220> FEATURE:
<223> OTHER INFORMATION: Synthetic Construct

<400> SEQUENCE: 80

Glu Thr Glu Thr
1

<210> SEQ ID NO 81
<211> LENGTH: 4
<212> TYPE: PRT
<213> ORGANISM: Artificial Sequence
<220> FEATURE:

```
<223> OTHER INFORMATION: Synthetic Construct

<400> SEQUENCE: 81

Pro Glu Thr Glu
1
```

OB FOLD DOMAINS

CROSS-REFERENCE TO RELATED APPLICATIONS

This application is a National Phase application under 35 USC §371 of International Application No. PCT/NZ2007/000125 filed May 25, 2007 and claims the priority benefit of U.S. Provisional Patent Application No. 60/809,105, filed May 26, 2006, entitled "OB Fold Domains," each of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 674612000300SeqList.txt, date recorded: Mar. 30, 2015, size: 49 KB).

BACKGROUND OF THE INVENTION

Molecular recognition is central to biological processes, from high-affinity protein-ligand interactions to the more transient protein-protein recognition events of signal transduction pathways. Such events depend on the versatility of proteins, which have been adapted to new roles as organisms have evolved. As an example, to capture a foreign antigen, a small number of antibodies from the immune system's naïve library (which contains approximately $10^7$ variants) (1) recognize the antigen and bind to it with moderate affinity. Selection and maturation then introduces further mutations to generate the tight, highly specific binding required to eliminate the antigen. In this way a staggering array of binding modes can be grafted on to the basic antibody scaffold, to sequester targets varying from small molecules to whole cells.

This strategy can be replicated in the laboratory to produce very large libraries of antibody variants (>$10^{10}$ different clones) (2,3) that can then be selected for binding to a particular target. Repeated cycles of amplification and selection for binding can then "discover" the test-tube antibodies with tight and specific molecular binding characteristics. This in vitro approach can also be applied to other scaffolds. For example, randomization and selection by phage display have been used to study and improve the binding of growth hormone and the growth factor heregulin to their respective receptors (4,5), and "affibodies" have been developed from libraries of a three-helix bundle domain from staphylococcal protein A (6,7). This general area has been the subject of several reviews (8-10).

OB-fold domains are generally small structural motifs found in a variety of proteins and originally named for their oligonucleotide/oligosaccharide binding properties. The OB-fold domain is a five-stranded closed b barrel and the majority of OB-fold domains proteins use the same face for ligand binding or an as active site. Different OB-fold domains use this "fold-related binding face" to bind oligosaccharides, oligonucleotides, proteins metal ions and catalytic substrates. OB-fold domains are described in for example, Arcus, *Curr. Opin. Strict. Biol.*, Vol. 12: 794-801 (2002) and Theobald, *Annu. Rev. Biophys. Biomol. Struct.*, Vol., 32: 115-33 (2003). Canadian Patent Publication No. 2,378,871 describes beta-pleated sheet proteins with binding properties.

The disclosure of all patents, patent applications, patent application publications, scientific publications and other publications cited herein are hereby incorporated by reference in their entirety.

BRIEF SUMMARY OF THE INVENTION

The invention provides for modified OB-fold domains having desired properties and methods of producing libraries of modified OB-fold domains. The invention also provides for the libraries of modified OB-fold domains produced by such methods and methods for screening such libraries of modified OB-fold domains for desired biological activities. In addition, the invention provides for the modified OB-fold domains identified from such libraries. Also provided herein are modified OB-fold domains obtainable from *Pyrobaculum aerophilum* that exhibit modified binding interactions. A modified OB-fold domain can bind to the same substrate as compared to the naturally-occurring OB-fold domain, or can bind to a different substrate as compared to the naturally-occurring OB-fold domain, or can bind to both the same substrate and a different substrate as compared to the naturally-occurring OB-fold domain. Alternatively, a modified OB-fold domain can be prepared where no known substrate binds to the naturally-occurring OB-fold domain, where the modified OB-fold domain binds to a substrate.

Thus, in one aspect, the invention is an isolated modified OB-fold domain, obtainable from a naturally occurring OB-fold domain, wherein the modified OB-fold domain comprises a) at least one modified amino acid residue in a β-strand of the OB-fold domain binding face as compared to the naturally occurring OB-fold domain, or b) at least one modified amino acid residue in a β-strand of the OB-fold domain binding face and at least one modified amino acid residue in a strand of the OB-fold domain loop region, or c) at least one modified amino acid residue in a strand of the OB-fold domain loop region, and wherein said modified OB-fold domain has altered binding characteristics as compared to the naturally occurring OB-fold domain. In one embodiment, where a binding partner of a naturally-occurring OB-fold domain is known, the invention is a modified OB-fold domain wherein the domain specifically binds to a different binding partner than the naturally occurring OB-fold domain or has modified binding with its naturally occurring binding partner. In another embodiment, the modified binding comprises about at least a 25%, about a 50%, or about a 75% reduction in the dissociation constant of the modified OB-fold domain with its naturally occurring binding partner, as compared to the corresponding naturally occurring OB-fold domain. In another embodiment, the modified binding comprises a decrease in the dissociation constant by a factor of at least about 2, about 3, about 4, about 5, about 6, about 8, about 10, about 15, about 20, about 25, about 50, about 100, about 200, about 500, about 1000, about 5000, about 10,000, about 50,000, or about 100,000 of the modified OB-fold domain with its naturally occurring binding partner, as compared to the corresponding naturally occurring OB-fold domain. In another embodiment, the invention is a modified OB-fold domain wherein the naturally occurring OB-fold domain occurs in a protein or class of proteins selected from the group consisting of Staphylococcal nuclease proteins; Bacterial enterotoxins; TIMP-like proteins; Heme chaperone CcmE protein; Tail-associated lysozyme gp5, N terminal domain protein; nucleic acid-binding proteins; inorganic pyrophosphatase; Mop-like proteins; CheW like proteins; tRNA_anti (OB-fold nucleic acid binding domain); Telo_bind (telomere-binding protein alpha subunit, central domain); SSB (single-stranded binding protein family OB-fold domain); DUF338 OB-fold domain; DNA_ligase_aden_(NAD-dependent DNA ligase OB-fold domain); Stap-Strp-toxin (Staphylococcal/ Streptococcal toxin, OB-fold domain); EIF-5a (Eucaryotic initiation factor 5A hypusine, DNA-binding OB-fold domain); GP5_OB (GP5 N-terminal OB-fold domain); CSD; DNA_ligase_OB; DUF388, EFP; eIF-1a; mRNA_cap_C; OB_RNB; Phage_DNA_bind; Rep-A_N; Rho_RNA_bind; Ribosomal_L2; Ribosomal_S12; Ribosomal_S17; RNA_pol_Rpb8; RuvA_N; S1; TOBE; TOBE_2; and tRN-A_bind. In another embodiment, the invention is a modified OB-fold domain wherein the naturally occurring OB-fold domain is from a thermophilic organism. In yet another embodiment, the invention is a modified OB-fold domain wherein the thermophilic organism is Pyrobaculum aerophilum. In another embodiment, the invention is a modified OB-fold domain wherein the modified amino acid residue is in a β-strand of the binding face.

The binding partner of a modified OB-fold domain may be selected from the group consisting of nucleic acids, oligosaccharides, proteins, hormones, and small organic molecules.

In another aspect, the invention is a method of obtaining a modified OB-fold domain comprising a) obtaining nucleic acid encoding a naturally occurring OB-fold domain, or encoding a portion thereof comprising a strand of the binding face and/or a strand of the loop, and b) altering the nucleic acid such that it encodes at least one modified amino acid residue on a β-strand of the binding face and/or at least one modified amino acid residue on a strand of a loop as compared to the naturally occurring OB-fold domain, wherein a modified OB-fold domain is obtained and wherein the modified OB-fold domain has altered binding as compared to the naturally occurring OB-fold domain. In another embodiment, where a binding partner of a naturally-occurring OB-fold domain is known, the modified binding comprises at least about a 25%, about a 50%, or about a 75% reduction in the dissociation constant of the modified OB-fold domain with its naturally occurring binding partner, as compared to the corresponding naturally occurring OB-fold domain. In another embodiment, the modified binding comprises a decrease in the dissociation constant by a factor of at least about 2, about 3, about 4, about 5, about 6, about 8, about 10, about 15, about 20, about 25, about 50, about 100, about 200, about 500, about 1000, about 5000, about 10,000, about 50,000, or about 100,000 of the modified OB-fold domain with its naturally occurring binding partner, as compared to the corresponding naturally occurring OB-fold domain. In one embodiment, the method further comprises altering nucleic acid encoding the modified OB-fold domain, and/or altering nucleic acid encoding at least one amino acid of a protein that comprises the modified OB-fold domain.

In another aspect, the invention provides for a method of producing a library of modified OB-fold domain proteins for display comprising a) obtaining nucleic acid encoding an OB-fold domain, or a portion thereof, and b) subjecting the nucleic acid to random alterations, thereby producing a collection of altered nucleic acid encoding modified OB-fold domains having at least one randomized amino acid residue. In one embodiment, the invention provides for a method of producing a library of modified OB-fold domain proteins for display wherein the nucleic acid encodes at least one amino acid residue of a strand of the OB-fold domain binding face and/or a strand of an OB-fold domain loop. In another embodiment, the method further comprises placing the library of altered nucleic acid encoding modified OB fold domains into a population of host cells or viral particles capable of displaying said modified OB-fold domains on their surface.

In another aspect, the invention provides for an isolated nucleic acid encoding the modified OB-fold domain obtainable from a naturally occurring OB-fold domain, wherein said modified OB-fold domain comprises a) at least one modified amino acid residue in a β-strand of the OB-fold domain binding face as compared to the naturally occurring OB-fold domain, or b) at least one modified amino acid residue in a β-strand of the OB-fold domain binding face and at least one modified amino acid residue in a strand of the OB-fold domain loop region, or c) at least one modified amino acid residue in a strand of the OB-fold domain loop region, and wherein said modified OB-fold domain has altered binding characteristics as compared to the naturally occurring OB-fold domain. In another embodiment, where a binding partner of a naturally-occurring OB-fold domain is known, the altered binding characteristics comprise at least about a 25%, about a 50%, or about a 75% reduction in the dissociation constant of the modified OB-fold domain with its naturally occurring binding partner, as compared to the corresponding naturally occurring OB-fold domain. In another embodiment, the altered binding characteristics comprise a decrease in the dissociation constant by a factor of at least about 2, about 3, about 4, about 5, about 6, about 8, about 10, about 15, about 20, about 25, about 50, about 100, about 200, about 500, about 1000, about 5000, about 10,000, about 50,000, or about 100,000 of the modified OB-fold domain with its naturally occurring binding partner, as compared to the corresponding naturally occurring OB-fold domain.

In another aspect, the invention provides for a host cell or viral particle comprising nucleic acid encoding the nucleic acid of the modified OB-fold domain described above. In yet another aspect, the invention provides for a composition comprising nucleic acid encoding the nucleic acid of the modified OB-fold domain described above.

In another aspect, the invention provides for a method of screening a library of modified OB-fold domains for binding with a binding partner, comprising a) obtaining a population of host cells or viral particles displaying a library of modified OB-fold domains on their surface; b) contacting the population of host cells or viral particles with the binding partner under conditions suitable for binding of the binding partner to the modified OB-fold domain; and c) determining binding of the binding partner to the modified OB-fold domain. In one embodiment, the host cells or viral particles are phage that display the modified OB-fold domains on their surface.

In another aspect, the invention provides for a phage library of modified OB-fold domains, wherein the modified OB-fold domains are obtainable from Pyrobaculum aerophilum.

In another aspect, the invention provides for a modified OB-fold domain displayed on the surface of a cell or viral particle. In one embodiment, the cell or viral particle is a phage, bacteria or yeast.

In another aspect, the invention provides for a modified OB-fold domain attached to a solid support. In one embodiment, the support is selected from the group consisting of beads, glass, slides, chips, and gelatin.

In another aspect, the invention provides modified OB-fold domain proteins having the sequences listed in Appendix II and of the designation U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44. In another aspect, the invention provides proteins having about 90%, about 95%, about 98%, or about 99% sequence homology to the sequences listed in Appendix II and of the designation U1, U2, U3, U4, U5, U6, U7, U8, U9, S68, S81, pMB 16, pMB 17, pMB12, pMB18, pMB15, D05, D07, D09, D04, L14, L8, L4, L16, L34, L42, L6, L5, or L44. In another aspect, the invention provides proteins having about 90%, about 95%, about 98%, or about 99% sequence identity to the sequences listed in Appendix II and of the designation U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44. In all of the above aspects, the protein can be isolated, purified, or isolated and purified.

In another aspect the invention provides a nucleic acid encoding the protein specified by the sequences listed in Appendix II and of the designation U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44. In another aspect the invention provides a nucleic acid encoding a protein having about 90%, about 95%, about 98%, or about 99% sequence homology to the sequences listed in Appendix II and of the designation U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44. In another aspect the invention provides a nucleic acid encoding a protein having about 90%, about 95%, about 98%, or about 99% sequence identity to the sequences listed in Appendix II and of the designation U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44. In all of the above aspects, the nucleic acid can be isolated, purified, or isolated and purified.

BRIEF DESCRIPTION OF THE DRAWINGS

FIG. 1A illustrates the concave binding face. FIG. 1B is the schematic structure with beta sheets and loops labelled along with the N- and C-termini. $b2$, $b4$ and $b5$ are interrupted $b$-strands and have bulges or loops between their components. FIG. 1C is the corresponding topology diagram for this protein (24). Residues are shown as circles and hydrogen bonds are shown as dotted lines. Loops are labelled and the shear number, S, is indicated.

FIG. 2A shows the secondary structure elements for aspRS-OB as indicated in boxes above the oligonucleotides. Arrows and numbers below indicate primers used. Crosses indicate the randomized codons. Fragments 1-4 are assembled in the second PCR step. In this figure the assembly of the 13mRL library is shown (also see Table 4). FIG. 2B shows the overview of oligonucleotides used for library construction of IF5A-OB. The assembly of the different libraries is performed in three independent ways for 11 m, 9m, 2RL and 2RL+2 libraries. Symbols are as in FIG. 2A.

FIGS. 5A-5C show the sequence alignment of aspRS OB fold domains from different species. FIG. 5A (SEQ ID NOS: 64-68) shows the secondary structure of the OB fold (indicated below the sequence) and β-strands are labeled. Residues with arrows are conserved residues on the binding face and have been randomized in some libraries. Note that the human and yeast sequences have long N-termini and do not start at residue 1 in each case. Numbers at right indicate amino acid positions in each protein. FIG. 5B (SEQ ID NOS:69-71) shows the sequence alignment of IF-5A OB fold domains from different species. FIG.5C (SEQ ID NOS:72-74) shows the sequence alignment of aspRS-OB from *P aerophilum* (P.a.), *Pyrococcus kodakaraensis* (*P. kodak.*) and *Escherichia Coli* (*E. coli*). Sequence identities are indicated by asterisks. The secondary structure of the OB-fold is indicated below the sequence: 1=loop between strands 4 and 5, loop 4/5.

FIG. 6 is a schematic drawing of pRPSP2 used for phage display of aspRS-OB and derivatives. Shown are phage shock promotor (psp), pelB leader sequence, cloning site which contains the NcoI/NotI restriction sites, c-myc tag used for Western analysis and the gIII gene encoding the pIII protein. Phage displayed fusion proteins consist of the gene product of inserted gene into cloning site, the c-myc tag and pIII protein. pRPSP2 also contains a beta-lactamase gene for selection on ampicillin (not shown in FIG. 6).

FIG. 10 is a summary of sequence analysis of selected clones from OBRL selected on asp-tRNA (SEQ ID NOS:12-16, 67 and 76-78). Out of 12 clones, 10 contained an R or K in the first position, 7 a G in pos. 2, 8 a C in pos. 3, and 6 an R in pos. 4. A consensus sequence was suggested to be R/K G C R (SEQ ID NO:75).

FIG. 12 is a summary of sequences from aspRS-OB libraries before and after selection (SEQ ID NOS:1-13 and 17-29). A. Before selection, U1-U6 derived from 13mRL library, U8, U9 from RL library. B. Soluble unselected mutants from 13mRL. C. Mutants from RL selected on asp-tRNA. D. Mutants from 13mRL selected on asp-tRNA. E. Mutants 13mRL selected on lysozyme. The asp-OB wild type sequence is given at the top with corresponding residue number and localisation.

FIG. 15A: Mutants were immobilised as GST-fusions on glutathione beads and incubated with lysozyme. After washing, beads were analysed on SDS-PAGE. Lane 1: 13mRL81 (unselected mutant, negative control), 2: L5, 3: L16, 4: L4 (L18), 5: L8 (L21), 6: beads only (double negative control). FIG. 15B: L6 (soluble fraction in lane 1) was immobilised and incubated with lysozyme in same way as above. Beads were loaded and analysed on gel after washing with TBS (lane 2), TBS-T (lane 3), TBS-T 500 mM NaCl (lane 4).

BRIEF DESCRIPTION OF SEQUENCE LISTING

Figure 1A:
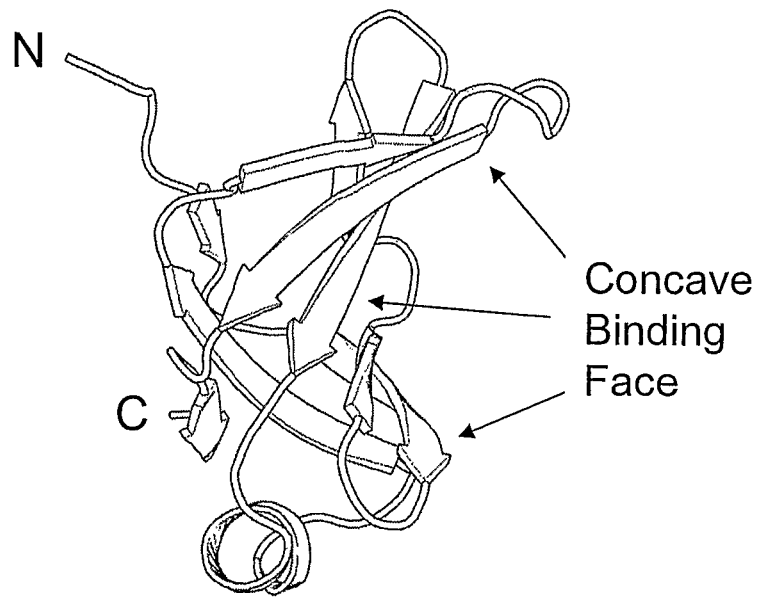
FIGS. 1A-1C show an OB-fold domain from the Streptococcal superantigen SMEZ-2 (25).

| Sequence ID No. | Sequence Name |
| --- | --- |
| 1. | U1 |
| 2. | U2 |
| 3. | U3 |
| 4. | U4 |
| 5. | U5 |
| 6. | U6 |
| 7. | U7 |
| 8. | U8 |
| 9. | U9 |
| 10. | S68 |
| 11. | S81 |
| 12. | pMB16 |
| 13. | pMB17 |
| 14. | pMB12 |
| 15. | pMB18 |
| 16. | pMB15 |
| 17. | D05 |
| 18. | D07 |
| 19. | D09 |
| 20. | D04 |
| 21. | L14 |
| 22. | L8 |
| 23. | L4 |
| 24. | L16 |
| 25. | L34 |
| 26. | L42 |
| 27. | L6 |
| 28. | L5 |
| 29. | L44 |
| 30. | Oligo 005 |
| 31. | Oligo 006 |
| 32. | Oligo 011 |
| 33. | Oligo 012 |
| 34. | Oligo 050 |
| 35. | Oligo 054 |
| 36. | Oligo 055 |
| 37. | Oligo 056 |
| 38. | Oligo 057 |
| 39. | Oligo 058 |
| 40. | Oligo 059 |
| 41. | Oligo 060 |
| 42. | Oligo 061 |
| 43. | Oligo 062 |
| 44. | Oligo 068 |
| 45. | Oligo 028 |
| 46. | Oligo 029 |
| 47. | Oligo 032 |
| 48. | Oligo 033 |
| 49. | Oligo 034 |
| 50. | Oligo 035 |
| 51. | Oligo 074 |
| 52. | Oligo 076 |
| 53. | Oligo 078 |
| 54. | Oligo 089 |
| 55. | Oligo 051 |
| 56. | Oligo 052 |
| 57. | Oligo 053 |
| 58. | Oligo 018 |
| 59. | Oligo 019 |
| 60. | Oligo 030 |
| 61. | Oligo 031 |
| 62. | Oligo 073 |
| 63. | Oligo 075 |

DETAILED DESCRIPTION OF THE INVENTION

The inventors discovered that "OB-fold domain(s)" or "OB-fold(s)" or "OB-fold protein domain(s)", which were originally named for their observed oligosaccharide-oligonucleotide binding properties, can be used as molecular recognition domains or scaffolds for producing modified OB-fold domains, and for creating libraries of modified OB fold domains which can be screened for desired biological activities, such as for example, binding to desired targets, and altered enzymatic properties. While the OB-fold domain was originally named for its oligosaccharide-oligonucleotide binding properties, it has since been observed at protein-protein interfaces as well (Theobald at al., *Annu. Rev. Biophys. Biomol. Struct.*, Vol. 32:115-33 (2003)). Accordingly, the present invention relates, in part, to the use of OB-fold domains, or portions thereof, in methods of producing modified OB-fold domains having desired properties; methods of producing libraries of modified OB-fold domains; the libraries of modified OB-fold domains produced by such methods; methods for screening such libraries of modified OB-fold domains for desired biological activities; and the modified OB-fold domains identified from such libraries. For example, such libraries of modified OB-fold domains can be screened for modified OB fold domains, or portions thereof, having increased or decreased binding interactions with a particular target(s) of interest, such as for example, a nucleotide, protein, or carbohydrate; or increased or decreased enzymatic activity.

In illustrative examples disclosed herein, the inventors have demonstrated production of a phage display library of modified OB-fold domains based on the tRNA anticodon binding domain of Aspartate tRNA Synthetase (AspRS) from *Pyrobaculum aerophilum*; stability of the AspRS modified OB-fold domains produced; and proper folding of AspRS modified OB-fold domains produced. In illustrative examples disclosed herein, the inventors have demonstrated the functional display of AspRS modified OB-fold domains on the surface of phage, thus allowing for screening of the library for modified OB-fold domains having desired properties. As demonstrated herein, the inventors were able to produce, screen for and select a modified AspRS OB fold domain that was converted from a nucleic acid binding domain, in its naturally occurring state, into a lysozyme protein binding molecule by using the compositions and methods disclosed herein. In other illustrative embodiments disclosed herein, the initiation factor IF-5A from *Pyrobaculum aerophilum* which contains an OB-fold domain was used to produce libraries of modified OB-fold domains.

The discovery that OB-fold domains of proteins can be used as a platform for producing modified OB-fold domains or libraries of modified OB-fold domains and screening for molecular recognition events has applications in diagnostic and therapeutic methods and, as described herein, has advantages over approaches known in the art using antibodies or other protein scaffolds. As will be understood by one of skill in the art, the methods disclosed herein for preparation of a library of modified OB-fold domains of AspRS or IF5A from *Pyrobaculum aerophilum* can be applied to other OB-fold domains described herein and known in the art. As will be understood by the skilled artisan, additional display and screening methods known in the art can be used to identify modified OB-fold domains having desired properties. It is also contemplated that the modified OB-fold domains could be attached to fixed and/or solid surfaces and used to screen for binding interactions. For example, OB-fold proteins can be covalently coupled to a fixed surface, or could be bound to a surface using an affinity tag (e.g., a 6×His tag). Methods of covalently coupling proteins to a surface are known by those of skill in the art, and affinity tags that can be used to affix proteins to a surface are known by those of skill in the art. Further, OB-fold proteins can be coupled to a solid surface, including but not limited to, beads, glass, slides, chips and gelatin. Thus, a series of OB-fold proteins can be used to make an array on a solid surface using techniques known to those of skill in the art. For example, U.S. Patent Application Publication No. 2004/0009530 discloses methods to prepare arrays.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993); and Gennaro, et al. 2000, *Remington: the Science and Practice of Pharmacy*, $20^{th}$ Ed. Lipincott Williams and Wilkins: Baltimore, Md.

Definitions

As used herein, the term "comprising" and its cognates are used in their inclusive sense; that is, equivalent to the term "including" and its corresponding cognates.

As used herein, the singular form "a", "an", and "the" includes plural references unless indicated otherwise.

Various proteins characterized as containing OB-fold domains are known in the art and described herein. As described herein in more detail, "OB-fold domain" encompasses family members that share the structural feature of a conserved fold and binding face. OB-fold domain members may also share sequence relatedness. It is contemplated that any OB-fold domain, or portion thereof, can be used to produce a modified OB-fold domain. As used herein, a "naturally occurring" OB-fold domain refers to an OB-fold domain that has not been genetically engineered to contain nucleic acid or amino acid modifications. As used herein, a "modified OB-fold domain" comprises at least one modified amino acid residue as compared to a naturally occurring OB-fold domain. A modification includes a deletion, substitution, or addition or one or more residues or a combination thereof, as long as the modified OB-fold domain retains the fold-related binding face such that it is available for interaction with a binding partner. It is not required that a "modified OB-fold domain" retain the exact structural features of a naturally occurring OB-fold domain. Modified OB-fold domains may comprise modifications in any amino acid residue including modifications in an amino acid residue of the binding face (the binding face includes the β-sheet and adjacent loops), a loop strand, a core region (a region in the hydrophobic interior of the protein that is not exposed to aqueous solvent), and may further comprise amino acid modifications in any portion of the protein comprising the OB-fold domain, as long as the modified OB-fold domain retains the fold-related binding face such that it is available for interaction with a binding partner. In some examples, a modified OB-fold domain is characterized by an ability to bind a binding partner that the naturally occurring OB-fold domain does not. In other examples, a modified OB-fold domain has modified binding with its naturally occurring binding partner. In some examples, an OB-fold domain is isolated, that is, removed from at least a portion of the naturally occurring protein within which it is contained. In other examples, a modified OB-fold domain is associated with a non-naturally occurring protein. In other examples, a modified OB-fold domain is associated with a naturally or non-naturally occurring protein, to which the naturally-occurring OB-fold domain does not bind or to which the naturally-occurring OB-fold domain binds only non-specifically. In other examples, a modified OB-fold domain can be produced where the naturally-occurring OB-fold domain does not have a known binding partner. It will be appreciated that the binding partner, if any, to a naturally occurring OB-fold domain may not be known a priori when screening a library of modified OB-fold domains for binding to a particular binding partner.

Modified OB-fold domains can be prepared which bind to the natural substrate of a naturally occurring OB-fold domain with altered binding characteristics. Such altered binding characteristics can be demonstrated under the same conditions as the naturally occurring OB-fold domain. Alternatively, the altered binding characteristic may be one or more of (but not limited to) thermostable binding (e.g., the modified OB-fold domain demonstrates stronger binding to the natural substrate at elevated temperatures than the naturally occurring OB-fold domain), thermolabile binding (e.g., the modified OB-fold domain demonstrates weaker binding to the natural substrate at elevated temperatures than the naturally occurring OB-fold domain), modified binding under different conditions of pH (e.g., the modified OB-fold domain demonstrates stronger binding to the natural substrate at high pH than the naturally occurring OB-fold domain, or demonstrates weaker binding to the natural substrate at high pH than the naturally occurring OB-fold domain, or demonstrates stronger binding to the natural substrate at low pH than the naturally occurring OB-fold domain, or demonstrates weaker binding to the natural substrate at low pH than the naturally occurring OB-fold domain), or modified binding under different conditions of ionic strength (e.g., the modified OB-fold domain demonstrates stronger binding to the natural substrate at high ionic strength than the naturally occurring OB-fold domain, or demonstrates weaker binding to the natural substrate at high ionic strength than the naturally occurring OB-fold domain, or demonstrates stronger binding to the natural substrate at low ionic strength than the naturally occurring OB-fold domain, or demonstrates weaker binding to the natural substrate at low ionic strength than the naturally occurring OB-fold domain). The modified binding or altered binding characteristic can comprise about at least a 25%, about a 50%, or about a 75% reduction in the dissociation constant of the modified OB-fold domain with its naturally occurring binding partner, as compared to the corresponding naturally occurring OB-fold domain (that is, the modified OB-fold domain may bind at least about 1.33, 2, or 3 times more strongly than the naturally occurring OB-fold domain). In one embodiment, the modified binding comprises a decrease in the dissociation constant by a factor of at least about 2, about 3, about 4, about 5, about 6, about 8, about 10, about 15, about 20, about 25, about 50, about 100, about 200, about 500, about 1000, about 5000, about 10,000, about 50,000, or about 100,000 of the modified OB-fold domain with its naturally occurring binding partner, as compared to the corresponding naturally occurring OB-fold domain (that is, the modified OB-fold domain may bind at least about 2, about 3, about 4, about 5, about 6, about 8, about 10, about 15, about 20, about 25, about 50, about 100, about 200, about 500, about 1000, about 5000, about 10,000, about 50,000, or about 100,000 times more strongly than the naturally occurring OB-fold domain).

A "library" of modified OB-fold domains refers to a collection of OB-fold domains that includes a high ratio of modified OB-fold domains as compared to naturally occurring OB-fold domains. That is, a library of modified OB-fold domains does not imply that the collection contains only modified OB-fold domains. A library of modified OB-fold domains may contain some percentage of unmodified or naturally occurring OB-fold domains. The library may contain OB-fold domains having one or more or multiple amino acid residues randomized. For example, a library of modified OB-fold domains may contain OB-fold domains that contain random modifications in one amino acid residue (which modification may be a single type of modification, such as a single amino acid substitution, or multiple different modifications, such as for example a substitution of a single amino acid with two or more random amino acids) or two or more amino acid residues, which can be in one or more structural regions, such as for example, in the binding face, and/or loop region, and/or core region. A modified OB-fold domain may have additional modifications or the protein comprising the modified OB-fold domain may have modifications in amino acid residues, as long the fold-related binding face is available for interaction with binding partners. A "library" of modified OB-fold domains does not imply any particular size limitation to the number of members of the collection. A library may contain as few as about 10 variants, and may range to greater than $10^{20}$ variants. In some embodiments the library will have up to about $10^8$ variants, and in some embodiments the library will have up to about $10^{12}$ variants. A "library" of modified OB-fold domains refers to the collection of modified OB-fold domains that are encoded via nucleic acid alterations, that is, at the stage of gene assembly prior to introduction into an expression system as well as the collection that is introduced into an expression system, expressed and/or displayed.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH2) or a mixed phosphoramidate-phosphodiester oligomer. Peyrottes et al. (1996) *Nucleic Acids Res.* 24: 1841-8; Chaturvedi et al. (1996) *Nucleic Acids Res.* 24: 2318-23; Schultz et al. (1996) *Nucleic Acids Res.* 24: 2966-73. A phosphorothioate linkage can be used in place of a phosphodiester linkage. Braun et al. (1988) *J. Immunol.* 141: 2084-9; Latimer et al. (1995) *Molec. Immunol.* 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

A "host cell" includes an individual cell or cell culture which can be or has been a recipient of nucleic acid encoding an OB-fold domain, and in some examples, a modified OB-fold domain. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with nucleic acid encoding an OB-fold domain. In some examples, the host cell is capable of expressing and displaying the OB-fold domain on its surface, such as for example, phage display. "Expression" includes transcription and/or translation.

A nucleic acid that "encodes" an OB-fold domain, or portion thereof, is one that can be transcribed and/or translated to produce the OB-fold domain or a portion thereof. The antisense strand of such a nucleic acid is also said to encode the OB-fold domain.

I. OB-Fold Protein Domains

At the most general level, the OB-fold domain is a five-stranded mixed $\beta$ barrel. See for example, Arcus, 2002, Curr. Opin. Struct. Biol. Vol 12:794-801. The OB-fold domain is found in all three kingdoms and, as discussed in more detail herein, is represented in both sequence and structural databases. Generally speaking, OB-fold domains have a conservation of fold and functional binding face. Different OB-fold domains use their fold-related binding face to variously bind oligosaccharides, oligonucleotides, proteins, metal ions, and catalytic substrates.

OB-fold domains have a number of features which make them well suited as scaffolds for randomisation of amino acid positions and selection of modified OB-fold domains with desired properties. OB-fold domains are generally small, stable proteins which are easily produced and randomised. Theobald et al., 2003, supra, disclose that OB-fold domains range between 70 and 150 amino acids in length. Additionally, the face of the OB-fold domain protein, already demonstrated through evolution to be versatile, is available for randomization. The OB-fold domain is ubiquitous in all three kingdoms and thus, it is possible to choose an OB-fold domain to suit particular applications. For example, OB-fold domains from thermostable microorganisms are described herein for production of libraries of modified OB-fold domains. Ob-fold domains can be selected for therapeutic application; for example, an enzymatic OB-fold domain can be selected to produce proteins with new enzymatic activities. These features provide an advantage over more traditional antibody and protein scaffolds.

Figure 1B:
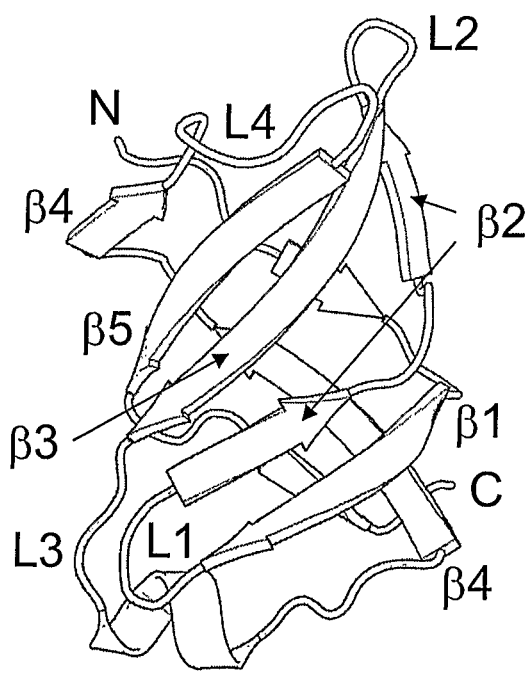
Figure 1C:
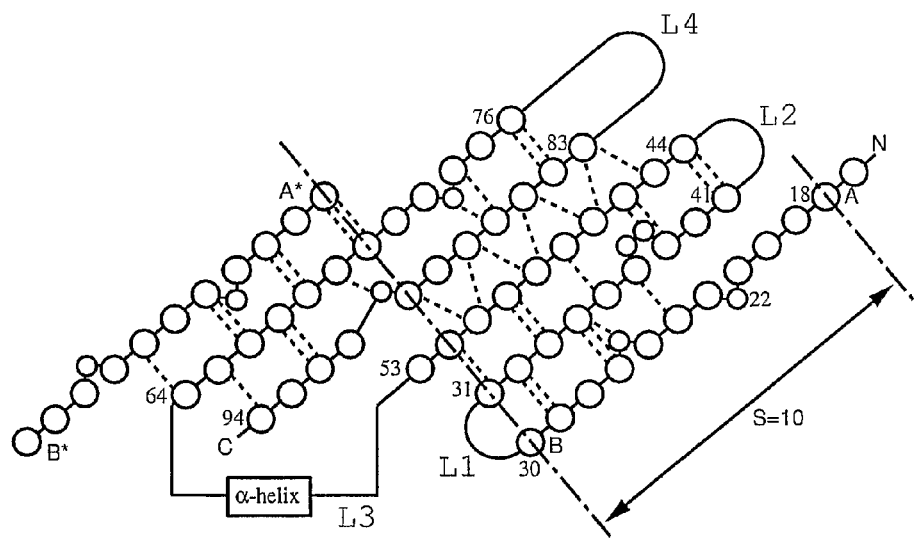

The general structure of OB-fold protein domains is a 5-stranded mixed $\beta$-barrel that presents a concave $\beta$-sheet as an external binding face flanked by two variable loop regions. In the majority of cases the barrel has a Greek-key topology and one end of the barrel is capped by an $\alpha$-helix (23). $\beta$-barrels are uniquely described by their number of strands n, and the shear number, S (26,27). The shear number describes the degree to which the strands are tilted away from the axis of the barrel. FIGS. 1A-1C show a $\beta$-barrel with S=10. This is the number of residues which are formally part of the $\beta$-sheet (thus excluding $\beta$-bulges) and are counted along the strand in going from A to A*. There are two possibilities (S=8 or S=10) for the OB-fold and both of these are observed. As examples, the OB-fold domain of the aspartyl tRNA sythetase (aspRS), which binds tRNA, has S=10 whereas the cold-shock OB-fold domain DNA binding domains has S=8. The OB-fold domain binding face has at its center $\beta$ strands 2 and 3, and is bounded at the bottom left by loop 1, at the top by loop 4 and at the top right by loop 2 (see FIGS. 1A-1C). In different OB-fold domain structures, loops 2 and 4 show wide variation in both length and sequence. See Arcus, 2002, Curr. Opin. Struct. Biol. Vol 12: 794-801. Modified OB-fold domains can vary in length. For example, loop 2 often varies between 2 to 4 amino acids and loop 4 often varies between 3 to 10 amino acids, and in some cases loop 4 accommodates an insertion of much greater length, up to about 30 amino acids.

A survey of 20 sequenced genomes places the OB-fold domain at $28^{th}$ in a list of the most prevalent biological architectures (27). The OB-fold domain has been found in a variety of proteins including humans, yeast and bacteria. For example, in bacterial superantigens (Sags), an OB-fold domain mediates protein-protein interactions in the bacterial attack on the human immune system (21 and 22). In these proteins it binds a broad range of ligands, including proteins, oligonucleotides and oligosaccharides (23). Examples of the diversity of OB-fold domain proteins include single stranded DNA binding in the oncogene BRCA2 (Yang H. et al., 2002 Science, Vol. 297, 1837-1848), telomere end binding on chromosomes for the yeast protein Cdc13 (Lei M. et al, 2003 Nature, Vol. 426, 198-203), and cell-surface oligosaccharide binding in pathogenic bacteria (Stein P. E. et al, 1994, Structure, Vol. 2, 45-47). As determined by the Structural Classification of Proteins database (SCOP), the standard in classifying protein structures into related "families" and "superfamilies", OB-fold protein domains are found in nine related superfamilies. Those OB-fold domains which belong to the same "family" have an evolutionary relationship at the sequence, structural and functional levels and appear to be descended from a common ancestor. The OB-fold domain "families" which belong to the same "superfamily" are evolutionarily related based on similar structural and functional features in the absence of definitive sequence similarities. The SCOP database is comprised of proteins of known structure (i.e. their structures have been experimentally determined using either X-ray crystallography or high resolution NMR).

Additional OB-fold domains can be determined by the skilled artisan based on structural relatedness, that is, the presence of the fold-related binding face, or structural relatedness and sequence relatedness to known OB-fold domains described herein and known in the art. There are sequence similarities within superfamilies and families and these can be used to identify additional proteins whose structures have not been previously determined under the OB-fold umbrella. See, for example, the publicly available Pfam database (at <sanger.ac.uk/Software/Pfam>). An additional publicly available database is Superfamily (at <supfam.mrclmb.cam.ac.uk/SUPERFAMILY>) which uses hidden Markov models derived from SCOP to classify protein sequences into superfamilies. For example, the "nucleic acid-binding proteins" comprise a superfamily in SCOP database. There are currently 11 families and 66 individual protein structures in this superfamily in SCOP. From these 11 families and 66 structures, the Superfamily database has derived rules to classify 21,158 protein sequences as OB-fold proteins belonging to the "nucleic acid-binding protein" superfamily. Similarly, the CheW-like superfamily has just a single family and two protein structures in SCOP whereas this has been expanded to include 898 proteins in the Superfamily database.

i. Classification of OB-Fold Domains at SCOP

For the class of OB-fold domains characterized by SCOP as all beta, with barrel, closed or partly opened where $n=5$, and $S=10$ or $S=8$; greek-key, SCOP currently identifies the following Superfamilies (the numbers in parenthesis are the SCOP reference numbers):

1. Staphylococcal Nuclease (50199)

For Staphylococcal nuclease, there is currently a single member of this family although there are many structures in the database for Staphylococcal nuclease. The OB-fold is a closed beta-barrel, $n=5$, $S=10$.

2. Bacterial Enterotoxins (50203)

For bacterial enterotoxins, there are two families in this superfamily: Bacterial AB5 toxins (B subunits) and the N-terminal domain of superantigen toxins. The Bacterial AB5 toxins include the heat labile toxin from *E. coli*, the Cholera toxin and Pertussis toxin. All have a closed beta-barrel topology with $n=5$ and $S=10$ with the single exception of the Cholera toxin whose barrel is slightly opened. The N-terminal domains of the superantigen toxins and superantigen-like toxins are all proteins from *Staphylococcus aureus* and *Streptococcus pyogenes* and have typical $n=5$, $S=10$ closed-barrel topologies. There are a large number of these proteins encoded in the genomes of these organisms. The Staphylococcal proteins have recently been renamed according to: "Standard Nomenclature for the Superantigens Expressed by *Staphylococcus*." Gerard Lina, Gregory A. Bohach, Sean P. Nair, Keiichi Hiramatsu, Evelyne Jouvin-Marche, and Roy Mariuzza, for the International Nomenclature Committee for Staphylococcal Superantigens *The Journal of Infectious Diseases* 2004; 189:2334-6.

3. TIMP-like (50242)

TIMP-like Proteins are eukaryotic proteins that currently are divided into three families all with $n=5$, $S=10$ closed-barrel topology:

a. Tissue inhibitor of metalloproteinases, TIMP (50243) (contains an irregular alpha+beta subdomain in the C-terminal extension).
b. Netrin-like domain (NTR/C345C module) (89320)
c. The laminin-binding domain of agrin (63767)

4. Heme Chaperone CcmE (82093)

For the Heme Chaperone, CcmE, there is a single family annotated in this superfamily. Representative structures are from *E. coli* and *S. putrefaciens*.

5. Tail-associated Lysozyme gp5, N-terminal Domain (69255)

For Tail-associated lysozyme gp5, N-terminal domain, there is a single structure which represents both the family and this superfamily. The protein is from bacteriophage T4 and the N-terminal domain is part of a much larger protein complex which forms the cell-puncturing device of the phage.

6. Nucleic Acid-binding Proteins (50249)

Nucleic acid binding proteins are a large superfamily that encompasses many proteins.

The following are the family demarcations and descriptors:
a. Anticodon-binding domain (50250)
barrel, closed; $n=5$, $S=10$
b. RecG "wedge" domain (69259)
c. DNA helicase RuvA subunit, N-terminal domain (50259)
barrel, closed; $n=5$, $S=10$
d. Single strand DNA-binding domain, SSB (50263)
barrel, closed, $n=5$, $S=10$
e. Myf domain (50277)
f. Cold shock DNA-binding domain-like (50282)
barrel, closed; $n=5$, $S=8$
g. Hypothetical protein MTH1 (MT0001), insert domain (74955)
h. DNA ligase/mRNA capping enzyme, domain 2 (50307)
i. Phage ssDNA-binding proteins (50315) (4)
barrel, open; $n*=5$, $S*=8$; the members' structures vary greater that those from cellular organisms
j. DNA replication initiator (cdc21/cdc54) N-terminal domain (89332)
k. RNA polymerase subunit RBP8 (50321)
duplication; contains tandem repeat of two incomplete OB-folds; forms a single barrel; $n=8$, $S=10$ 7. Inorganic Pyrophosphatase (50324)

For Inorganic pyrophosphatase, there is just one family in this superfamily. This family has a very deep lineage as there are examples from bacteria, archaea and eukaryotes.

1. Inorganic pyrophosphatase (50325)
barrel, closed; $n=5$, $S=8$
1. Inorganic pyrophosphatase (50326)
eukaryotic enzyme has additional secondary structures at both N- and C-termini
a. Baker's yeast (*Saccharomyces cerevisiae*) (50327)
b. Archaeon *Silfolobus acidocaldarius* (50328)
c. *Escherichia coli* (50329)
d. *Thermus thermophilus* (50330)

8. MOP-Like (50331)

In the MOP-like grouping, there are three families, all with similar functionality and all from bacteria.

a. Molybdate/tungstate binding protein MOP (50332)
b. BiMOP, duplicated molybdate-binding domain (50335)
duplication: tandem repeat of two OB-fold domains with swapped C-terminal strands
c. ABC-transporter additional domain (50338)
probably stems out from the biMOP domain 9. CheW-Like (50341)

This is represented in a single family with two structures from *Thermotoga maritima*, CheW and CheA.

ii. Sequence Databases Pfam and Superfamily

The descriptions from SCOP relate to OB-fold domains from proteins whose 3-dimensional structures have been determined either by X-ray crystallography or NMR. Additional OB-fold protein domains identified in the database Pfam based on sequence similarity and in the database Superfamily based on sequence profiles derived from SCOP and then applied to the major sequence data are encompassed within the present invention. The present invention encompasses additional OB-fold domains known to those of skill in the art.

As described below, in Pfam there are many families which together represent OB-fold domains. The annotation is as follows:
Family Name
Annotation
Pfam accession number
Total number of proteins in this family in the Pfam database
tRNA_anti
OB-fold nucleic acid binding domain
Accession number: PF01336
Number of proteins: 1351
Telo_bind
Telomere-binding protein alpha subunit, central domain
Accession number: PF02765
Number of proteins: 33
SSB
Single-strand binding protein family
Accession number: PF00436
Number of proteins: 415
DUF388
Domain unknown function (DUF388)
Accession number: PF04076
Number of proteins: 49
DNA_ligase_aden
NAD-dependent DNA ligase OB-fold domain
Accession number: PF03120
Number of proteins: 190
Stap_Strp_toxin
Staphylococcal/Streptococcal toxin, OB-fold domain
Accession number: PF01123
Number of proteins: 180
eIF-5a
Eukaryotic initiation factor 5A hypusine, DNA-binding OB fold
Accession number: PF01287
Number of proteins: 104
Gp5_OB
Gp5 N-terminal OB domain
Accession number: PF06714
Number of proteins: 6

All of the OB fold domains described herein, known in the art and later identified can be used as a scaffold to prepare modified OB-fold domains and to prepare libraries of modified OB fold domains that can be used for screening for altered binding characteristics and altered functional features.

iii. OB-fold Binding Face for Randomization of Amino Acids

A modified OB-fold domain and/or a library of modified OB-fold domains can be prepared based on the structure of any OB-fold domain, including those described herein, known in the art or later identified. Libraries of modified OB-fold domains can be prepared based on methods described herein and known in the art. For example, for any given OB-fold domain, nucleic acid encoding one or more amino acid residues, such as for example, amino acid residues in the strands of an external binding face and/or amino acid residue in the strands of a loop and/or amino acid residues in other portions of the protein containing the OB-fold domain, can be targeted for amino acid residue randomization (that is, random mutation of the amino acid residue(s) via nucleic acid modifications). In some examples, amino acid residues in strands of the external binding face of an OB-fold domain are targeted for amino acid residue randomization. In other examples, particular structures within the OB-fold domain can be targeted for amino acid residue randomization. For example, one or multiple amino acid residues present in the strands of the binding face of an OB-fold domain can be targeted for randomization. The binding face for OB-fold domains includes the C-terminal half of beta-strand 1, beta-strand 2, beta-strand 3, the C-terminal half of beta-strand 4 and beta-strand 5. See FIGS. 1A-1C for reference. In another example, the amino acid residues in the loops between the beta-strands of the core OB-fold domain may be targeted for random mutations. In another example, where there are major insertions in the loop regions flanking the OB-fold core domain (e.g. the inorganic pyrophosphatases) amino acid residues on these inserted loops may be selected for randomization. The present invention also encompasses modified OB-fold domains having portions, that is amino acid residues, of the core modified to produce changes in stability to the protein.

II. Production of Modified OB-fold Domains and Display Methods

In illustrative embodiments described herein in the examples, two thermophilic OB-fold protein domains, translation initiation factor, IF-5A (S=8), and the aspartyl tRNA synthetase, aspRS(S=10), onto which mutations were introduced, were used to make libraries of modified OB-fold domains, by randomising amino acid residues in the binding face of the OB-fold protein. Both of these proteins are from the hyperthermophilic chrenarchaeon, *Pyrobaculum aerophilum*. Libraries were generated synthetically using long oligonucleotides with specific amino acid positions in the binding face of the OB-fold domain being randomised, followed by gene assembly using PCR. Libraries were tested for the rates of overexpression of their encoded proteins and estimates were made about the fraction of soluble and heat stable proteins encoded by the library. It is demonstrated herein that the aspRS OB-fold domain (aspRS-OB) can be displayed and selected on the surface of phage. Different libraries of modified OB-fold domains, based on the aspRS scaffold as described herein in the examples, were prepared and subjected to phage display methods to demonstrate that modified OB-fold domains can be produced that are capable of binding to different substrates including tRNA, protein and cellulose ligands. In one illustrative embodiment disclosed herein, a binding interaction between a modified OB-fold domain, which in its natural state was a nucleic acid binding domain, and lysozyme is demonstrated.

As will be understood by one of skill in the art, various methods known in the art for preparing modifications of nucleic acid can be used to prepare (encode) OB-fold domains having modification in one or more amino acid residues. Nucleic acids encoding OB-fold domains may be obtained using standard methods in the art, such as chemical synthesis, recombinant methods and/or obtained from biological sources. Nucleic acid of interest may be placed under the control of one or more elements necessary for their expression in any particular host cell. A variety of host cells are available to propagate OB-fold domains, and displays methods are known in the art and described herein that may be used in display modified OB-fold domains on their surface. Display methods include without limitation phage display, bacterial display, yeast display, ribosome display, and mRNA display.

i. Display Methods

Display technologies involve the screening of large libraries of expressed proteins using an immobilised ligand to characterize or discover new interactions between individual proteins and the target ligand. The most important characteristic of display technologies is the ability to couple the proteins being screened (phenotype) with the genetic information encoding them (genotype). In all display technologies the genetic information is isolated simultaneously with the screened protein. This is generally achieved by displaying proteins or protein fragments on the surface of biological entities, e.g. phage, yeast or bacteria, and employing the replication systems of the organism to amplify the library. As an alternative to these in vivo systems, the whole process can also be carried out in vitro and such technologies called ribosome display or mRNA display. In these cases in vitro-generated transcripts are translated in cell extracts and RT-PCR is used to amplify the genetic information after the ligand-mediated isolation of mRNA-ribosome-protein complexes has taken place.

a. Phage Display

The display of foreign peptides and proteins on the surface of filamentous bacteriophages is called 'phage display' and is now a commonly used technique to investigate molecular interactions. Normally the protein library to be screened is expressed as a fusion with the gene III protein product at one end of the bacteriophage particle or as a fusion with the gVIII protein on the surface of the phage particle. Infection of bacteria with such a phage library allows very efficient library amplification (Griffith et al., 1994). A typical phage display protocol involves the production of phage particles in a bacterial host with each particle displaying the gene product of one member of the gene library as a fusion with one type of its coat proteins (gIII or gVIII proteins). A library of phage particles is taken through a selection process for binding to an immobilised target molecule ('biopanning') involving binding of the phage library to the target, washing steps to remove non-bound phage, and elution of bound particles. Usually several rounds of panning are necessary to select molecules with the desired characteristics involving reamplification of eluted phage in the bacterial host and selection on the immobilised target. In illustrative embodiments disclosed herein in the Examples, phage display methods are used to display and screen modified OB-fold domains.

b. Bacterial Display and Yeast Display

The Bacterial display and Yeast display technologies allow expression of recombinant proteins on the surface of yeast cells *S. cerevisiae* (Boder and Wittrup, 1997) or bacteria (*E. coli, Staphylococcus carnosus*) (Daugherty et al., 1998, Wernerus et al., 2003) as a fusion with the a-agglutinin yeast adhesion receptor or a bacterial outer membrane protein (OMP) respectively.

The expressed fusion proteins also contain tag sequences, allowing quantification of the library surface expression by flow cytometry. Combined with indirect fluorescent labeling of the ligand, anti-tag labeling allows cell sorting by FACS (fluorescence activated cell sorting) and the determination of the binding affinities of the interactions (Feldhaus et al, 2003, Wernerus et al., 2003). The features of yeast expression system that make it valuable beside other display techniques are a correct post-translational modification, processing and folding of mammalian proteins which can be problematic in bacterial or in vitro display systems.

c. Ribosome Display and mRNA Display

Ribosome display and mRNA display are technologies that enable the selection and evolution of large protein libraries in vitro. The only biological component required is a bacterial cell extract that contains the factors required for the translation of in vitro-generated transcripts encoding the protein sequences. In ribosome display, genotype and phenotype are linked together through ribosomal complexes, consisting of messenger RNA (mRNA), ribosome, and encoded protein, that are used for selection (Hanes and Pluckthun, 1997). The mRNA display method employs puromycin to link mRNA to the translated protein and thus allows purification of an mRNA-protein conjugate containing genotype and phenotype information. After selection, the isolated mRNAs or mRNA conjugates are amplified by RT-PCR and can be transcribed and translated for another round of selection (Lipovsek and Pluckthun, 2004). References for display methods include the following list all of which are here by incorporated by reference in their entirety: Boder E T and Wittrup K D (1997) Nat. Biotechnol. 15:553-7; Feldhaus M J et al. (2003) Nat. Biotechnol. 21:163-70; Griffiths, A D, et al. (1994) EMBO Journal 13, 3245-3260; Hanes J, Pluckthun A., et al (1997) PNAS May 13; 94(10):4937-42; and Lipovsek D, Pluckthun A., (2004) J. Immunological Meth. 290 51-67; Wernerus H, et al. (2003) Appl Environ Microbiol. 69(9): 5328-35.

Display methods are disclosed in for example: Boder E T and Wittrup K D (1997) Nat. Biotechnol. 15:553-7; Feldhaus M J et al. (2003) Nat. Biotechnol. 21:163-70; Griffiths, A D, et al. (1994) EMBO Journal 13, 3245-3260; Hanes J, Pluckthun A., (1997), PNAS May 13; 94(10):4937-42; Lipovsek D, et al. (2004) J. Immunological Meth. 290 51-67; and Wernerus H, et al. (2003) Appl Environ Microbiol. 69(9):5328-35.

III. Potential Targets for Screening Modified OB-Fold Domains

The ligands of naturally occurring OB-fold domains are diverse. The production of libraries of modified OB-fold domains extends the diversity of possible targets for OB-fold domains. Potential targets for screening against libraries of modified OB-fold domains encompass a variety of molecules, including, for example, but not limited to, nucleic acids, proteins, peptides, polypeptides, carbohydrates, oligosaccharides, and hormones.

i. Nucleic Acids

A large number of OB-fold domains are involved in binding to single stranded DNA and RNA. These include the single stranded DNA binding domains of the oncogene BRCA2, several domains from human replication protein A and the anticodon binding domain of Aspartyl- and Lysyl-tRNA synthetases. Accordingly, single stranded DNA and tRNA can be used as ligand targets for screening libraries of modified OB-fold domains.

ii. Protein Targets

A variety of proteins can be used for screening libraries of modified OB-fold domains, such as enzymes, regulatory proteins, protein and peptide hormones, transport proteins, etc. In an illustrative embodiment disclosed herein, lysozyme is used as a protein target. Other targets include, but are not limited to, ubiquitin, complement component C4, plasminogen precursor, apolipoprotein A-II, plasma protease C1 inhibitor, transthyretin and serum amyloid P-component.

iii. Oligosaccharide Targets

Oligosaccharides play an integral part in the biology of all organisms. Oligosaccharide substrates such as, for example, but not limited to, laminarihexose, mannopentaose and xylopentaose can be used as targets.

iv. Hormones

Hormones such as, for example, the steroid hormones estrogen, testosterone, and cortisol; catecholamines, such as epinephrine, and other such molecules can be used to screen against libraries of OB-fold domains. Currently there is no evidence that the OB-fold domain has a steroid hormone or other cofactor as a natural ligand. In addition, it has been classically difficult to raise highly specific antibodies to steroids and a concave binding face, such as the OB-fold domain binding face may prove better at raising the specificity of binding for a particular hormone.

v. Small Organic Molecules

Small organic molecules (defined as organic molecules with a molecular weight equal to or less than about 1000 daltons) can also be used as targets for OB-fold domains. The small organic molecule may be a naturally occurring molecule, or a synthetic molecule not found in nature. A naturally occurring small organic molecule may be associated with a living system (such as the steroid hormones; see above) or may occur abiotically. Small organic molecules include, but are not limited to, pollutants or other undesirable substances, such as DDT or polychlorinated biphenyls (PCB's). Small organic molecules include, but are not limited to, drugs and pharmaceuticals, such as doxorubicin and paclitaxel.

IV. Applications for OB-fold Domains

As described herein, the OB-fold domain is a versatile molecular recognition platform. A variety of OB-fold domains are known in the art, disclosed herein, and have been identified in SCOP and other databases such as Pfam and Superfamily. Such OB-fold domains can be used in methods for preparing modified OB-fold domains as well as libraries of modified OB-fold domains which can be screened against targets, such as, for example, nucleic acids, proteins, hormones, carbohydrates and oligosaccharides. Such screening methods can be used to identify modified OB-fold domains with desired properties. For example, a human OB-fold domain can be used as a scaffold for the production of libraries of modified OB-fold domains for the screening against human targets that might have application in human therapeutics. In another example, a yeast OB-fold domain can be used as a scaffold for the production of libraries of modified OB-fold domains that might have application in biotechnology or fermentation applications. In yet another example, an enzymatic OB-fold domain can be used as a scaffold for the production of libraries of modified OB-fold domains with new enzymatic properties.

The potential applications for modified OB-fold domains fall into three broad categories: diagnostic reagents; therapeutic application; and tools.

Modified OB-fold domains can be used in a wide range of molecular biology tools and include, for example, use as protein purification reagents for affinity purification of proteins from either recombinant sources or natural sources such as serum. In such applications, OB-fold domains with specific binding affinity for a protein of choice will be immobilised on beads and then used to affinity purify the target protein. Other applications include the use in protein detection for Western blotting; protein detection using fluorescent-labeled OB-fold domains; and protection agents for single stranded DNA and RNA. A central advantage of OB-fold domains over antibodies in these contexts is the tailoring of the stability of the modified OB-fold domain to match the reagent. For example, thermostable OB-fold domains, such as those obtainable from *Pyrobaculum aerophilum* may be more effective than antibodies as affinity purification reagents.

Diagnostic applications for modified OB-fold domains include, for example: protein detection in fluids such as serum, culture supernatants, and contaminated water; genotyping (many OB-fold proteins are single stranded DNA binding proteins and these could be developed to detect specific DNA or RNA motifs, for use in methods such as genotyping); and in small molecule detection agents.

Given that recombinant antibodies and their fragments currently represent a large number of all biological proteins undergoing clinical trials for diagnosis and therapy, alternatives to antibody libraries such as libraries of modified OB-fold domains have potential as therapeutic agents. Current examples of recombinant antibodies which have reached the marketplace are the oncology therapeutics Herceptin, Anti-HER2 antibody; Rutuxan (Rutuximab) Anti-CD20 antibody; and Avastin Anti-VEGF antibody. Humanized libraries of modified OB-fold domains may be prepared from which specific ones can be identified having appropriate binding characteristics that can find use in the therapeutic arena.

EXAMPLES

Example 1

Materials and Methods

Chemicals and Biochemicals

Standard oligonucleotides were purchased from Invitrogen and all long randomized oligonucleotides were from MWG (Martinsried, Germany). Pfx and taq polymerase and all restriction enzymes were from Invitrogen (Carlsbad, USA). Shrimp alkaline phosphatase (SAP) and T4 ligase were from Roche (Basel, Switzerland). The phagemid vector pRPSP2 and phage VCS-M13 and VCSM-13d3 (Vd3) were from Dr. J. Ralconjac (31,32). Streptavidin coated magnetic beads and Protector® RNase inhibitor were from Roche, as was hen egg lysozyme. Bovine Serum Albumine was from Sigma. Biotinylated transfer RNA was prepared using the MEGAscript in vitro transcription kit from Ambion (USA) and the biotin RNA labeling mix from Roche. Nitrocellulose membranes for western analysis was from Schleicher & Schuell (Dassel, Germany), and the substrate used was SuperSignal® from Pierce (USA).

Bioinformatics

Structures were viewed, analyzed or transformed into figures from PDB files (33) using Swiss-pdb Viewer and Pymol (at pymol.sourceforge.net). The PDB entry 1bkb (34) was used for structural analysis of IF-5A. For aspRS the PDB files of aspRS homologues 1b8a (35), 1eov (36), 1coa (37) were used.

The structural model of aspRS-OB was obtained from Swiss Model (38-40) by submitting the amino acid sequence of aspRS-OB from *Pyrobaculum aerophilum*. Alignments were done using ClustalW (version 1.8) online via the EBI service website (<www.ebi.ac.uk/services/>).

Cloning

General cloning was carried out according to Sambrook and Russell (41). The wild type genes for aspRS-OB (asp-tRNA synthetase from *Pyrobaculum aerophilum* IM2, bases 1-327, amino acids 1-109, NCBI access number NP_558783) and IF5A-OB (IF-5A from *Pyrobaculum aerophilum* IM2, NP_560668, bases 208-399, amino acids 76-139) were amplified by PCR from *P. aerophilum* IM2 genomic DNA (NC 003364, (42)) using oligonucleotides 005 and 006 for aspRS-OB and 011 and 012 for IF5A-OB. Oligonucleotide sequences are listed in Appendix I. All PCR products for overexpression were digested with BamHI and EcoRI and ligated into pProEx-Htb. pProEx-Htb produces the protein as an N-terminal His$_6$-tagged fusion-protein. For cloning of the aspRS-OB gene into pJARA140, aspRS-OB was amplified by the PCR using the oligonucleotide pair 050/044 and digested using NcoI and NotI. pJARA140 was also digested with the same enzymes and dephosphorylated prior to ligation. For subcloning, selected mutant genes were amplified using vector specific primers and inserted into donor vector pDONR221 and subsequently into pDEST15, both part of the GATEWAY® cloning system (Invitrogen). pDEST15 allows protein expression as a fusion to glutathione-S-transferase (GST).

*Escherichia coli*

*E. coli* K12 strain XL1-blue (43) was used for cloning and plasmid preparations of all constructs derived from pProEx and for small scale protein synthesis, *E. coli* JM101 derivative TG1 was used for cloning of all pRPSP2 constructs and for all phage produced with VCS-M13 helper phage. *E. coli* K561 transformed with pJARA131 and pJARA112 (resulted in *E. coli* K1762, (44)) was used for preparation of VCS-M13d3 helper phage for multivalent display. *E. coli* BL21 (DE3) (Novagen) was used for large scale protein production and purification.

Gene Libraries Construction

Figure 2A:
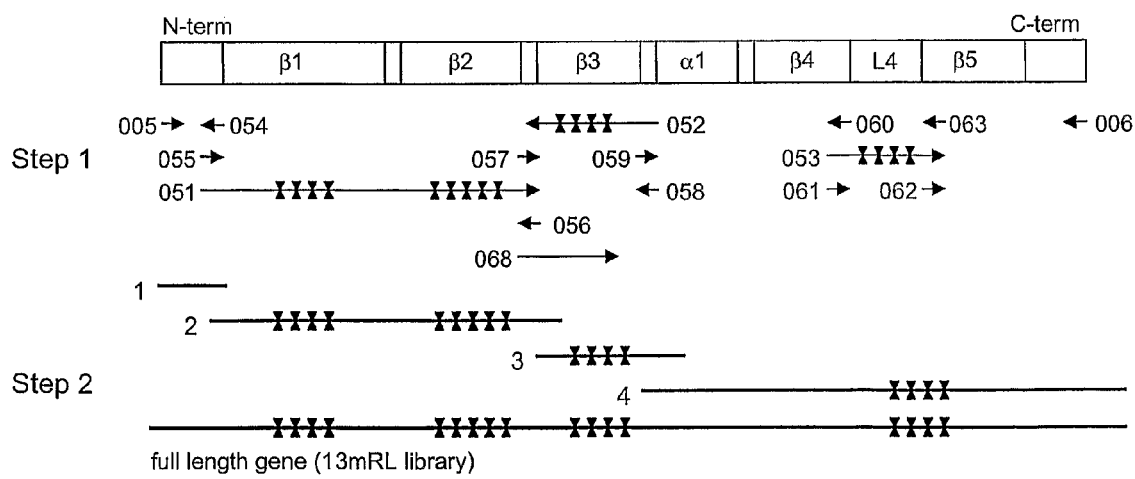
FIGS. 2A-2B provide an overview of oligonucleotides used for library construction of aspRS-OB.
Figure 2B:
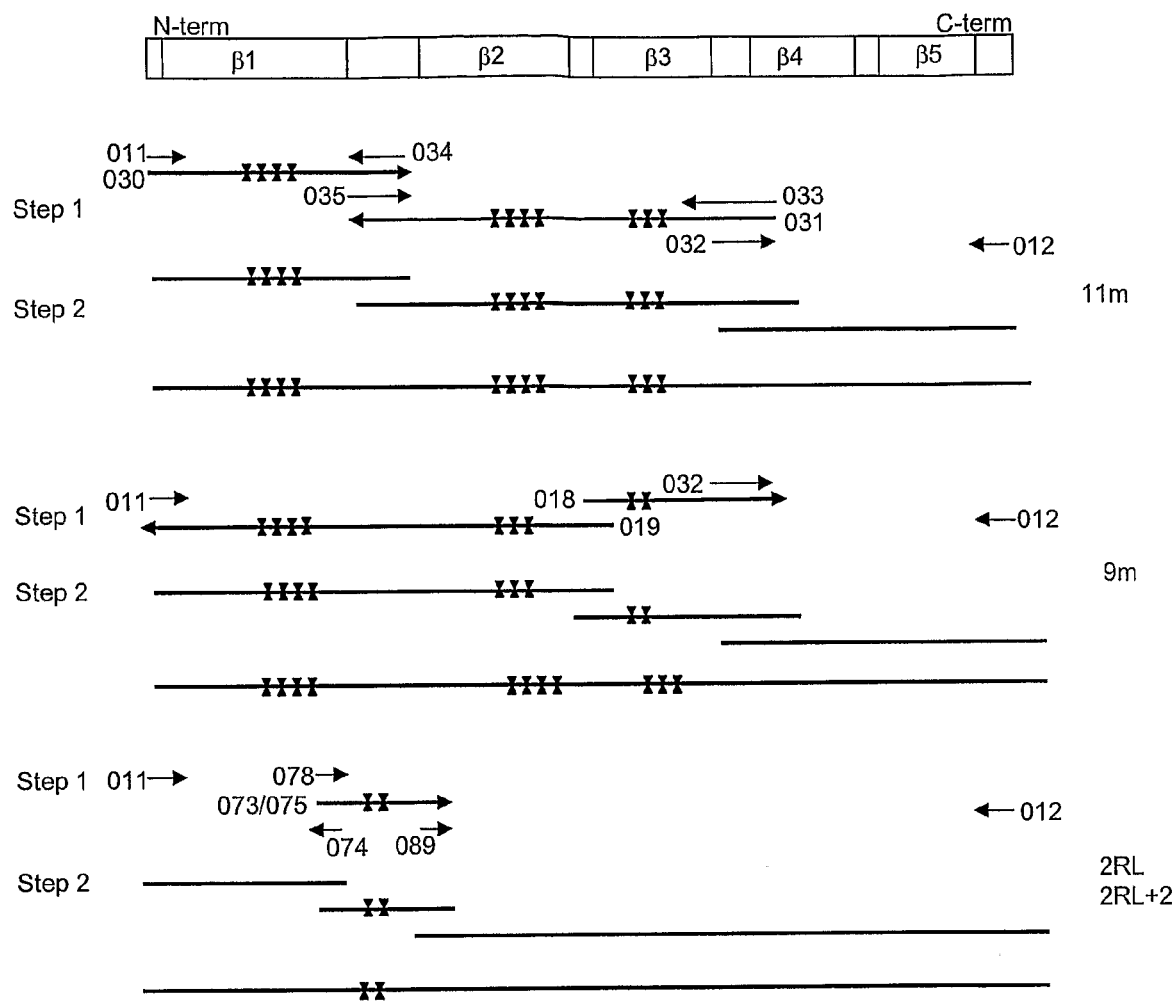

Libraries were constructed by incorporation of mutagenic oligonucleotides containing the codon NNK (N=A, C, G or T, K=T or G) in selected positions. AspRS-OB gene fragments carrying incorporated mutations were generated by PCR and then assembled into full-length genes. Long oligonucleotides which introduce randomized positions are listed in Table 1. In a first PCR step, gene fragments were generated using corresponding flanking primers and incorporating the oligonucleotides randomized at selected positions (30 cycles, 94° C. for 1 min, 52.5° C. for 30 sec, 68° C. or 1 min). In a second step, the gene fragments were assembled into a full length gene by an overlap-extension PCR (25 cycles, 94° C. for 1 min, 52.5° C. for 30 sec, 68° C. for 1 min). The amount of assembled product was calculated by spectrophotometry to be greater than $10^{11}$ molecules to ensure that a diversity of $10^8$ is maintained in the following steps. Assembled products were amplified by PCR (30 cycles, 94° C. for 1 min, 52.5° C. for 30 sec, 68° C. or 1 min) using vector specific primers 005/006 or 011/012 for aspRS-OB and IF5A-OB respectively, digested and ligated into pProEx-Htb. For phage libraries of aspRS-OB primers 050/044 were used for cloning into pRPSP2 (see below). Plasmids containing either the wild type gene or assembled libraries were transformed into *E. coli* XL1-Blue and grown overnight at 37° C. on LB-agar plates complemented with ampicillin (50 µg/ml). Diagnostic PCR was performed by picking individual colonies and growing them in 50 ul LB/Amp for several hours. 1 ul of this culture was used to do a 10 ul PCR amplification (25 cycles, 94° C. for 1 min, 52.5° C. for 30 sec, 68° C. for 1 min) using diagnostic primers for pProEx-Htb or pRPSP2 respectively. Pfx polymerase was used for all preparative PCR reactions whereas taq polymerase was used for diagnostic PCR reactions only. A scheme outlining the assembly strategy for each OB-fold gene is shown in FIGS. 2A and 2B.

Overexpression Profiles of Proteins from Libraries

Figure 3:
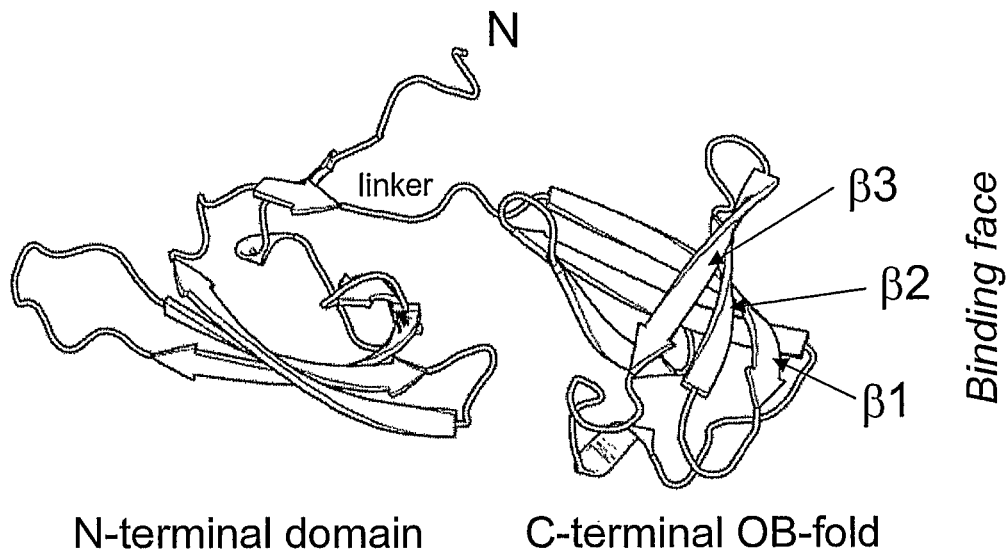
FIG. 3 illustrates the Initiation Factor IF-5A from *Pyrobaculum aerophilum*(1BKB, (34)). This schematic ribbon diagram of IF-5A shows the OB fold at the C-terminus and separated from the N-terminal domain by a linker. β-strands and α-helices are shown as arrows and helical ribbons, respectively. β-strands 1-3 form the proposed single stranded DNA binding face of the OB fold.

For each library, transformed bacteria were plated onto agar (containing LB-amp) and single colonies were picked and grown overnight in 100 µl LB-amp (50 µg.ml$^{-1}$) at 37° C. in a 96 deep-well plate with shaking at 1200 rpm in an Eppendorf Thermomixer. The cultures were diluted by adding 900 µl fresh LB-amp, grown for a further 60 min, and then induced using 1 mM isopropyl-D-thiogalactopyranoside (IPTG) for 4 hrs at 37° C. Bacterial cells were collected by centrifugation, resuspended in 150 µl Tris-buffered saline (TBS: 50 mM Tris-HCl, pH 7.5, 150 mM NaCl) and analyzed by SDS polyacrylamide gel electrophoresis (SDS-PAGE, 15% polyacrylamide). Table 1 is a list of long oligonucleotides used for aspRS-OB and IF5A-OB library construction. Each randomized codon is defined by NNK: N=A/T/G/C, K=T/G or MNN: M=A/C for the antisense codons. Also see FIGS. 3A and 3B.

TABLE 1

| OB fold | oligo | DNA sequences 5' to 3' | location in OB | length in bp |
|---|---|---|---|---|
| aspRS | 051 | GTT GCC GGT TGG GTA NNK NNK TTG NNK GAC NNK GGG NNK NNK AAG NNK GTG NNK GTG NNK GAT AGG GAG GGG GGC GCG (SEQ ID NO: 55) | beta strand 1 + 2 | 78 |
| | 052 | ATC GGG GGT TTT TCC CGC MNN GAG MNN GAC MNN CAC MNN CGC GCC CCC CTC CCT ATC (SEQ ID NO: 56) | beta strand 3 | 57 |
| | 053 | ATT GTT GAG GCC AGT AAA NNK NNK NNK NNK GGT GTG GAG ATT TTC CCC (SEQ ID NO: 57) | loop 4/5 | 48 |
| IF-5A 9m | 018 | TTTATAGTCGCGCATGTCKNNTAGKNNAATKNNATCTCCKNNAACKNNKNNTATKNNCGCCGTGAATTTCTCAAT (SEQ ID NO: 58) | beta strand 1 + 2 | 75 |
| | 019 | GACATGCGCGACTATAAANNKATANNKG TGCCGATGAAATACGTC (SEQ ID NO: 59) | beta strand 3 | 54 |
| IF-5A 11m | 030 | ATT GAG AAA TTC ACG GCG NNK ATA NNK NNK GTT NNK GGA GAT AGC AAC GGC GCG (SEQ ID NO: 60) | beta strand 1 | 54 |
| | 031 | GTA TTT CAT CGG CAC MNN TAT MNN TTT MNN GTC GCG MNN GTC MNN TAG MNN AAT MNN CGC GCC GTT GCT ATC TCC (SEQ ID NO: 61) | beta strand 2 + 3 | 75 |
| IF-5A 2RL | 073 | CTC TCC GTT TCA GGA GAT NNK NNK GGC GCG GTA ATT CAG CTA (SEQ ID NO: 62) | Loop 1/2 | 42 |
| IF-5A 2RL + 2 | 075 | CTC TCC GTT TCA GGA GAT NNK NNK AGC AAC GGC GCG GTA ATT (SEQ ID NO: 63) | Loop 1/2 | 42 |

Resuspended cells were lysed by freeze-thaw and addition of lysozyme (0.5 mg.ml$^{-1}$) and, after sedimentation of insoluble material, the soluble fraction was also analyzed by SDS-PAGE. A small-scale purification step was conducted by binding soluble proteins using 5 µl Ni-NTA resin (Qiagen, Germany). Ni-NTA beads were washed with TBS and bound proteins were identified using SDS-PAGE.

Protein Expression and Purification

Wild type OB-fold domains, aspRS-OB, IF5A-OB and the mutants IF5A-OB/A2 and aspRS-OB/13mRL were expressed and purified in milligram quantities. 25 ml overnight cultures of E. coli XL1-Blue in LB-amp (50 µg.ml$^{-1}$) were used to inoculate 500 ml of LB-amp medium. Cultures were grown at 37° C. to OD$_{600}$=0.6 and induced by 1 mM IPTG for 4 hrs. Bacteria were collected by centrifugation and stored at −20° C. Cells were resuspended in 25 ml TBS+10 mM imidazole and lysed by sonication. OB-fold proteins derived from IF-5A were treated in a heat step which involves incubation for 30 min at 85° C. This denatures a large portion of E. coli proteins. Lysed cells were centrifuged at 16,000 rpm in a Sorvall SS-34 rotor for 30 min. For purification, the lysate was loaded onto a Ni-NTA High trap column (Amersham Pharmacia, Sweden). Elution from the column was performed using an imidazole gradient. Purified protein was dialysed against imidazole-free 20 mM Tris-HCl pH7.5, 150 mM NaCl, concentrated and subjected to a second purification step by size exclusion using a Superdex® 200 column (Amersham).

Phage Library Preparation

General procedures for working with phage were performed according to Barbas et al. (45). To prepare stocks of phage aspRS-OB-pIII-Vd3 for selection, ~6×10$^9$ E. coli TG1 cells harbouring aspRS-OB in pJARA140 were used to inoculate 200 ml, 2×YT-amp (50 µg.ml$^{-1}$). This culture was grown for 1 hour with shaking at 37° C. and infected with approximately 1×10$^{12}$ units Vd3 helper phage for 30 min at 37° C. without shaking. The cells were then washed and grown for another 4 hrs in 2×YT-amp. Phage were then concentrated from the culture supernatant by polyethylene glycol (PEG) precipitation, resuspended in TBS and stored at 4° C. The phage titre was determined as 3.0×10$^{11}$ TDP.ml$^{-1}$.

For cloning of aspRS-OB gene libraries into pRPSP2 the oligonucleotide pair 050/044 was used for PCR-amplification of the assembled gene library. PCR product was digested by NcoI and NotI. Ligation was performed by using approximately 10 ug of NcoI/NotI-digested phage vector pRPSP2 and insert, in a molar ratio of 1:5 in a 1 ml reaction followed by purification on spin columns (Roche or Qiagen, Hilden, Germany). Transformation of the 50 ul eluate was performed into 10×50 ul electrocompetent E. coli TG1 cells by electroporation yielding approximately 1×10$^8$ transformants. Transformed cells were cultured in 100 ml SOC medium for one hour at 37° C., before addition of 400 ml LB/Amp and growing for another hour at 37° C. Samples were taken to estimate the ligation and transformation efficiency by plating a dilution series on LB/Amp agar plates and analyzing individual clones for correct insert size by diagnostic PCR. Colonies were randomly picked and the number of correct inserts was measured from diagnostic PCR of individual colonies. The number of inserts of the correct size was 89% and the number of colonies calculated to be 9×10$^7$ resulting in a diversity of ~8×10$^7$ different clones carrying an insert of correct size. Once the culture reached OD$_{600}$=0.4 the culture was then infected with approximately 5×10$^{12}$ pfu VCS-M13 helper phage (Stratagene), left for 20 min at 37° C. without agitation, and then shaken for 1 hour. Kanamycin was added to a final concentration of 50 ug/ml culture and the culture was grown overnight at 37° C. Bacteria were sedimented and phage precipitated overnight at 4° C. after dissolving in 20 g PEG8000 (Sigma) and 15 g NaCl. Phage were pelleted by centrifugation, dissolved in 5 ml PBS, filtered through 0.45 filters and used for panning.

Preparation of Biotinylated RNA Target

Generation of biotin labeled asp-tRNA was carried out by in vitro transcription using the MEGAscript kit (Ambion, USA) and the Biotin RNA Labeling mix (Roche, Switzerland) containing biotin-16-UTP. The DNA template was made on the basis of expression-PCR (41) by PCR assembly of synthetic oligonucleotides covering the 78 bp asp-tRNA gene from P. aerophilum (Gene_ID: 1464263) and a 150 bp DNA fragment amplified from pET28 (Invitrogen) including the T7 promoter region at the 3' end followed by GG for optimal promoter activity according to recent promoter recognition studies for T7 (42). This resulted in an assembled product of 230 bp which was precipitated by ethanol, dried, resuspended in RNase-free H$_2$O and used as the template for transcription without further cloning (41). In vitro transcription was carried out following the manufacturer's manual (Ambion) and yielded ~5 ug biotinylated asp-tRNA from a 25 ul reaction.

Selection of aspRS-OB Libraries

Biotinylated asp-tRNA was used as a target in the selection from the libraries 'RL' and '13mRL', and hen egg lysozyme (Roche, Switzerland) was used for selection from '13mRL' only.

For selection on RNA, biotinylated asp-tRNA was immobilised by binding to streptavidin coated paramagnetic beads. 10 ul beads were washed twice with 400 ul PBS-T (PBS, 0.1% Tween) and incubated with 100 ng biotinylated asp-tRNA for 30 min at RT with agitation and occasional inverting. Beads were washed 3 times with PBS-T before incubation for 2 hours with 1 ml of ~10$^{11}$ cfu phage library RL or 13mRL in PBS-T+0.5% BSA. After 6 washes with PBS-T for the first round of panning and 8 washes for the subsequent panning rounds, beads were washed 2 more times with PBS and incubated with 1 ug (5 Kunitz units) RNase A (from bovine pancrease, Roche) for 30 min at 37° C. to digest RNA and elute RNA-bound phage. Eluted phage particles were counted by bacterial infection and used for infection of 3 ml of a fresh TG1 culture for TDP production for the next round of panning. Cultures were left for 20 min at 37° C. without agitation, incubated for one hour with shaking before addition of ampicillin and grown overnight. Overnight cultures were used to inoculate 500 ml prewarmed LB/Amp. Helper phage infection and TDP production followed the same procedure as for the phage library preparation outlined above. After 4 rounds of panning individual clones were analyzed.

For selection on lysozyme, 4 ml Immuno Tubes (Nunc, Denmark) were coated with 2.5 ml lysozyme solution (10 ug/ml) in 20 mM NaCO$_3$ pH 9.0 overnight at 4° C. and blocked with 4 ml 1% BSA in PBS for 1 hr at RT. Phage from library 13mRL were added (~2.5×10$^{11}$ cfu in 2.5 ml) and incubated for 2 hrs at RT with gentle agitation and occasional inversion. Washing was performed quickly within 5 min by 8 washing steps with PBS-T 0.1% BSA (for the first round of selection only 6 washes were performed using PBS-T) and 2 steps with PBS. Bound phage were eluted by incubation for 10 min with 2.5 ml elution buffer (0.2M glycin-HCl pH2.2, bromphenol blue) and immediately neutralized using 500 ul 1 M Tris-HCl pH 9.0. Eluted phage were counted and used to infect a fresh 3 ml TG1 for TDP amplification and subsequent rounds of panning. Culture growth and TDP production were carried out in the same way as described above for panning on asp-tRNA. After 6 rounds of selection and amplification clones were picked and analyzed.

Western Blot for Phage Display Protein Detection

A phage sample of aspRS-OB was concentrated by PEG precipitation to $1 \times 10^{11}$ TDP/ml and 10 µl combined with gel loading buffer (contained SDS and BME), boiled and separated on a 10% SDS-PAGE gel. After transfer onto a nitrocellulose membrane (Protran, Schleicher & Schuell, Germany) aspRS-OB-pIII fusion protein was detected using a mouse anti-c-myc primary antibody (Zymed, Invitrogen) and a HRP-linked anti-mouse secondary antibody (Amersham-Pharmacia, Sweden). Visualisation was performed using SuperSignal® substrate (Pierce, USA).

Phage ELISA

Phage ELISA experiments were performed to analyse selected clones for binding to lysozyme. Ninety-six-well ELISA plates were coated with 5 ug/ml hen egg lysozyme, 5 ug/ml RNaseA or 1% BSA in PBS at 4° C. overnight. After two washes with TBS, plates were blocked with blocking buffer (5% skim milk in TBS) for one hour at RT before phage ($10^9$ cfu/well, derived from VCS-M13d3) were added in 2.5% skim milk-TBS-T. Plates were incubated for 2 hours at RT with agitation. After 10 washes with $H_2O$, mouse anti-M13 protein VIII diluted in blocking buffer was added and incubated for 1 h at RT. Plates were washed 4 times with $H_2O$ and horseradish peroxidase (HRP)-coupled rabbit-anti-mouse immunoglobulins (Pierce) in blocking buffer were added to the wells and incubated for 1 h at RT. Wells were washed 4 times with $H_2O$ and 50 ul substrate solution (1 mg/ml o-phenylene-diamine in PBS 0.030% $H_2O_2$) was added per well. The reaction was stopped after ~15 min by addition of 25 ul 2.5 M $H_2SO_4$ and the absorbance was recorded at 492 nm.

For relative phage quantification (quantification of displayed fusion protein) phage samples were used directly to coat plates. After blocking with blocking buffer, phage were detected using mouse anti-c-myc primary antibody (Zymed, Invitrogen) and an HRP-conjugated anti-mouse secondary antibody following the procedure described above.

Monoclonal Phage Preparations

For phage binding experiments monoclonal phage samples were prepared as multivalent display using a gIII deletion variant of VCS-M13d3 (Vd3) (Rakonjac et al, 1999) as helper phage. For the micropanning prescreen monovalent phage were used derived from wtVCS-M13. Helper phage VCS-M13 and Vd3 stocks were prepared from single plaques following general protocols (Barbas III et al. 2001) with the exception that VCS-M13 was grown on TG1, Vd3 on E. coli K1762 (K561 transformed with plasmids pJARA131 (cam$^r$) and pJARA112 (amp$^r$)) was used as a host strain to supply pill for phage assembly. Vd3 samples were heated at 65° C. for 20 min to kill λ-lysogen from the bacterial host.

To prepare stocks of phage aspRS-OB on Vd3 or VCS-M13, E. coli TG1 transformed with the corresponding pRPSP2 derivative were grown in 100 ml LB/Amp to $OD_{600}$=0.4 and infected with $10^{12}$ pfu Vd3 or VCS-M13 respectively. After 20 min incubation at 37° C. without agitation, the culture was incubated for another hour with shaking. Kanamycin (50 ug/ml final concentration) was added and the culture was incubated overnight. Cells were sedimented and phage purified by precipitation using PEG/NaCl following current protocols (Barbas III et al.) and as discussed above. TDPs were resuspended in PBS and used for analysis.

Monoclonal Phage Binding Experiments on asp-Trna

For testing binding of phage displayed protein to asp-tRNA, monoclonal phage samples were used displaying the fusion protein in a multivalent fashion on Vd3. The procedure carried out was essentially as that for the first round of selection outlined above. Biotinylated asp-tRNA was bound to streptavidin coated paramagnetic beads and TDP samples were applied ($10^9$ cfu/tube). After incubation and washing steps RNA was digested by addition of RNaseA and eluted TDP were counted by bacterial infection.

GST 'Pull Down' Assay

Mutants selected on lysozyme were subcloned into GATAWAY® pDEST15 for expression as GST-fusion proteins. Constructs were transformed into E. coli BL21 (DE3) and cultures were grown in 3 ml LB/Amp. Cells were induced by addition of IPTG to a final concentration 1 mM and grown for another 4 hrs at 37° C. Cells were sedimented, resuspended in 300 ul lysis buffer (Tris-HCl 7.5 150 mM NaCl) and lysed by sonication. Insoluble material was sedimented and the soluble fraction was incubated with 10 ul glutathion-linked sepharose beads (Amersham) for 1 hr at 4° C. After two washing steps with TBS-T, beads were incubated with 300 ul TBS-T including 150 ul lysozyme (1 mg/ml) and 0.1% BSA for 1 hr at 4° C. Washing was performed using different buffers: TS (50 mM Tris-HCl pH7.5, 150 mM NaCl), TBS-T (20 mM Tris-HCl pH7.5, 150 µM NaCl, 0.1% Tween20), TBS-T-500 (TBS-T, 500 mM NaCl). Beads were resuspended in gel loading buffer (containing SDS and BME), boiled and analyzed by SDS-PAGE.

Biosensor Binding Analysis

The ligand lysozyme was coupled to a CM5 Biacore sensor chip, at 30 µg/mL in sodium acetate buffer at pH 4.3 via the primary amine groups of the protein. The second of four flow cells available on the chip was activated with 35 µL, at 5 µL/min, of a 1:1 mixture of EDC:NHS (commercially available from Biacore). Lysozyme was coupled to the activated surface with successive injections of between 10-20 µL, until an adequate response was seen. Remaining uncoupled active groups on the chip were deactivated with an injection of ethanolamine-HCl. For analysis, OB3 13mRL L6 was organized in a 1:2 dilution series of six concentrations, beginning at 370 µM in running buffer, plus a buffer-only blank. Each of the seven samples were analyzed in duplicate for 1 min @ 25 µL/min, in random order, using the first flow cell as a reference. The response curves were visualized and processed using BIAevaluation (Biacore). Relative response at each concentration was averaged and plotted to determine Rmax and kD using Sigma Plot (Systat Software, Inc.).

Example 2

OB-fold Domains from Pyrobaculum aerophilum

To study whether OB-fold domains can be used as a scaffold for generating proteins with specific binding and enzymatic properties, the tolerance of individual OB-fold domain proteins toward mutations across the proposed binding face was studied. Two OB-fold domains from Pyrobaculum aerophilum, a hyperthermophilic crenarchaea ($T_{max}$=104° C., $T_{opt}$=100° C.) were selected. This choice was made following a database search using the Superfamily database (version 1.65 (46)) to find OB-fold proteins in the P. aerophilum genome (42). This database uses a library of all proteins of known structure which have been clustered into 1294 SCOP superfamilies (SCOP: Structural classification of proteins) to develop hidden Markov models which are then used as profiles to search sequenced genomes for proteins likely to contain similar folds. This search yielded 14 hits representing protein sequences containing potential OB-fold domains from the genome of P. aerophilum IM2.

Each of these sequences were analyzed to find OB-fold proteins which are spatially separated from other domains and thus expected to be independently stable. The sequences were also aligned to a 3-dimensional model representing the superfamily or to available, homologous, three dimensional protein structures, to check the reliability of the OB-fold prediction from the sequence. Of these 14 sequences, 8 fulfilled the criteria (see Table 2). Six of the eight candidates belonged to two functional classes of RNA binding proteins: translation initiation factors (IF) and aminoacyl-tRNA synthetases (aaRS). Two candidates had no functional annotation and were classified as "conserved hypothetical proteins."

The OB-fold domains from the chosen sequences were cloned. The domain boundaries were identified from sequence alignments and tested for expression and solubility in *E. coli*. OB-fold domains from the aspartyl tRNA synthetase (aspRS-OB) and from the translation initiation factor IF-5A (IF5A-OB) were initially chosen since they expressed well and were soluble and heat stable.

An additional advantage of the IF-5A protein was the availability of the high resolution 3-dimensional structure in the Pfam DataBase (34) from which surface exposed residues could be reliably chosen for randomisation. This structure of IF-5A (FIG. 3) shows two domains with the OB-fold at the C-terminus and spatially separated by a linker region, thus satisfying our selection criteria. The proposed binding face (β-strands 1-3) is directed away from the protein centre and toward the solvent. The OB fold of IF-5A has a shear number of S=8 and is thus, a representative of one sub-class of the OB-fold domains.

Figure 4:
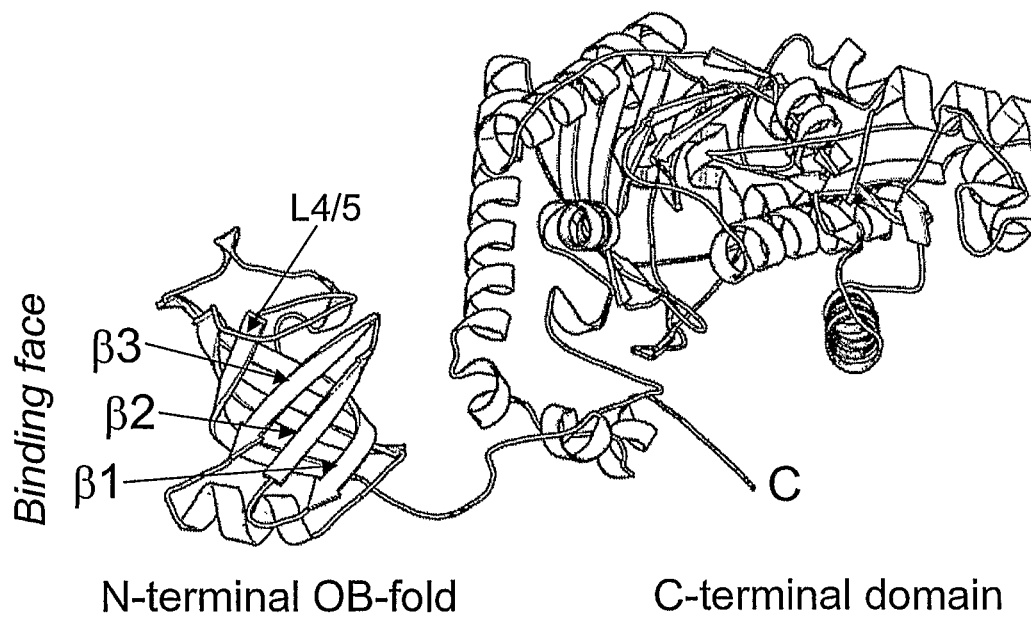
FIG. 4 illustrates the crystal structure of *E. coli* asp-tRNA synthetase (1C0A, (37)). This schematic ribbon diagram shows the structure of aspRS showing the relationship between the OB-fold and the C-terminal enzymatic domain. β-strands and α-helices are shown as arrows and helical ribbons, respectively. The binding face is indicated (36) comprising β-strands 1-3 and the loop 4/5 between β-strands 4 and 5.
Figure 7:
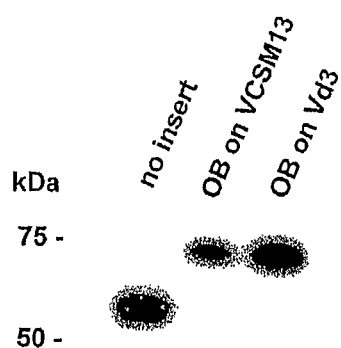
FIG. 7 is a Western analysis of phage displayed aspRS-OB. Left lane (no insert) represents pIII only as empty vector pRPSP2 was used to prepare TDPs; centre lane shows aspRS-OB fused to pIII displayed on VCSM13; right lane aspRS-OB on gIII deletion phage Vd3. $10^{11}$ TDPs were boiled in presence of SDS and BME and separated by 10% SDS-PAGE followed by transfer to a 0.45 um nitrocellulose membrane. Detection was performed using a mouse anti-c-myc antibody and a HRP-conjugated rabbit anti-mouse antibody.

The OB-fold domain of asp-tRNA synthetase (aspRS-OB) was chosen as a representative of the second sub-class of OB-fold proteins with the property, S=10. A three dimensional structure of aspRS from *P. aerophilum* is not available, however there are a number of structures in the PDB for aspRS proteins from other organisms. FIG. 4 shows the crystal structure of aspRS from *E. coli* (37). A sequence alignment for the OB-fold domain from *P. aerophilum* aspRS and its *E. coli* homologue show that the OB-fold domains have a sequence identity of 30%. Over their full lengths the aspRS proteins are 20% identical at the sequence level. The OB-fold lies at the N-terminus and is clearly spatially separated from the larger C-terminal domain. The binding face points away from the C-terminal domain toward the solvent. While the N-terminal OB-fold domain binds to tRNA and constitutes the anticodon recognition domain, binding specifically the aspartyl-tRNA anticodon (36), the C-terminal domain constitutes the enzymatic component of the protein. Table 2 shows eight selected sequences from *P. aerophilum* with predicted OB folds. NP accession numbers are given along with the predicted size and the proposed shear number. The 3-dimensional structure is available for IF-5A. The predicted size for the conserved hypothetical protein, NP_559846, corresponds to the whole protein. In this case, the boundaries of the OB-fold domain are difficult to accurately predict.

TABLE 2

| Protein annotation containing predicted OB-fold | NP number | size of OB fold | shear number (S) |
|---|---|---|---|
| translation initiation factor IF-5A | (NP_560668) | 10 kDa | 8 |
| translation initiation factor IF-2 alpha subunit | (NP_560442) | 12 kDa | 8 |
| translation initiation factor IF-1A | (NP_559055) | 14 kDa | 8 |
| aspartyl-tRNA synthetase | (NP_558783) | 15 kDa | 10 |
| asparaginyl-tRNA synthetase | (NP_560397) | 14 kDa | 10 |
| lysyl-tRNA sythetase | (NP_559586) | 18 kDa | 10 |

TABLE 2-continued

| Protein annotation containing predicted OB-fold | NP number | size of OB fold | shear number (S) |
|---|---|---|---|
| conserved hypothetical protein | (NP_560727) | 11 kDa | — |
| conserved hypothetical protein | (NP_559846) | 29 kDa | — |

Each of these OB-fold domains have homologues in all kingdoms offering opportunities for applications in a different physiological contexts (see FIGS. 5A-5B for sequence alignments of aspRS (FIG. 5A) and IF-5A (FIG. 5B) from different species). FIG. 5C shows the sequence alignment of aspRS-OB from *P. aerophilum*, *P. kodakaraensis*, and *E. coli*. Sequence identities are indicated by asterisks. The secondary structure of the OB-fold is indicated below the sequence: 1+loop between strands 4 and 5, loop 4/5.

Example 3

Choice of Residues for Randomization

The residues for randomization of the two OB-fold domains were chosen on the basis of their three dimensional structures. The structure for IF-5A is available. A structure for the OB fold of aspRS from *P. aerophilum* was generated by modelling using Swiss Model (38-40) and the available structures from *E. Coli* (36,37) and *Pyrococcus kodakaraensis* (35) as structural templates.

On the binding face of the OB-fold domains, surface exposed residues were chosen from β-strands 1-3. Since aspRS and IF5A OB-fold domains have different shear numbers, their structures are slightly different. In particular, the arrangement of the β-strands 4 and 5 along with the loop between these strands is different. In the case of aspRS-OB, the loop between strand 4 and 5 was also included for randomization in one of the libraries. Thus, for aspRS-OB, 13 solvent exposed residues situated on β-strands 1-4 and in the loop between strands 4 and 5 were chosen for randomization. This gives a maximum number of 17 mutation sites and a theoretical variability of $20^{17}=1.3 \times 10^{22}$ possible mutants.

To assess the tolerance to such mutations, a set of libraries were constructed addressing parts of the binding face independently. For IF5A-OB, libraries were constructed which randomized either 9 or 11 positions on β-strands 1-3 (FIG. 8) resulting in two libraries with calculated theoretical variation of $20^9=5.12 \times 10^{11}$ and $20^{11}=2 \times 10^{14}$ variants respectively. Two small libraries (400 variants each) were generated targeting the loop between strands 1 and 2 by randomising two introduced residues, serine-asparagine (2RL) or, by extending the loop using a further two residues (2RL+2). For details of the residues chosen and their locations in the OB-fold domains see FIGS. 8 and 9.

Example 4

OB-fold Libraries

A set of libraries addressing defined regions of each OB-fold domain were constructed. For aspRS-OB-fold domain, the β-strands were mutated individually and in combination with each other. The loop between strands 4 and 5 was separately randomized in the wild type OB-fold domain (that is, the naturally occurring OB-fold domain) and in a fully randomized library. As a result, five libraries of different sizes and different arrangements of randomized positions were constructed (see Tables 3A-3B).

For IF5A-OB, the β-strands 1-3 as well as the loop between strand 1 and 2 were targeted for randomisation. This loop (between strands 1 and 2) was targeted for randomisation to assess its potential to extend the randomized surface area. There are examples of naturally occurring OB-fold proteins which show extended loops in this region which suggests that this loop might be amenable to extension. In a similar approach used for aspRS-OB-fold domains, libraries with different sets of mutations (see Table 3) were assembled by PCR, cloned into an expression vector and expressed in *E. coli*. Clones representing library members carrying mutations were picked and analyzed for inserts of correct size, expression as a His$_6$-tagged protein, solubility and binding to Ni-NTA-resin.

TABLE 3A

| aspRS-OB library | randomized area | theoretical size of library | number of mutations |
| --- | --- | --- | --- |
| 4m | β3 | $20^4 = 1.6 \times 10^5$ | 4 |
| 9m | β1-2 | $20^9 = 5.1 \times 10^{11}$ | 9 |
| 13m | β1-3 | $20^{13} = 8.2 \times 10^{16}$ | 13 |
| 4RL | Loop 4/5 | $20^4 = 1.6 \times 10^5$ | 4 |
| 13m4RL | β1-3 + loop 4/5 | $20^{17} = 1.3 \times 10^{22}$ | 17 |

TABLE 3B

| IF5A-OB library | randomized area | theoret. size of library | number of mutations |
| --- | --- | --- | --- |
| 9m | β1-3 | $20^9 = 5.1 \times 10^{11}$ | 9 |
| 11m | β1-3 | $20^{11} = 2.0 \times 10^{14}$ | 11 |
| 2RL | Loop 1/2 | $20^2 = 400$ | 2 |
| 2RL + 2 | Loop 1/2 | $20^2 = 400$ | 2 |

Tables 3A-3B are a list of gene libraries for aspRS-OB. Suffix 'm' indicates mutation in the β-sheet covering β-strands 1-3. Suffix 'RL' indicates the randomized loop region (Loop 4/5 in case of aspRS-OB and Loop 1/2 in case of IF5A-OB).

Example 5

Library Assembly

Libraries were essentially assembled on the basis of overlap extension PCR incorporating synthetic oligonucleotides with degenerate codons at the desired positions. First, gene fragments covering the whole gene and containing overlapping regions were generated by ordinary PCR techniques. Randomized fragments were generated by incorporation of the corresponding long oligonucleotides containing randomized codons. Fragments were assembled by PCR using equimolar amounts of these gene fragments in combination with primers flanking the gene resulting in amplification of the full length gene incorporating the randomized positions. Using different combinations of degenerate oligonucleotides several libraries containing random mutations in different areas of the binding face were generated. Diversity was created in aspRS-OB at residues on the beta sheet W28, E29, R31, I33, R35, V36, F38, V40, R42, F47, Q49, T51, K53 and in the loop region I85, A86, K87, S88. Library RL (randomized loop) contains 4 randomized positions in the loop region between beta strand-4 and 5. The theoretical diversity for the RL library is $20^4 = 160000$ different variants. After transformation, library RL contained ~$10^7$ clones, of which 94% had an insert of correct size resulting in a full coverage of the diversity of the library. The theoretical diversity of 13mRL is very high with ~$5 \times 10^{22}$ variants. $10^8$ clones were obtained after transformation with 89% correct inserts. Out of 10 sequenced clones 8 had desired mutated sequences whereas 2 clones had frameshifts which would result in non-sense translation. The overall diversity was estimated to be ~$8 \times 10^7$ variants in the 13mRL library.

Libraries for IF5A-OB were generated individually. "9m" and "11m" libraries each have a different pair of long oligonucleotides incorporated into the gene. For the 11 m library, the loop 1/2 was extended by 4 amino acids (Ser-Asn-Gly-Ala) (SEQ ID NO:79) to provide a sufficient overlap of the randomized fragments. For the small libraries 2RL and 2RL+2, randomized sites within the loop region were generated using one oligonucleotide containing randomized positions incorporated into the gene covering the corresponding region. Diversities of IF-5A libraries with 9 and 11 mutations were estimated to be $1 \times 10^7$ variants, the theoretical diversity of the small libraries (400 variants) were fully covered.

Example 6

Expression of OB-fold Mutant Proteins

Both naturally occurring OB-fold domains expressed well in *E. coli* (10-20 mg.l$^{-1}$ of culture) and are predominantly soluble after cell lysis. These remain soluble after heat treatment (15 min at 85° C.) and bind quantitatively to Ni-NTA beads. The OB-fold libraries were cloned and expressed as N-terminal His$_6$-tagged proteins. A set of protein characteristics were recorded addressing protein stability and structural integrity.

PCR libraries were cloned into an expression vector with an efficiency of 90-95% (determined by colony PCR) and genes were expressed as polyhistidine fusion proteins in *E. coli*. 48 or 96 colonies were screened for expression, solubility and Ni-binding. The results are summarized in Table 4.

TABLE 4

| Fragment | sense oligo | antisense oligo | Template | Gene fragment | mutations | Fragment Size |
| --- | --- | --- | --- | --- | --- | --- |
| 13m library ||||||||
| 1 | 005 | 054 | aspRS-OB wt | N-term | — (wt) | 80 bp |
| 2 | 059 | 006 | aspRS-OB wt | C-term | — (wt) | 180 bp |
| 3 | 051 055 | 056 056 | no template | β-strands 1 & 2 | 9 | 80 bp |
| 4 | 057 057 | 058 052 | no template | β-strand 3 | 4 | 50 bp | assembly 13m library: fragments 1-4

TABLE 4-continued 4m and 9m libraries

4m

| | | | | | | |
|---|---|---|---|---|---|---|
| 1 | 005 | 056 | aspRS-OB wt | N-terminal portion incl. β1-2 | — (wt) | ~140 bp |
| 2 | Fragment 1 | 052 | — | N-terminal portion incl. β1-3 | 4 mutations in β3 | ~180 bp |
| 3 | 059 | 006 | aspRS-OB wt | C-terminal portion incl. β1, β4-5 | — (wt) | ~180 bp | assembly 4m library: fragments 1-3

9m

| | | | | | | |
|---|---|---|---|---|---|---|
| 1 | 005 | 056 | aspRS-OB 13m library | N-terminal portion incl. β1 + 2 | 9 in strand 1 + 2 | ~150 bp |
| 2 | 068 | 006 | aspRS-OB wt | C-term incl. β3-5 | — (wt) | ~200 bp | assembly 9m library: fragments 1-2

4RL and 13m4RL libraries

| Fragment | sense oligo | antisense oligo | Template | Gene Portion | mutations | Fragment Size |
|---|---|---|---|---|---|---|
| 1 | 005 | 060 | aspRS-OB wt | N-terminal portion incl. B-strand 1-4 | — (wt) | ~250 bp |
| 2 | 005 | 060 | aspRS-OB 13m library | N-terminal portion incl. B-strand 1-4 | 13 mutations in β-sheet | ~250 bp |
| 3 | 053* 061 | 063 063 | no template | loop4/5 + β-strand 5 | 4 mutations in L4/5 | ~60 bp |
| 4 | 062 | 006 | aspRS-OB wt | C-term | — (wt) | ~70 bp | assembly 4RL library: fragments 1 + 3 + 4
assembly 13m4RL library: fragments 2 + 3 + 4

Summary of the library construction for aspRS-OB is shown in Table 4. For each library the PCR generated gene fragments, oligonucleotides and templates are listed. Gene fragments were generated by PCR incorporating oligonucleotides. PCR products were then assembled to the full length gene by overlap extension PCR using gene flanking primers (oligos 005 and 006). Also, see FIGS. 2A-2B. Approximately half of the clones from all libraries of aspRS-OB expressed well in E. coli. The number of randomized positions on the β-sheet (i.e., the number of amino acid positions on the binding face that were randomized in order to construct the library) appeared to correlate with the percentage of expressing variants. For both libraries with 13 mutations, 13mRL and 13 m, ~45% of the mutant proteins express well. The library containing 9 mutations on β-sheets 1 and 2 show expression in 52% of the clones. The library which targets only loop 4/5 for randomisation had a very high number of expressing clones at 81%. However, the combination of randomized positions on both the face and the extended loop (13mRL+2) dropped the number of expressing clones to just 30%.

In the case of IF5A-OB, libraries with mutations on the β-sheet were expressing at a comparatively low rate, 12%, and of these, 9-25% were soluble. In contrast, 72-81% of the mutants containing randomized positions in just loop 1/2 only, were expressed and, of these, ~70% were soluble. All IF5AOB mutants were heat treated at 80° C. after lysis. Thus all the soluble and Ni-binding mutants were also heat stable.

A few mutants were picked for preparative expression and purification. In addition, the large scale purification of an aspRS-OB mutant was also performed. Table 5 shows the summary of expression, solubility and Ni-NTA-binding experiments.

TABLE 5

| OB fold | library | screened | expression | express./screen. [%] | solubility | (%) | Nickel binding |
|---|---|---|---|---|---|---|---|
| aspRS | 13m4RL | 48 | 21 | (44) | 3/10 | (30) | 2/2 |
| | 13m | 96 | 43 | (45) | 6/14 | (43) | 5/5 |
| | 9m | 48 | 25 | (52) | 4/8 | (50) | — |
| | 4m | 48 | 38 | (79) | — | — | — |
| | wtRL | 48 | 35 | (73) | — | — | — |
| IF-5A | 9m | 192 | 21 | (11) | 2/21 | (9) | 2/2 |
| | 11m | 144 | 16 | (11) | 4/16 | (25) | 4/4 |
| | 2RL | 32 | 26 | (81) | 20/26 | (77) | 13/16 |
| | 2RL + 2 | 32 | 23 | (72) | 18/26 | (69) | 14/18 |

Between 32 and 192 colonies for each library were screened for expression, solubility and binding to Ni-NTA. Table 5 shows the number of expressing clones, the calculated ratio of expressing clones for each library, and presents an estimation of the solubility and Ni-NTA binding properties of expressing OB-fold mutants.

Example 7

Analysis of Phage Displayed aspRS-OB

An important criteria for a protein domain as a scaffold for library generation is its capacity to be functionally displayed in a chosen display system. The experiments disclosed herein used phage display. To assess the viability of this technique for selection of aspRS-OB mutants the display of recombinant wild type aspRS-OB as gIII fusions on the surface of filamentous bacteriophage M13 was assessed. The presence of a pIII-aspRS-OB fusion in prepared phage particles by Western blotting was analyzed. Functional display of displayed aspRS-OB was studied by a phage binding assay using asp-tRNA as the target ligand.

The gene for wild type aspRS-OB was cloned into phagemid vector pRPSP2 upstream of the gIII gene generating a fusion protein with aspRS-OB at the N-terminus and pIII at the C-terminus (see FIG. 6). This phagemid vector contains gIII under the control of the phage shock promotor (psp) which is activated upon infection of the E. coli host by helper phage (31). Helper phage VCS-M13d3, gIII deletion mutant (44) was used which allowed multivalent display of the target protein. All copies of gIII proteins (3-5 copies) will be fusions to the target protein aspRS-OB. Multivalent display was used to increase sensitivity in binding assays (48).

The construct, pRPSP2 containing the gene for aspRS-OB was transformed into E. coli TG1 cells. The resulting culture was infected by the Vd3 helper phage and transducing particles (TDPs) were produced. These recombinant bacteriophage were harvested, tested for display of the target protein by western analysis using an antibody against the c-myc antigen sequence localized between the aspRS-OB and pIII (See figures infra). This showed a strong signal at the expected size for the fusion protein pIII-aspRS-OB.

To test whether the displayed wild type OB-fold is still functional on the surface of the phage, a phage binding experiment was performed to immobilised asp-tRNA with this phage sample displaying aspRS-OB. A TDP sample displaying aspRS-OB was incubated with asp-tRNA immobilised on magnetic beads. Unbound phage were washed away and bound phage eluted by tRNA digestion using RNaseA. The number of eluted phage were then counted by bacterial infection and compared with the number eluted from a sample incubated with beads only. To demonstrate specificity of binding, VCS-M13 wt in a >1000 fold excess was added to the TDP sample and the number of eluted particles was counted. The ratio of eluted phage from tRNA to input phage was calculated for each sample. The input and results are summarized in the following table.

TABLE 6

|  | VCSM13 | OB3wtTDP |
| --- | --- | --- |
| input | $3.0 \times 10^{12}$ | $1.7 \times 10^{9}$ |
| output from beads only | $1.2 \times 10^{9}$ | $2.1 \times 10^{5}$ |
| output from tRNA | $1.7 \times 10^{9}$ | $4.0 \times 10^{7}$ |
| beads only out/in | $4.0 \times 10^{-4}$ | $1.2 \times 10^{-4}$ |

TABLE 6-continued

|  | VCSM13 | OB3wtTDP |
| --- | --- | --- |
| tRNA out/in | $5.7 \times 10^{-4}$ | $2.4 \times 10^{-2}$ |
| quotient beads (out/in)/tRNA (out/in) | $7.1 \times 10^{-1}$ | $5.2 \times 10^{-3}$ |
| quotient tRNA (out/in)/beads (out/in) | 1.42 | 190.48 |
| TDP/VCS-M13 | 134.45 | |

Figure 8:
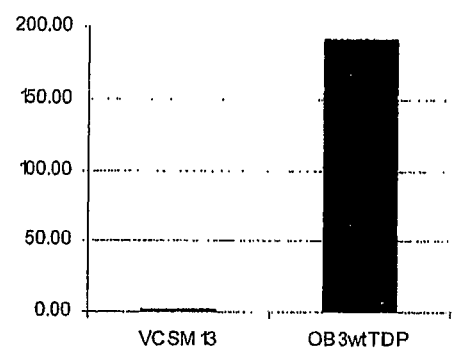
FIG. 8 shows a mock phage experiment with aspRS-OB displaying TDP and wild-type VCS-M13 phage to show functional display of wild-type OB fold from aspRS by binding to asp-tRNA. Immobilised tRNA was incubated with VCS-M13 (wild-type phage, no display) and aspRS-OB displaying TDP. The ratio of VCS-M13:TDP was >1000:1. After washing bound particles were eluted by RNA digestion by RNaseA. The recovery factor was calculated by dividing output and input for each VCS-M13 and TDP and for beads only or immobilized tRNA. See Table 6 for input and output data.

The recovery was about 200-fold higher for phage displaying the aspRS-OB ($2.4 \times 10^{-2}$) when compared to phage only ($5.7 \times 10^{-4}$, see FIG. 8). This indicated a significant affinity between the displayed aspRS-OB for the immobilised asp-tRNA. In the case of VCS-M13 without displayed protein, the ratio of eluted particles from the beads alone compared to immobilised tRNA was very similar (1:1.42) indicating that the phage bound non-specifically. That ratio was much higher (1:190.48) for aspRS-OB displaying particles demonstrating binding specificity of this domain for asp-tRNA. These results demonstrate that aspRS-OB is functionally intact when displayed on the surface of phage.

Example 8

Library Selections

Selection on asp-tRNA

Figure 9:
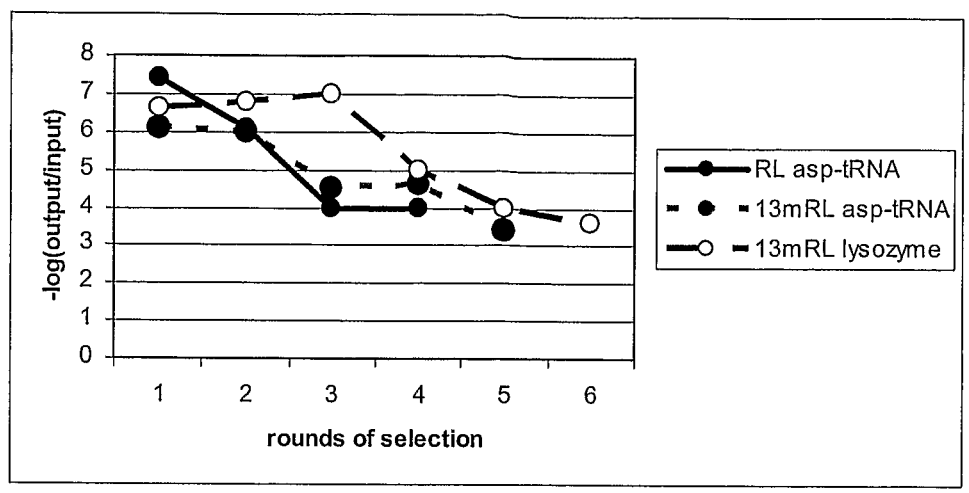
FIG. 9 is an enrichment (as-log(output phage/input phage)) of phage from round one to round six of selection of libraries RL (black circles, solid line) on asp-tRNA and 13mRL on either asp-tRNA (black circles, dotted line) or lysozyme (white circles, broken line)
Figure 16:
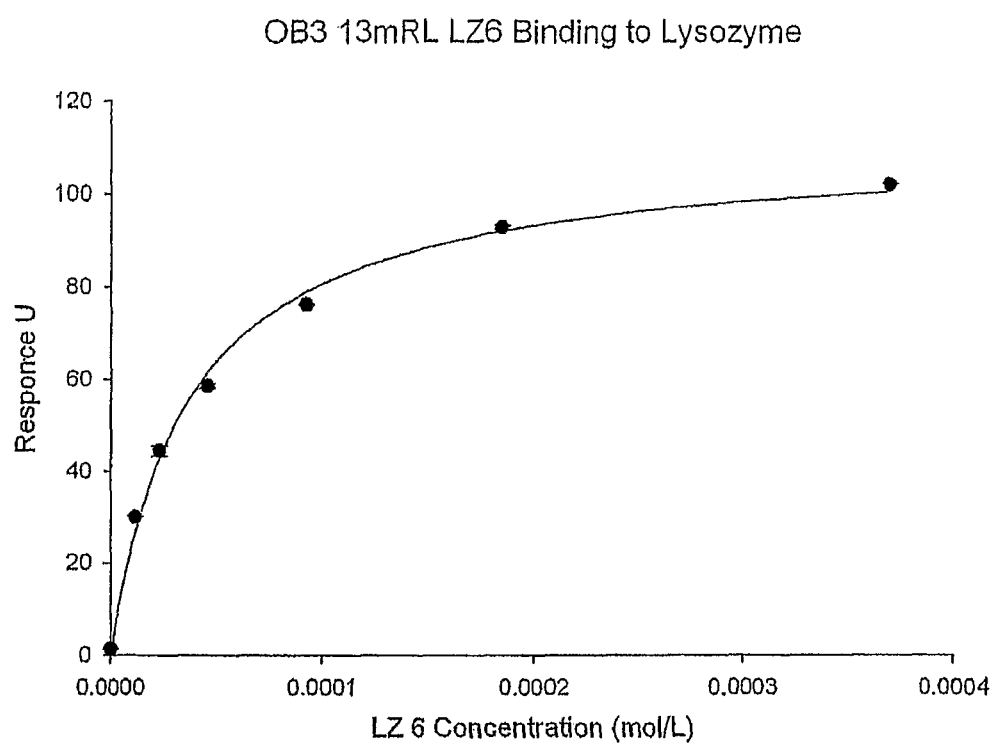
FIG. 16 shows a binding curve using surface plasmon resonance to determine the $K_d$ for binding between a selected OB-fold domain L6 and Lysozyme. The calculated $K_d$ from this experiment was $3.6 \times 10^{-5}$ M.
Figure 17:
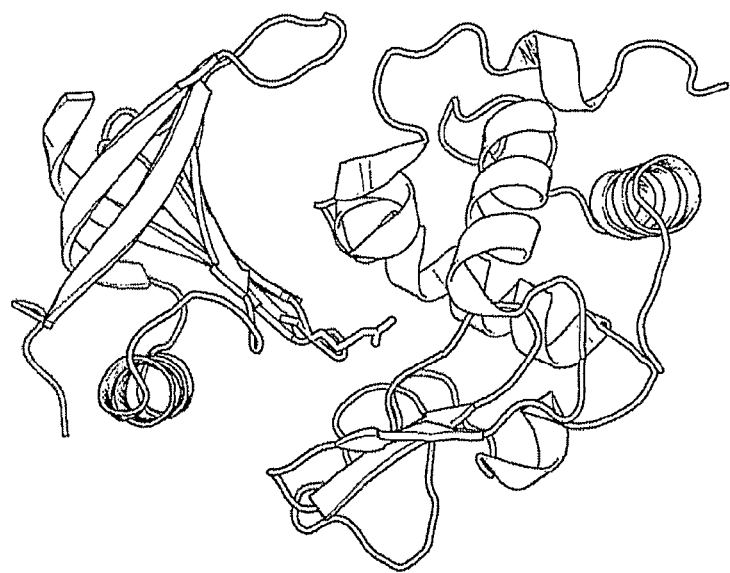
FIG. 17 shows the structure of the OBody-Lysozyme complex. The OBody is depicted as a cartoon (at left) showing secondary structure elements. Lysozyme is depicted as a cartoon (at right). Arg39 (from the OBody) is shown as sticks and points towards the active site of lysozyme. This residue forms hydrogen bonds with the active site acidic residues of lysozyme—Glu35 and Asp52 (see FIG. 20)
Figure 18:
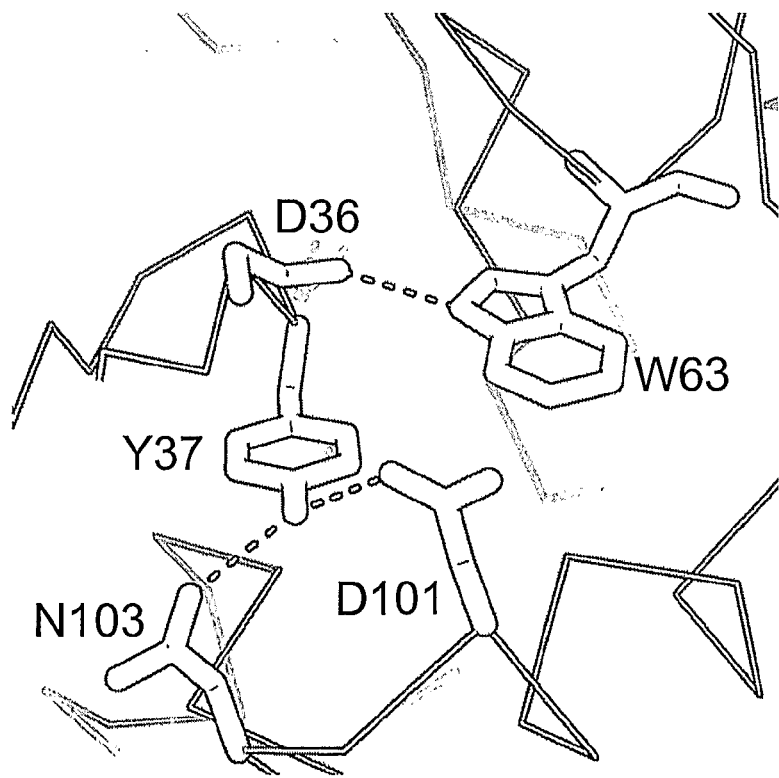
FIG. 18 shows examples of hydrogen bonding interactions at the protein-protein interface for the OBody-lysozyme complex. Residues are shown as sticks and are labelled (D36 and Y37 are from the Obody; W63, D101 and N103 are from lysozyme). Hydrogen bonds are depicted as dotted lines. Note that the H-bond from D36 to W63 is between the backbone carbonyl of D36 and the side-chain NH group of W63.
Figure 19:
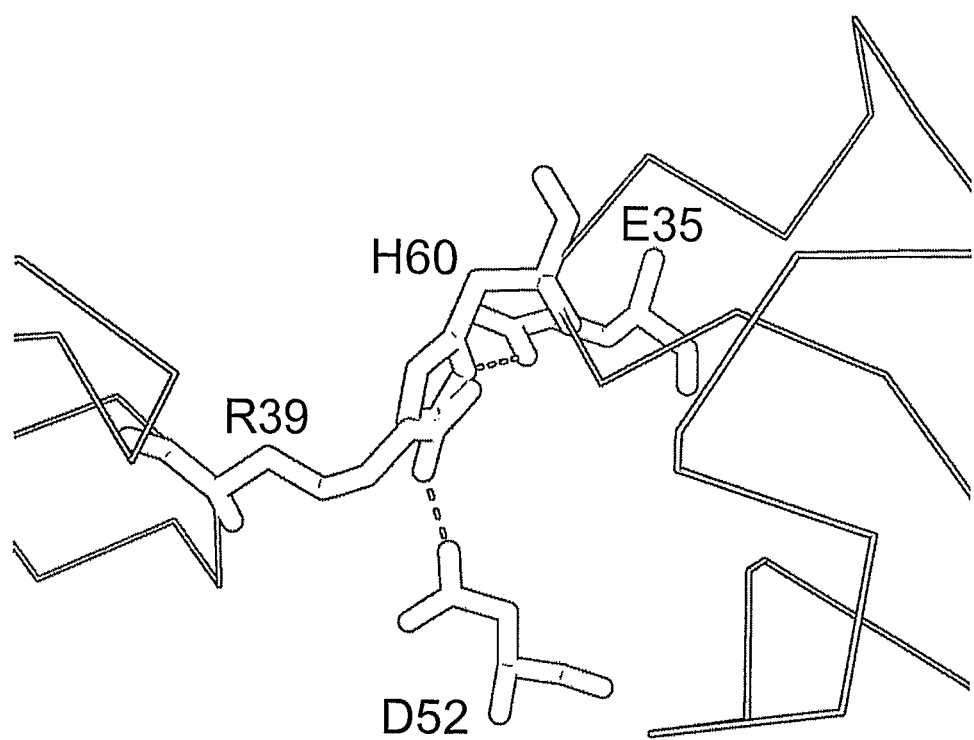
FIG. 19 shows the potential for OBody L8 to be a Lysozyme inhibitor. E35 and D52 are the active site catalytic residues for lysozyme and H60 is from the natural inhibitor of lysozyme. His60 makes hydrogen bond to lysozyme Glu35, thus inhibiting the enzyme. R39 from the OBody hydrogen bonds to both E35 and D52 in a similar manner. The backbone of the OBody and the natural inhibitor of lysozyme are depicted as C-alpha traces. The C-alpha trace for lysozyme is omitted for clarity.

The loop region between beta sheet 4 and 5 in bacterial aspRS anticodon-binding domains is important for binding to the tRNA as well as for specific recognition of the bases in the anticodon (49). Thus asp-tRNA was considered to be good target to test the viability of an aspRS-OB library. The library aspRS-OB RL was used since it contains full coverage of the theoretical diversity and therefore contains copies of the wild-type aspRS-OB fold sequence which was expected to bind well to the tRNA target. Even if none of the mutants bound to the tRNA, at least the wild-type should be selected by the biopanning process. An aspRS-OB RL gene library was generated as before, cloned into pRPSP2 yielding ~$10^7$ clones and monovalently displayed on phage. After four rounds of panning, a significant enrichment was observed as represented by the ratio of output phage to input phage—indicating an enrichment of target-specific binding domains (FIG. 9). Clones were randomly picked from the selected fraction and sequenced. The sequences showed the consensus R/K G C R (SEQ ID NO:75) for the 4 amino acids in the loop region for binding to asp-tRNA (FIG. 10). Of 12 sequenced clones, 5 fulfilled this consensus completely, 3 out of the remaining 7 agreed in 3 of the 4 amino acid positions. The consensus sequence is in striking contrast to the wild-type sequence (IAKS) (SEQ ID NO:67) which suggests that the new consensus sequence more strongly binds asp-tRNA in comparison to the wild-type domain. This was confirmed in a phage binding experiment with monoclonal phage preparations where two clones have higher affinity for asp-tRNA than wild type aspRS-OB (FIG. 16). For this experiment, phage displaying the corresponding mutant domains were incubated with immobilised asp-tRNA. Bound phage were specifically eluted with RNaseA and counted. The recovery rate R was calculated as [(output/input)$_B$/(output/input)$_{RNA}$] where (output/input) refers to the ratio of recovered phage (output) divided by the number of input phage, subscript 'B' refers to beads only, subscript 'RNA' refers to immobilised asp-tRNA.

Figure 11:
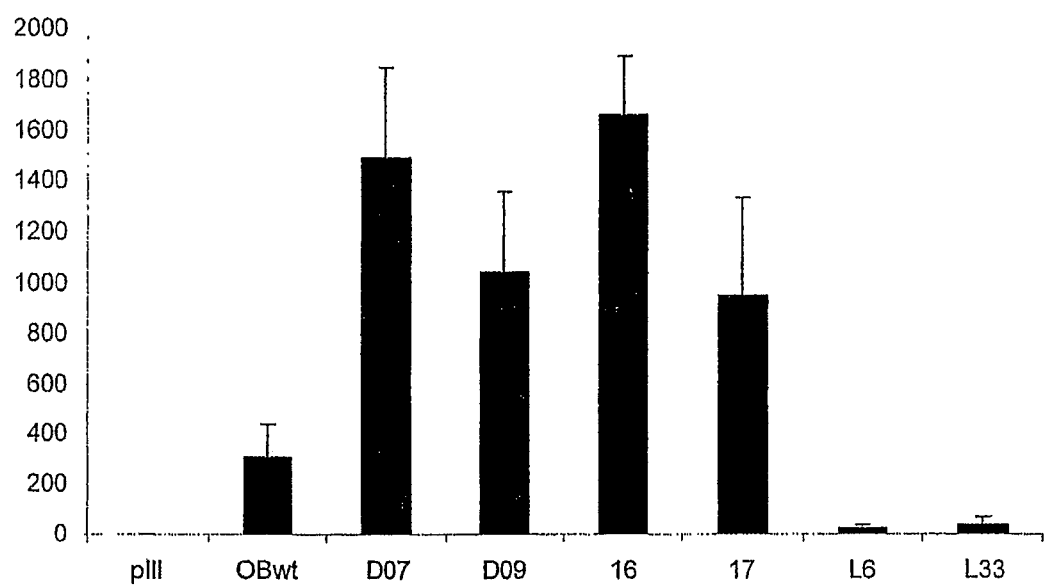
FIG. 11 shows an analysis of binding of selected clones to asp-tRNA by monoclonal phage binding experiments. Biotinylated asp-tRNA was immobilised on streptavidin coated magnetic beads and incubated with monoclonal phage samples. RNA-bound particles were specifically eluted by RNA digestion and counted by bacterial infection. The Y-axis shows a recovery factor which is calculated using the number of input phage, output phage from beads only and eluted phage from tRNA. Experiments were performed in duplicate, error bars represent±standard deviations. pIII: no fusion; OB3 wt=wild type aspRS-OB; D07, D09 mutants from 13mRL selected on asp-tRNA; 16, 17 were mutants pMB16 and pMB17 from aspRS-OB RL selected on asp-tRNA; L6 and L33 were mutants from 13mRL selected on lysozyme.

The results indicate that we have enriched a consensus sequence with enhanced binding affinity for immobilised asp-tRNA from a phage library derived from aspRS-OB mutants (FIGS. 10 and 11).

Selection was performed in the same manner against immobilized tRNA using the larger library '13mRL' which has much greater diversity compared to 'RL'. The enrichment pattern is shown in FIG. 9 and indicates significant enrichment after 5 rounds of panning. Sequence analysis is summarized in FIG. 12. Selected sequences contained a high proportion of positively charged amino acids suggesting those mutants were selected by binding to the negatively charged asp-tRNA backbone. The mutant with the greatest number of basic residues (D07) was found three times indicating a high abundance in the pool of selected clones. The phage binding experiment on immobilised asp-tRNA monoclonal phage samples prepared from the selected clones D07 and D09 showed that these clones were recovered in a number several times higher than the wild-type aspRS-OB domain suggesting stronger binding of the displayed mutant to asp-tRNA. These phage binding experiments are not precise measurements but indicate a successful selection process and demonstrate that aspRS-OB libraries can be used to select against an immobilised target using phage display. The full sequences of the selected clones in FIG. 12 are listed in Appendix II, and are designated U1, U2, U3, U4, U5, U6, U7, U8, U9, S68, S81, pMB16, pMB17, pMB12, pMB18, pMB15, D05, D07, D09, D04, L14, L8, L4, L16, L34, L42, L6, L5, or L44.

Example 9

Selection on Lysozyme

Figure 14:
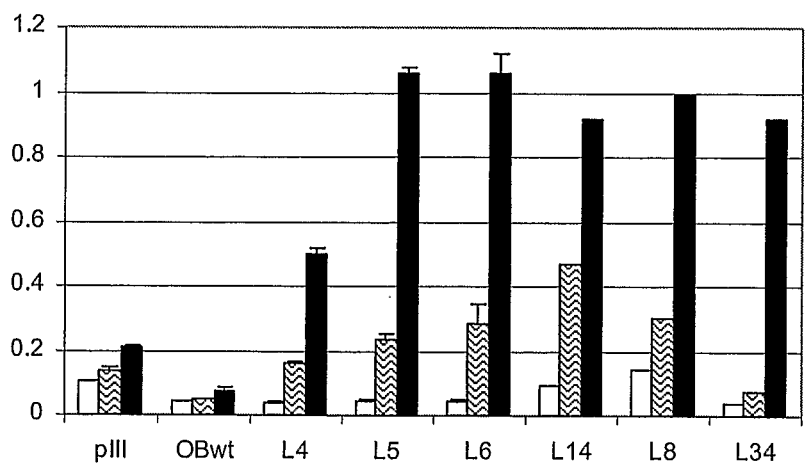
FIG. 14 shows analysis of binding of selected clones to lysozyme by ELISA. BSA (white), RNaseA (hatched) and hen egg white lysozyme (black) were immobilised and incubated with monoclonal phage samples. Bound particles were detected with a mouse anti-M13 primary antibody and an HRP-conjugated anti-mouse secondary antibody. Experiments were performed in duplicate, error bars represent±standard deviations. pIII: no fusion displayed, OBwt, wild-type aspRS-OB fold.
Figure 13:
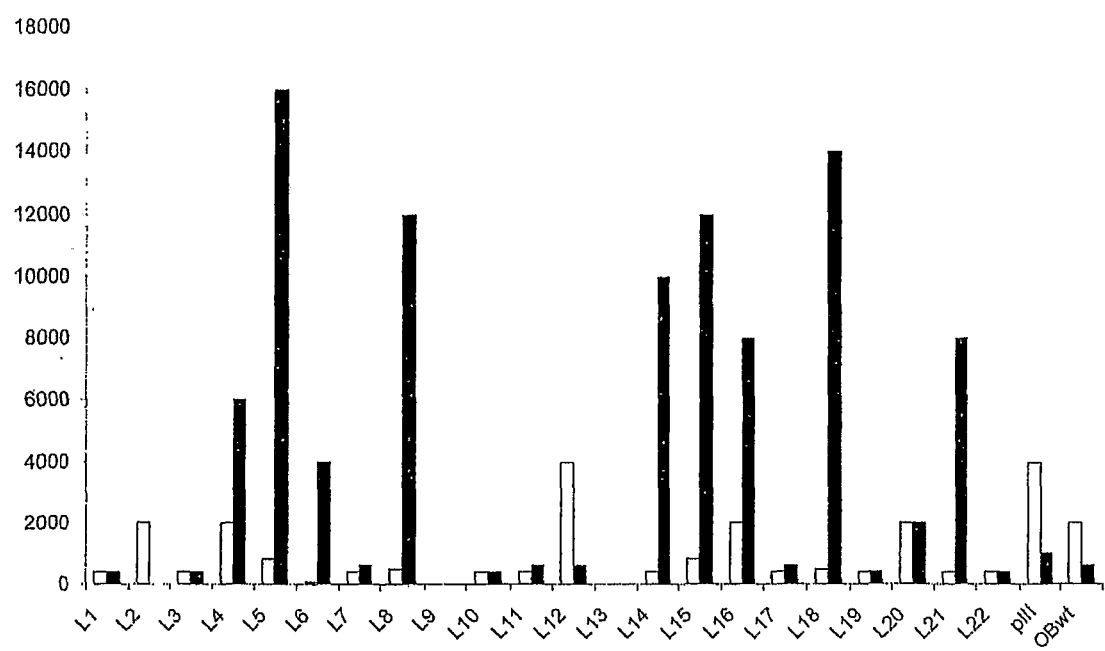
FIG. 13 shows a micropanning prescreen for binders to lysozyme. A 96-well plate was coated with lysozyme (black bars) or BSA (white bars) and incubated with monoclonal phage samples from clones picked after 6 rounds of selection. Bound phage were eluted and counted by bacterial infection. Numbers on Y-axis indicate the number recovered phage, on x-axis the clone numbers are shown, pIII indicates no fusion (empty vector) and OBwt the wild-type aspRS-OB displayed.

Lysozyme was selected as a target to demonstrate the proof-of-principle in choosing an OB-fold mutant domain from a naïve library which binds to another protein. Hen egg white lysozyme is a small stable protein which is commercially available and has a number of medically important human homologues. After four rounds of panning on immobilised lysozyme, enrichment of bound phage was observed. A further two more rounds of panning were performed before clones were randomly picked and screened for binding to lysozyme. Monoclonal phage samples were then prepared and studies were undertaken to characterize binding in a 'micropanning' approach on lysozyme immobilised on a 96-well ELISA plate. Bound phage were eluted and counted. Out of 22 clones 9 showed phage recovery numbers above the background of pIII, OB wild-type and BSA (clones L4, L5, L6, L8, L14, L15, L16, L18, L21, FIG. 13). These clones were sequenced. Sequences for some of the clones were identical (L14 and L15; L4 and L18; L8 and L21) narrowing down the number of unique clones to six. This redundancy indicated a high proportion of clones with the same sequence in the sample due to enrichment. Two more rounds of panning were performed and 6 more clones were sequenced (L32, L33, L34, L42, L43, L44). Three sequences matched sequences of previous clones (L32=L14=L15, L33=L8=L21=L43), while L44 was identical to L5 in the beta-sheet region but showed a different pattern in the loop region. L34 and L42 were new sequences. The number of clones in the selected pool after 6 rounds can be assumed to be very small and covered to a significant extent by the nine sequences shown in FIG. 12, panel E. Clones L14 (L32, L15), L8 (L33, L21, L43), L34, L4, L5 and L6 were subjected to binding studies in an ELISA approach using multivalent display (FIG. 14). Results showed that all clones bound to lysozyme whereas particles without a displayed aspRS-OB did not (pIII). Other negative controls included the wild type aspRS-OB (OBwt). All analyzed clones bind in higher numbers (higher OD values in ELISA experiments) to lysozyme than to RNaseA or BSA demonstrating specificity of binding to lysozyme. As shown in FIG. 11, clones L6 and L33 did not bind to tRNA.

Example 10

Expression and Analysis of Purified Mutants

Figures 15A, 15B:
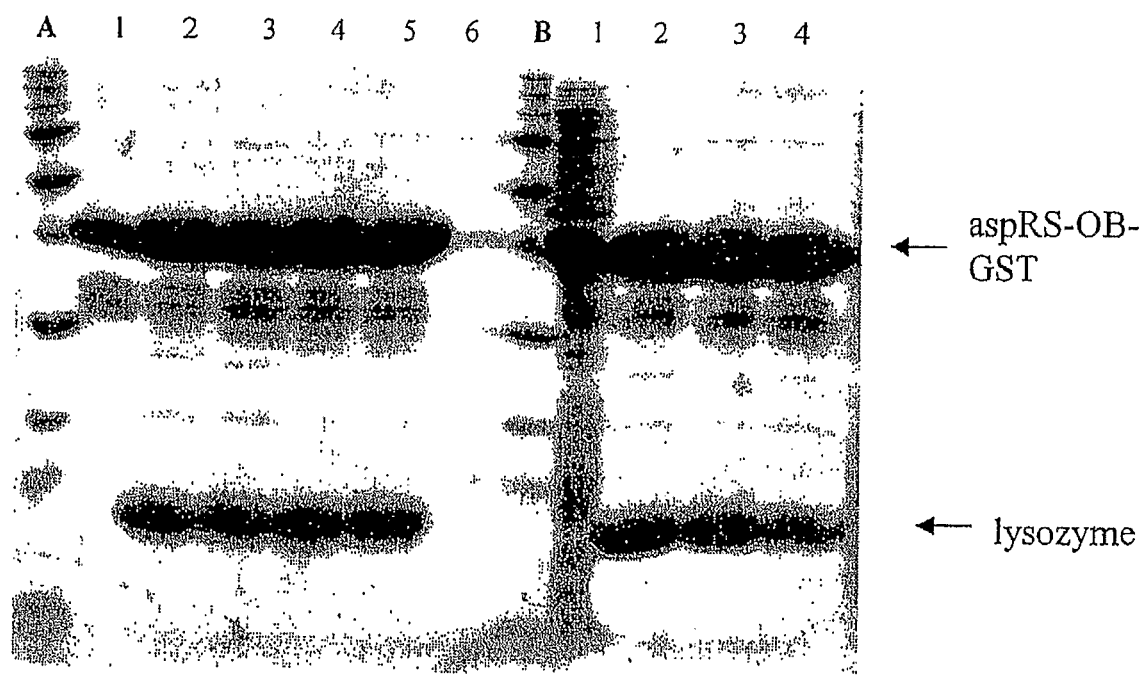
FIGS. 15A-15B show pull down assay with purified aspRS-OB mutants selected on lysozyme.

Clones L4 (L18), L5, L6, L16 and L33 (L21) were subcloned into an expression vector and expressed as GST fusion proteins for analysis for lysozyme binding in 'pull-down' assays. As shown in FIGS. 15A-15B, immobilised mutants bound lysozyme whereas the unselected mutant 13mRL81 did not bind. This confirmed binding of selected mutants to lysozyme. L6 binding to lysozyme was studied in presence of different buffers. FIG. 15B shows that L6 binds to lysozyme after washing with 500 mM NaCl. Clone L6 was expressed and purified and its binding kinetics on immobilised lysozyme were analyzed using surface plasmon resonance (Biacore). The binding constant was calculated to be $3.6 \times 10^{-5}$ M (FIG. 16).

These experiments demonstrate the production of large, synthetic libraries of OB-fold domains which contain randomized codons and demonstrate that transcribed, mutant proteins from these libraries are stable and folded. Functional display of an OB-fold domain is demonstrated at the surface of phage thus allowing efficient screening of the library for differing functions of choice. Selection of modified OB-fold domains, from OB-fold libraries, using phage display is demonstrated. These variants must have desired characteristics, be they chosen binding interactions or enzymatic activity. As demonstrated herein, the tRNA anticodon binding domain of Aspartate tRNA Synthetase (AspRS) from *Pyrobaculum aerophilum* was chosen as an OB-fold scaffold to demonstrate the applicability of OB-folds to serve as carriers of diversity. The results show that this tRNA anticodon binding domain can be converted into a specific protein binding molecule by applying the methods disclosed herein.

Each mutation introduced into a protein framework can potentially affect its folding and thus its stability and solubility. To understand the tolerance towards mutations in the protein framework libraries containing different sets, or combinations of mutated areas, were generated and screened for expression and solubility of randomly picked mutants. Libraries with unrestricted diversity were planned and generated. Such naive libraries contain all possible combinations of mutations through randomisation. It is expected that a large number of mutants will not be tolerated for reasons of either stability, folding or solubility due to unfavorable combinations of amino acids in particular areas in the molecule. A library derived from aspRS-OB containing 17 random amino acid positions in the binding face, 13 on the beta sheet (beta strands 1-3) and 4 in the loop between strands 4 and 5 was generated. Libraries comprising sets of mutations addressing individual beta strands or the loop region only were generated.

After screening libraries of modified OB-fold domains for expression and solubility it was found that ~16% of all mutants in a 17-mutation library of aspRS-OB were overexpressing and soluble and a few selected mutants were proven to fold accurately as demonstrated by NMR and CD spectroscopy. This shows that a significant proportion of this library is usable for selection against a target of interest. AspRS-OB Libraries 13mRL and RL were constructed as phage display libraries. The practical diversity of 13mRL was $\sim 8 \times 10^7$ different clones representing a very small fraction of the $\sim 5 \times 10^{22}$ possible combinations (theoretical diversity) of 17 random positions. The diversity of RL is only $1.6 \times 10^5$ (4 random positions) and is expected to be fully covered by $\sim 1 \times 10^7$ clones after transformation. Sequencing of randomly picked clones confirmed the diversity of the library.

Phage display is the most commonly used display technology and thus favorable for display of the aspRS-OB scaffold. There are no reports of the display of an aspRS anticodon binding domain at the surface of a phage, or the display of any other OB-fold domain in general. Display of a protein on a phage requires several steps that might affect the integrity of the displayed protein as well as the growth of the host cell. After synthesis in the cytoplasm the protein has to be stable in the reducing environment of the cell and must be unaffected by fusion to the pIII phage protein. The fusion protein is then targeted through the oxidising environment of the periplasm for phage assembly before the whole phage particle is released into the media. For any protein this process involves interactions with the environment at multiple stages, and in case of a scaffold derived from an anticodon binding domain binding to host nucleic acids must also be considered. Detection of aspRS-OB (by Western analysis) displayed on M13 phage showed good expression. Detection of aspRS-OB libraries RL and the larger 13mRL (also by Western blotting) showed much less efficient display on phage. This observation can be explained by a high degree of unstable mutants in the naive random libraries. These data suggest proteolytic degradation of unfavorable mutants in the cytoplasm or periplasm of E. coli, an effect observed before in studies on the Z-domain from protein A (50). This also correlates with results from the expression and solubility screens. Weaker signals of phage displaying libraries were observed in other scaffolds (carbohydrate binding domain, (51); cellulose binding domain, (52)). Library designs of future libraries would need to take this factor into account to increase the ratio of displayed fusion to degradation. This is a general problem of naive random libraries and not a phenomenon observed in OB-folds only.

Selection on asp-tRNA

Phage binding and selection experiments on the native target asp-tRNA indicated successful and functional display of asp-OB and its derived libraries on M13 phage. From the small RL library a consensus sequence was obtained representing mutants with higher affinity than the wild type as shown in monoclonal panning experiments. The derived consensus sequence R/K G C R was different from the wild-type sequence and contained 2 positively charged amino acids suggesting binding to the negatively charged RNA backbone. The presence of the glycine in this loop region might ensure flexibility of the loop while the function of the cysteine remains unclear.

Sequences of unselected clones showed diversity of the aspRS-OB RL library and sequences from clones matching the consensus sequences after selection showed variation of the corresponding DNA codons demonstrating selection for the phenotype rather than for genotype. Due to a very limited coverage of the diverse library 13mRL, a consensus could not be derived from the small number of sequences of clones selected on asp-tRNA. This is expected since the practical diversity is about $10^8$ clones but the theoretical diversity is approximately $10^{22}$. Thus, the diversity coverage of the phage library is only a very small fraction of that theoretically possible. A significant number of positively charged residues was observed in all sequenced clones (9 in D07, 5 in D05, 6 in D09) indicating a selection for positively charged residues through binding to the negatively charged RNA backbone. The motif R X G S occurring in two mutants (D07, D04) suggests an important role of the loop in tRNA binding as it is the case for the wild-type aspRS-OB. Binding experiments with monoclonal phage samples showed stronger binding to asp-tRNA than the wild-type domain. This supported the conclusion that a selection upon binding to the immobilised target occurred and indicated that our OB-fold scaffold is well suited for display on phage and the biopanning process.

Selection on Lysozyme

The 13mRL library was selected on hen egg lysozyme. After several rounds of panning a number of clones were isolated and analyzed for sequence and for binding to the target molecule. Out of 22 clones in a pre-screen, 6 finally showed detectable binding to lysozyme in a phage ELISA experiment. Examination of sequences of 14 clones revealed that two were detected twice, one even four times. This suggests a reasonably small number of different clones in the selected fraction. Sequences of 9 different clones indicated similarities in their composition. A few positions showed some interesting similarities, for example position 29, which is an acidic residue (D or E) in 6 clones out of 9, position 31 is a valine in 5 out of 9 sequences, in position 35 a positively charged residue appears in 4 clones, position 38 is an aromatic residue (Y, F, W) in 5 cases and finally position 85 is glycine in 5 clones. Also, in beta strand 3, there are noticeable patterns ETET (SEQ ID NO:80) and PETE (SEQ ID NO:81) occurring in clones L16 and L34, and in beta strand 1 D V/L A/L in L32, L2, L6, L5, L44. Also striking is the identity of L5 and L44 in the beta sheet whereas the loop region is different. There are no cysteines in all mutants except L6. However, more obvious consensus sequences could not be derived probably due to poor coverage of the very large library and the small number of sequences obtained. Several clones were expressed and purified as GST fusion proteins and analyzed by pull down experiments showing binding of the clones to lysozyme. Clone L6 bound even in the presence of 500 mM sodium chloride indicating binding of reasonable affinity. Clone L6 was expressed and purified and the kinetics and thermodynamics of binding were analyzed by surface plasmon resonance showing a $K_d$ of $\sim 3.6 \times 10^{-5}$ M. Considering the small size and the composition of this naive library a binding constant in μM range is a very significant result and offers an excellent starting point for optimization by affinity maturation procedures.

Example 11

Three Dimensional Structure of the OBody L8 in Complex with Lysozyme

L8 was cloned using Gateway (Invitrogen) into pDONR221 then subcloned into the expression vector pDEST15 which was transformed into BL21 (DE3) E. coli cells. These cells were inoculated into 500 mL of auto-induction media and shaken at 37° C. in 2 L baffled flasks. The fusion protein GST-L8 was purified from bacterial lysate using a GSH affinity column (GE Biosciences). The GST tag was removed using rTEV protease and separated from L8 by size exclusion chromatography (S75 16/60 prep-grade, GE Biosciences). L8 was then purified a third time to improve monodispersion in solution, again by size exclusion (S75 10/300 analytical grade, GE Biosciences).

The purified protein was combined with Gallus gallus egg white lysozyme (Roche) in an approximate 1:1 molar ratio, to a final concentration of L8 at 37.5 mg/mL and lysozyme at 42.9 mg/mL, in TBS (25 mM TRIS, pH 7.5, 137 mM NaCl, 3 mM KCl). The complex in solution was screened against 480 crystallisation conditions using custom screens and a sitting drop format.

A single large crystal grew from an equal mixture of protein in TBS and precipitant (7% MPEG 5K, 0.2 M HEPES pH 7.8). This crystal was then gathered in a nylon loop, coated in cyroprotectant, and frozen under a stream of cold $N_2$ gas (110 K). A dataset of 700 images was collected using a rotating anode X-ray generator and Mar345 detectors giving diffraction to 2.8 Å. Images were indexed using DENZO and data were scaled using Scalepack. For data collection statistics see table. The structure was solved using molecular replacement (AMoRe) incorporating both lysozyme (PDB entry 193L) and the OB-fold codon recognition domain from the *Pyrococcus kodakarensis* aspartyl tRNA synthase (PDB entry 1B8A) as models. Two molecules of lysozyme were found in the asymmetric unit along with one OB-fold domain. A second OB-fold was placed by replicating the complex in the asymmetric unit based on the position of the second lysozyme molecule. The structure was iteratively built and refined using COOT, CCP4 and PHENIX. A second dataset was collected using the same crystal at the SSRL, to 2.69 Å resolution. It was indexed in the same space group and phased by molecular replacement using the complete unit cell from the previous structure. Building and refinement was done using COOT, CCP4 and PHENIX.

TABLE 7

Statistics for X-ray crystallographic structure of L8 in complex with lysozyme.

| | Home Source Data | Synchrotron Data |
|---|---|---|
| Crystal Properties | | |
| Space Group | $P4_12_12$ | $P4_12_12$ |
| Unit Cells Axes (a, b, c) | 76.585, 76.585, 166.150 | 76.759, 76.759, 166.344 |
| Unit Cell Angles (α, β, γ) | 90, 90, 90 | 90, 90, 90 |
| Data Collection | | |
| Resolution | 50-2.8 (2.872-2.8) | 34.85-2.69 (2.76-2.69) |
| Total Reflections | 267,952 | 144,772 |
| Unique Reflections | 12,301 | 16,010 |
| Completeness | 95.3 (54.75) | 99.15 (92.80) |
| Redundancy | 21 | 9 |
| $R_{merge}$ | 4.2 (59.0) | 7.3 (54.3) |
| Wilson B Factor | 85 | 65 |
| Mosaicity | 0.6 | 0.6 |
| I/σI | 50.14 (1.6) | 32.50 (4.22) |
| Molecular Replacement | | |
| Correlation Coefficient | 66.2 | 71.2 |
| R | 52.7 | 38.9 |
| Refinement | | |
| Resolution | 25-2.8 (2.872-2.8) | 27.5-2.75 (2.82-2.75) |
| R | 26.5 (35.0) | 22.5 (26.5) |
| $R_{free}$ | 34.0 (50.7) | 29.6 (37.6) |
| Protein Atoms | 3338 | 3384 |
| rmsd, bond lengths | 0.012 | 0.013 |
| rmsd, bond angles | 1.541 | 1.452 |
| B factors, average | 66.942 | 51.146 |

TABLE 8

Protein-protein interface data for L8 in complex with lysozyme

| | |
|---|---|
| Buried surface area | 840 Å$^2$ |
| Average antibody/antigen buried surface area | 950 Å$^2$ |
| H-bonds at interface | 7 |
| Salt bridges at interface | 2 |
| Polar:Non-polar atoms at interface | 43%:57% |
| Gap Volume Index | 2.94 |
| Average Gap Volume Index (antibody/antigen) | 3.0 |
| $K_d$ (surface plasmon resonance) | 36 μM |

APPENDIX I

```
OB fold    Oligo   5'-3' sequence aspRS      005     CAC C AGT GGA TCC GTG TAT CCT AAA AAG ACC   (SEQ ID NO: 30)
           006     ACC CGG GAA TTC TCA GTC TAT TGG AAG CGG CTT  (SEQ ID NO: 31)

IF-5A      011     CAC C AGT GGA TCC ATT GAG AAA TTC ACG GCG    (SEQ ID NO: 32)
           012     ACC CGG GAA TTC TCA CTA TTT AAC TCT AAT AAT  (SEQ ID NO: 33)
```

Oligonticleotides for PCR amplification of the wild type OB-folds of aspRS and IF-5A from *Pyrobaculum aerophilum*.

```
Oligo   5'-3' sequence

050     GGT GAC CTA CCA TGG CCC AGG TGG TGT ATC CTA AAA AGA CCC AC  (SEQ ID NO: 34)

054     TAC CCA ACC GGC AAC AAC                                      (SEQ ID NO: 35)

055     GTT GTT GCC GGT TGG GTA                                      (SEQ ID NO: 36)

056     CGC GCC CCC CTC CCT ATC                                      (SEQ ID NO: 37)

057     GAT AGG GAG GGG GCG                                          (SEQ ID NO: 38)

058     ATC GGG GGT TTT TCC CGC                                      (SEQ ID NO: 39)

059     GCG GGA AAA ACC CCC GAT                                      (SEQ ID NO: 40)

060     TTT ACT GGC CTC AAC AAT                                      (SEQ ID NO: 41)
```

APPENDIX I-continued

```
061   ATT GTT GAG GCC AGT AAA  (SEQ ID NO: 42)

062   GGT GTG GAG ATT TTC CCC  (SEQ ID NO: 43)

068   GAG GGG GGC GCG TTT GTG CAA GTC ACG CTC AAG G  (SEQ ID NO: 44)
```

Oligonucleotides for PCR assembly of libraries based on aspRS-OB
from *P. aerophilum*

```
028   GGAGATAGCAACGGCGCGGTAATTCAGCTAATGGAC  (SEQ ID NO: 45)

029   CGCGCCGTTGCTATCTCCTGAAACGGAGAGTATTTG  (SEQ ID NO: 46)

032   GTGCCGATGAAATACGTC  (SEQ ID NO: 47)

033   GACGTATTTCATCGGCAC  (SEQ ID NO: 48)

034   CGCGCCGTTGCTATCTCC  (SEQ ID NO: 49)

035   GGAGATAGCAACGGCGCGV  (SEQ ID NO: 50)

074   ATCTCCTGAAACGGAGAG  (SEQ ID NO: 51)

076   TAGCTGAATTACCGCGCC  (SEQ ID NO: 52)

078   CTCTCCGTTTCAGGAGA  (SEQ ID NO: 53)

089   GGCGCGGTAATTCAGCTA  (SEQ ID NO: 54)
```

Oligonucleotides for PCR assembly of libraries based on IF5A-OB
from *P. aerophilum*

APPENDIX II

Amino Acid Sequences of Various Obodies. The numbering for the sequences is consistent with the numbering in FIG. 10 and FIG. 12.

| Designation | Amino Acid Sequence |
|---|---|
| U1 | VYPKKTHWTAEITPNLHGTEVVVAGWVECLADTGIEKGVLVVDREGGACVRVHLQAGKTPDH<br>LFKVFAELSREDVVVIKGIVEASKGYKSGVEIFPSEIWILNKAKPLPID  (SEQ ID NO: 1) |
| U2 | VYPKKTHWTAEITPNLHGTEVVVAGWVGALRDLGLGKGVSVFDREGGAVVTVNLLAGKTPDH<br>LFKVFAELSREDVVVIKGIVEASKSRVGGVEIFPSEIWILNKAKPLPID  (SEQ ID NO: 2) |
| U3 | VYPKKTHWTAEITPNLHGTEVVVAGWVAALGDAGDSKTVTVNDREGGAPVHVQLDAGKTPDH<br>LFKVFAELSREDVVVIKGIVEASKYRLKGVEIFPSEIWILNKAKPLPID  (SEQ ID NO: 3) |
| U4 | VYPKKTHWTAEITPNLHGTEVVVAGWVDPLLDRGLAKGVSVRDREGGASVPVTLLAGKTPDH<br>LFKVFAELSREDVVVIKGIVEASKQRYVGVEIFPSEIWILNKAKPLPID  (SEQ ID NO: 4) |
| U5 | VYPKKTHWTAEITPNLHGTEVVVAGWVKVLPDGGFCKYVRVEDREGGASVLVALSAGKTPDH<br>LFKVFAELSREDVVVIKGIVEASKLGHFGVEIFPSEIWILNKAKPLPID  (SEQ ID NO: 5) |
| U6 | VYPKKTHWTAEITPNLHGTEVVVAGWVISLSDRGGTKLVEVIDREGGAAVIVQLLAGKTPDH<br>LFKVFAELSREDVVVIKGIVEASKRLVNGVEIFPSEIWILNKAKPLPID  (SEQ ID NO: 6) |
| U7 | VYPKKTHWTAEITPNLHGTEVVVAGWVFXLLDXGMGKLVRVPDREGGAPVDVDLPAGKTPDH<br>LFKVFAELSREDVVVIKGIVEASKCGGGGEIFPHEIWILNKGKPLPID  (SEQ ID NO: 7) |
| U8 | VYPKKTHWTAEITPNLHGTEVVVAGWVWELRDIGKVKFVVVRDREGFVQVTLKAGKTPDHLF<br>KVFAELSREDVVVIKGIVEASKVGALGVEIFPSEIWILNKAKPLPID  (SEQ ID NO: 8) |
| U9 | VYPKKTHWTAEITPNLHGTEVVVAGWVWELRDIGKVKFVVVRDREGFVQVTLKAGKTPDHLF<br>KVFAELSREDVVVIKGIVEASKGCDCGVEIFPSEIWILNKAKPLPID  (SEQ ID NO: 9) |
| S68 | VYPRKTHWTAEITPNLHGTEVVVAGWVRSLVDGGRVKAVNVQDREGGAKVEVLLEAGKTPDH<br>LFKVFAELSREDVVVIKGIVEASKGEWSGVEIFPSEIWILNKAKPLPID  (SEQ ID NO: 10) |
| S81 | VYPKKTHWTAEITPNLHGTEVVVAGWVKGLVDMGLLKGVTVGDREGGASVLVRLTAGKTPDH<br>LFKVFAELSREDVVVIKGTVEASKLVPQGVEIFPSEIWILNKAKPLPID  (SEQ ID NO: 11) |
| pMB16 | VYPKKTHWTAEITPNLHGTEVVVAGWVWELRDIGKVKFVVVRDREGFVQVTLKAGKTPDHLF<br>KVFAELSREDVVVIKGIVEASKRGCRGVEIFPSEIWILNKAKPLPID  (SEQ ID NO: 12) |

APPENDIX II-continued

Amino Acid Sequences of Various Obodies. The numbering for the sequences is consistent with the numbering in FIG. 10 and FIG. 12.

| Designation | Amino Acid Sequence |
|---|---|
| pMB17 | VYPKKTHWTAEITPNLHGTEVVVAGWVWELRDIGKVKFVVVRDREGFVQVTLKAGKTPDHLF KVFAELSREDVVVIKGIVEASKKGCRGVEIFPSEIWILNKAKPLPID (SEQ ID NO: 13) |
| pMB12 | VYPKKTHWTAEITPNLHGTEVVVAGWVWELRDIGKVKFVVVRDREGFVQVTLKAGKTPDHLF KVFAELSREDVVVIKGIVEASKRGCAGVEIFPSEIWILNKAKPLPID (SEQ ID NO: 14) |
| pMB18 | VYPKKTHWTAEITPNLHGTEVVVAGWVWELRDIGKVKFVVVRDREGFVQVTLKAGKTPDHLF KVFAELSREDVVVIKGIVEASKRSCRGVEIFPSEIWILNKAKPLPID (SEQ ID NO: 15) |
| pMB15 | VYPKKTHWTAEITPNLHGTEVVVAGWVWELRDIGKVKFVVVRDREGFVQVTLKAGKTPDHLF KVFAELSREDVVVIKGIVEASKLSLVGVEIFPSEIWILNKAKPLPID (SEQ ID NO: 16) |
| D05 | VYPKKTHWTAEITPNLHGTEVVVAGWVQRLYDRGKRKSVSVVDREGGAPVTVCLRAGKTPDH LFKVFAELSREDVVVIKGIVEASKWNCGXVEIFPSEIWILNKAKPLPID (SEQ ID NO: 17) |
| D07 | VYPKKTHWTASITPNLHGTEVVVAGWVRKLRDRGPAKYVWVRDREGGATVRVRLQAGKTPDH LFKVFAELSREDVVVIKGIVEASKRKGSGVEIFPSEIWILNKAKPLPID (SEQ ID NO: 18) |
| D09 | VYPKKTHWTAEITPNLHGTEVVVAGWVWRLRDWGLAKTVRVKDREGGASVRVTLRAGKTPDH LFKVFAELSREDVVVIKGIVEASKWWVWGVEIFPSEIWILNKAKPLPID (SEQ ID NO: 19) |
| D04 | VYPKKTHWTAEITPNLHGTEVVVAGWVSCLCDAGKRKWVYVVDREGGAPVAVRLRAGKTPDH LFKVFAELSREDVVVIKGIVEASKRAGSGVEIFPSEIWILNKAKPLPID (SEQ ID NO: 20) |
| L14 | VYPKKTHWTAEITPNLHGTEVVVAGWVSDLLDAGRAKYVFVYDREGGAEVMVTLAAGKTPDH LFKVFAELSREDVVVIKGIVEASKGWRDGVEIFPSEIWILNKAKPLPID (SEQ ID NO: 21) |
| L8 | VYPKKTHWTAEITPNLHGTEVVVAGWVASLGDYGRVKIVKVSDREGGAAVPVYLEAGKTPDH LFKVFAELSREDVVVIKGIVEASKGVGRGVEIFPSEIWILNKAKPLPID (SEQ ID NO: 22) |
| L4 | VYPKKTHWTAEITPNLHGTEVVVAGWVGELADFGDMKTVAVRDREGGAEVPVTLLAGKTPDH LFKVFAELSREDVVVIKGIVEASKGSTSGVEIFPSSIWILNKAKPLPID (SEQ ID NO: 23) |
| L16 | VYPKKTHWTAEITPNLHGTEVVVAGWVASLVDGGPRKWVFVRDREGGAEVTVELTAGKTPDH LFKVFAELSREDVVVIKGIVEASKGLRWGVEIFPSEIWILNKAKPLPID (SEQ ID NO: 24) |
| L34 | VYPKKTHWTAEITPNLHGTEVVVAGWVVGLMDEGALKGVEVRDREGGAPVEVTLEAGKTPDH LFKVFAELSREDVVVIKGIVEASKGYGSGVEIFPSEIWILNKAKPLPID (SEQ ID NO: 25) |
| L42 | VYPKKTHWTAEITPNLHGTEVVVAGWVVDLVDLGRNKLVQVSDREGGARVLVNLAAGKTPDH LFKVFAELSREDVVVIKGIVEASKIQRSGVEIFPSEIWILNKAKPLPID (SEQ ID NO: 26) |
| L6 | VYPKKTHWTAEITPNLHGTEVVVAGWVEDLVDAGKTKWVFVCDREGGAQVIVELVAGKTPDH LFKVFAELSREDVVVIKGIVEASKSRAVGVEIFPSEIWILNKAKPLPID (SEQ ID NO: 27) |
| L5 | VYPKKTHWTAEITPNLHGTEVVVAGWVTDLVDAGTWKFVQVADREGGANVWVSLVAGKTPDH LFKVFAELSREDVVVIKGIVEASKLPSYGVEIFPSEIWILNKAKPLPID (SEQ ID NO: 28) |
| L44 | VYPKKTHWTAEITPNLHGTEVVVAGWVTDLVDAGTWKFVQVADREGGANVWVSLVAGKTPDH LFKVFAELSREDVVVIKGTVEASKPGAAGVEIFPSEIWILNKAKPLPID (SEQ ID NO: 29) |

REFERENCES

1. Rajewsky, K. 1996. Clonal selection and learning in the antibody system. *Nature* 381: 751-758.
2. Griffiths, A. D., S. C. Williams, O. Hartley, I. M. Tomlinson, P. Waterhouse, W. L. Crosby, R. E. Kontermann, P. T. Jones, N. M. Low, T. J. Allison, and et al. 1994. Isolation of high affinity human antibodies directly from large synthetic repertoires. *EMBO Journal* 13: 3245-3260.
3. Nissim, A., H. R. Hoogenboom, I. M. Tomlinson, G. Flynn, C. Midgley, D. Lane, and G. Winter. 1994. Antibody fragments from a 'single pot' phage display library as immunochemical reagents. *EMBO Journal* 13: 692-698.
4. Atwell, S., M. Ultsch, A. M. De Vos, and J. A. Wells. 1997. Structural plasticity in a remodeled protein-protein interface. *Science* 278: 1125-1128.
5. Ballinger, M. D., J. T. Jones, J. A. Lofgren, W. J. Fairbrother, R. W. Akita, M. X. Sliwkowski, and J. A. Wells. 1998. Selection of heregulin variants having higher affinity for the erbb3 receptor by monovalent phage display. *Journal of Biological Chemistry* 273: 11675-11684.
6. Gunneriusson, E., K. Nord, M. Uhlen, and P. A. Nygren. 1999. Affinity maturation of a taq DNA polymerase specific affibody by helix shuffling. *Protein Engineering* 12: 873-878.
7. Nord, K., J. Nilsson, B. Nilsson, M. Uhlen, and P. A. Nygren. 1995. A combinatorial library of an alpha-helical bacterial receptor domain. *Protein Engineering* 8: 601-608.
8. Binz, H. K., P. Amstutz, and A. Pluckthun. 2005. Engineering novel binding proteins from nonimmunoglobulin domains. *Nature Biotechnology* 23: 1257-1268.
9. Binz, H. K., and A. Pluckthun. 2005. Engineered proteins as specific binding reagents. *Current Opinion in Biotechnology* 16: 459-469.

10. Hosse, R. J., A. Rothe, and B. E. Power. 2006. A new generation of protein display scaffolds for molecular recognition. *Protein Science* 15: 14-27.
11. Sidhu, S. S., H. B. Lowman, B. C. Cunningham, and J. A. Wells. 2000. Phage display for selection of novel binding peptides. *Methods in Enzymology* 328: 333-363.
12. Stemmer, W. P. C. 1994. DNA shuffling by random fragmentation and reassembly: In vitro recombination for molecular evolution. *Proceedings of the National Academy of Sciences of the United States of America* 91: 10747-10751.
13. Sidhu, S. S. 2000. Phage display for selection of novel binding peptides. *Methods in Enzymology* 328: 333-363.
14. Stemmer, W. P. C. 1994. Rapid evolution of a protein in vitro by DNA shuffling. *Nature* 370: 389-391.
15. Zhao, H., and F. H. Arnold. 1997. Optimisation of DNA shuffling for high fidelity recombination. *Nucleic Acids Research* 25: 1307-1308.
16. Zhao, H., L. Giver, Z. Shao, J. A. Affholter, and F. H. Arnold. 1998. Molecular evolution by staggered extension process (step) in vitro recombination. [see comment]. *Nature Biotechnology* 16: 258-261.
17. Volkov, A. A., and F. H. Arnold. 2000. Methods for in vitro DNA recombination and random chimeragenesis. *Methods in Enzymology* 328: 447-456.
18. Coco, W. M., W. E. Levinson, M. J. Crist, H. J. Hektor, A. Darzins, P. T. Pienkos, C. H. Squires, and D. J. Monticello. 2001. DNA shuffling method for generating highly recombined genes and evolved enzymes. [see comment]. *Nature Biotechnology* 19: 354-359.
19. Hemminki, A., S. Niemi, A. M. Hoffren, L. Hakalahti, H. Soderlund, and K. Takkinen. 1998. Specificity improvement of a recombinant anti-testosterone Fab fragment by CDRIII mutagenesis and phage display selection. *Protein Engineering* 11: 311-319.
20. Jermutus, L., A. Honegger, F. Schwesinger, J. Hanes, and A. Pluckthun. 2001. Tailoring in vitro evolution for protein affinity or stability. *Proceedings of the National Academy of Sciences of the United States of America* 98: 75-80.
21. Hanes, J., L. Jermutus, and A. Pluckthun. 2000. Selecting and evolving functional proteins in vitro by ribosome display. *Methods in Enzymology* 328: 404-430.
22. Boder, E. T., and K. D. Wittrup. 2000. Yeast surface display for directed evolution of protein expression, affinity and stability. *Methods in Enzymology* 328: 430-445.
23. Altamirano, M. M., J. M. Blackburn, C. Aguayo, and A. R. Fersht. 2000. Directed evolution of a new catalytic activity using the a/b-barrel scaffold. *Nature* 403: 617-622.
24. Arcus, V. 2002. Ob-fold domains: A snapshot of the evolution of sequence, structure and function. *Current Opinion in Structural Biology* 12: 794-801.
25. Arcus, V. L., T. Proft, J. A. Sigrell, H. M. Baker, J. D. Fraser, and E. N. Baker. 2000. Conservation and variation in superantigen structure and activity highlighted by the three-dimensional structures of two new superantigens from *streptococcus pyogenes*. *Journal of Molecular Biology* 299: 157-168.
26. Murzin, A. G. 1993. Ob (oligonucleotide/oligosaccharide binding)-fold: Common structural and functional solution for non-homologous sequences. *EMBO Journal* 12: 861-867.
27. Qian, J., B. Stenger, C. A. Wilson, J. Lin, R. Jansen, S. A. Teichmann, J. Park, W. G. Krebs, H. Yu, V. Alexandrov, N. Echols, and M. Gerstein. 2001. Partslist: A web-based system for dynamically ranking protein folds based on disparate attributes, including whole-genome expression and interaction information. *Nucleic Acids Research* 29: 1750-1764.
28. Zhang, C., and S. H. Kim. 2000. A comprehensive analysis of the greek key motifs in protein beta-barrels and beta-sandwiches. *Proteins* 40: 409-419.
29. Murzin, A. G., A. M. Lesk, and C. Chothia. 1994. Principles determining the structure of beta-sheet barrels in proteins. I. A theoretical analysis. *Journal of Molecular Biology* 236: 1369-1381.
30. Murzin, A. G., A. M. Lesk, and C. Chothia. 1994. Principles determining the structure of beta-sheet barrels in proteins. Ii. The observed structures. *Journal of Molecular Biology* 236: 1382-1400.
31. Beekwilder, J., J. Rakonjac, M. Jongsma, and D. Bosch. 1999. A phagemid vector using the e. Coli phage shock promoter facilitates phage display of toxic proteins. *Gene* 228: 23-31.
32. Rakonjac, J., G. Jovanovic, and P. Model. 1997. Filamentous phage infection-mediated gene expression: Construction and propagation of the gIII deletion mutant helper phage R408d3. *Gene* 198: 99-103.
33. Berman, H. M., J. Westbrook, Z. Feng, G. Gilliland, T. N. Bhat, H. Weissig, I. N. Shindyalov, and P. E. Bourne. 2000. The protein data bank. *Nucleic Acids Research* 28: 235-242.
34. Peat, T. S., J. Newman, G. S. Waldo, J. Berendzen, and T. C. Terwilliger. 1998. Structure of translation initiation factor 5A from *pyrobaculum aerophilum* at 1.75 A resolution. *Structure* 6: 1207-1214.
35. Schmitt, E., L. Moulinier, S. Fujiwara, T. Imanaka, J. C. Thierry, and D. Moras. 1998. Crystal structure of aspartyl-tRNA synthetase from *pyrococcus kodakaraensis* kod: Archaeon specificity and catalytic mechanism of adenylate formation. *EMBO Journal* 17: 5227-5237.
36. Moulinier, L., S. Eiler, G. Eriani, J. Gangloff, J. C. Thierry, K. Gabriel, W. H. McClain, and D. Moras. 2001. The structure of an AspRS-tRNA (Asp) complex reveals a tRNA-dependent control mechanism. *EMBO Journal* 20: 5290-5301.
37. Rees, B., G. Webster, M. Delarue, M. Boeglin, and D. Moras. 2000. Aspartyl tRNA-synthetase from *Escherichia coli*: Flexibility and adaptability to the substrates. *Journal of Molecular Biology* 299: 1157-1164.
38. Guex, N., and M. C. Peitsch. 1997. SWISS-MODEL and the Swiss-PdbViewer: An environment for comparative protein modeling. *Electrophoresis* 18: 2714-2723.
39. Peitsch, M. 1995. Protein modeling by e-mail. *Bio/Technology:* 658-660.
40. Schwede, T., J. Kopp, N. Guex, and M. C. Peitsch. 2003. SWISS-MODEL: An automated protein homology-modeling server. *Nucleic Acids Research* 31: 3381-3385.
41. Sambrook, J., and D. W. Russel. (2001) *Molecular cloning a laboratory manual,* 3rd Ed., Cold Spring Harbor Laboratory Press, New York
42. Fitz-Gibbon, S. T., H. Ladner, U. J. Kim, K. O. Stetter, M. I. Simon, and J. H. Miller. 2002. Genome sequence of the hyperthermophilic crenarchaeon *pyrobaculum aerophilum*. *Proceedings of the National Academy of Sciences of the United States of America* 99: 984-989.
43. Bullock, W. O., J. M. Fernandez, and J. M. Short. 1987. X11-blue—a high-efficiency plasmid transforming recA *Escherichia-coli* strain with beta-galactosidase selection. *Biotechniques* 5: 376-&.
44. Rakonjac, J., J. Feng, and P. Model. 1999. Filamentous phage are released from the bacterial membrane by a two-step mechanism involving a short C-terminal fragment of pIII. *Journal of Molecular Biology* 289: 1253-1265.
45. Barbas III, C., D. Burton, J. Scott, and G. Silverman. (2001) *Phage display a laboratory manual*, Cold Spring Harbor Laboratory Press, New York
46. Gough, J., K. Karplus, R. Hughey, and C. Chothia. 2001. Assignment of homology to genome sequences using a library of hidden Markov models that represent all proteins of known structure. *Journal of Molecular Biology* 313: 903-919.
47. Bogden, C. E., D. Fass, N. Bergman, M. D. Nichols, and J. M. Berger. 1999. The structural basis for terminator recognition by the Rho transcription termination factor. *Molecular Cell* 3: 487-493.
48. Hoogenboom, H. R., A. P. de Bruine, S. E. Hufton, R. M. Hoet, J. W. Arends, and R. C. Roovers. 1998. Antibody phage display technology and its applications. *Immunotechnology* 4: 1-20.
49. Brevet, A., J. Chen, S. Commans, C. Lazennec, S. Blanquet, and P. Plateau. 2003. Anticodon recognition in evolution—switching tRNA specificity of an aminoacyl-tRNA synthetase by site-directed peptide transplantation. *Journal of Biological Chemistry* 278: 30927-30935.
50. Wahlberg, E., C. Lendel, M. Helgstrand, P. Allard, V. Dincbas-Renqvist, A. Hedqvist, H. Berglund, P. A. Nygren, and T. Hard. 2003. An affibody in complex with a target protein: Structure and coupled folding. *Proceedings of the National Academy of Sciences of the United States of America* 100: 3185-3190.
51. Gunnarsson, L. C., E. N. Karlsson, A. S. Albrekt, M. Andersson, O. Holst, and M. Ohlin. 2004. A carbohydrate binding module as a diversity-carrying scaffold. *Protein Engineering Design & Selection* 17: 213-221.
52. Berdichevsky, Y., E. Ben-Zeev, R. Lamed, and I. Benhar. 1999. Phage display of a cellulose binding domain from *Clostridium thermocellum* and its application as a tool for antibody engineering. *Journal of Immunological Methods* 228: 151-162.

What is claimed is:

1. An isolated modified OB-fold domain, obtainable from a naturally occurring OB-fold domain and removed from the naturally occurring protein within which it is contained, wherein:
   (a) at least one amino acid residue located in a β-strand of the OB-fold domain binding face is mutated by substitution as compared to the naturally occurring OB-fold domain amino acid residue, or
   (b) at least one amino acid residue located in a β-strand of the OB-fold domain binding face and at least one amino acid residue located in a strand of the OB-fold domain loop region are mutated by substitution as compared to the naturally occurring OB-fold domain amino acid residues,
   (c) at least one modified amino acid residue in a strand of the OB-fold domain loop region is mutated by substitution as compared to the naturally occurring OB-fold domain amino acid residue,
   wherein said isolated modified OB-fold domain is selected from the group consisting of Pyrobaculum aerophilum Asp tRNA synthase OB-fold domain having between 4 and 17 mutated amino acids and Pyrobaculum aerophilum initiation factor IF-5A OB-fold domain having between 2 and 11 mutated amino acid residues;
   and wherein said modified OB-fold domain is soluble and has altered binding characteristics as compared to the naturally occurring OB-fold domain, and wherein said domain specifically binds to a different binding partner than the naturally occurring OB-fold domain.

2. The modified OB-fold domain of claim 1 wherein said domain has modified binding with its naturally occurring binding partner.

3. The modified OB-fold domain of claim 1 wherein said mutated amino acid residues are in a β-strand of the fold-related binding face.

4. A method of obtaining a modified OB-fold domain of claim 1, comprising:
   a) obtaining nucleic acid encoding a naturally occurring OB-fold domain, or encoding a portion thereof comprising a strand of the binding face and/or a strand of the loop, and
   b) altering the nucleic acid such that it encodes at least one mutated amino acid residue on a β-strand of the binding face and/or at least one mutated amino acid residue on a strand of a loop as compared to the naturally occurring OB-fold domain, wherein a modified OB-fold domain is obtained and wherein said modified OB-fold domain has altered binding as compared to said naturally occurring OB-fold domain.

5. The method of claim 4 further comprising altering nucleic acid encoding said modified OB-fold domain, and/or altering nucleic acid encoding at least one amino acid of a protein that comprises said modified OB-fold domain.

6. A method of producing a library of modified OB-fold domains for display comprising,
   a) obtaining nucleic acid encoding an OB-fold domain, or a portion thereof,
   b) subjecting said nucleic acid to random alterations, to produce a collection of altered nucleic acid encoding modified OB-fold domains having at least four randomized amino acid residues, and
   c) selecting soluble modified OB-fold domains for the library;
   wherein said library comprises OB-fold domains according to claim 1.

7. The method of claim 6 wherein said nucleic acid encodes at least one mutated amino acid residue of a strand of the OB-fold domain binding face and/or a strand of an OB-fold domain loop.

8. The method of claim 6, further comprising placing the library of altered nucleic acid encoding modified OB-fold domains into a population of host cells capable of displaying said modified OB-fold domains on their surface.

9. An isolated nucleic acid encoding the modified OB-fold domain of claim 1.

10. A host cell comprising a nucleic acid encoding the modified OB-fold domain of claim 1.

11. A phage comprising a nucleic acid encoding the modified OB-fold domain of claim 1.

12. A composition comprising a nucleic acid encoding the modified OB-fold domain of claim 1.

13. A method of screening a library of modified OB-fold domains according to claim 1 for binding with a binding partner, comprising:
   a) obtaining a population of host cells or viral particles displaying a library of modified OB-fold domains according to claim 1 on their surface;
   b) contacting said population of host cells or viral particles with said binding partner under conditions suitable for binding of said binding partner to said modified OB-fold domain; and
   c) determining binding of said binding partner to said modified OB-fold domain.

14. The method of claim 13 wherein said host cells or viral particles are phage that display the modified OB-fold domains on their surface.

15. A phage library of modified OB-fold domains of claim 1, wherein said modified OB-fold domains are obtainable from Pyrobaculum aerophilum.

16. A modified OB-fold domain of claim 1 displayed on the surface of a cell or viral particle.

17. The modified OB-fold domain of claim 16 wherein said cell or viral particle is a phage, bacteria or yeast.

18. A modified OB-fold domain of claim 1 attached to a solid support.

19. The modified OB-fold domain of claim 18 wherein said support is selected from the group consisting of beads, glass, slides, chips, and gelatin.

* * * * *